(12) United States Patent
Fujdala et al.

(10) Patent No.: US 8,585,933 B2
(45) Date of Patent: *Nov. 19, 2013

(54) METHODS FOR AIGS SILVER-CONTAINING PHOTOVOLTAICS

(75) Inventors: Kyle L. Fujdala, San Jose, CA (US); Wayne A. Chomitz, Oakland, CA (US); Zhongliang Zhu, San Jose, CA (US); Matthew C. Kuchta, San Francisco, CA (US); Qinglan Huang, Niskayuna, NY (US)

(73) Assignee: Precursor Energetics, Inc., Santa Clara, CA (US)

( * ) Notice: Subject to any disclaimer, the term of this patent is extended or adjusted under 35 U.S.C. 154(b) by 492 days.

This patent is subject to a terminal disclaimer.

(21) Appl. No.: 12/869,677

(22) Filed: Aug. 26, 2010

(65) Prior Publication Data

US 2011/0030787 A1 Feb. 10, 2011

Related U.S. Application Data

(63) Continuation of application No. 12/848,890, filed on Aug. 2, 2010.

(60) Provisional application No. 61/231,158, filed on Aug. 4, 2009, provisional application No. 61/302,094, filed on Feb. 6, 2010, provisional application No. 61/302,095, filed on Feb. 6, 2010, provisional application No. 61/326,540, filed on Apr. 21, 2010.

(51) Int. Cl.
*H01B 1/00* (2006.01)
*H01B 1/12* (2006.01)
*H01L 31/00* (2006.01)
*H01L 21/00* (2006.01)

(52) U.S. Cl.
USPC ............ 252/500; 118/46; 118/52; 118/75; 118/300; 136/252; 136/258; 136/262; 204/194; 252/519.14; 257/E31.026; 257/E31.027; 257/E31.04; 438/95

(58) Field of Classification Search
USPC ........ 118/46, 52, 75, 300; 136/252, 262, 258; 204/194; 252/519.14, 519.2, 519.21, 252/519.32, 519.34, 519.4, 500; 257/E21.114, E31.026, E31.027, 257/E31.04; 438/95, 478; 525/389; 556/110

See application file for complete search history.

(56) References Cited

U.S. PATENT DOCUMENTS

| | | | |
|---|---|---|---|
| 2,514,981 A | 7/1950 | Walker | |
| 4,335,266 A | 6/1982 | Mickelsen | |

(Continued)

FOREIGN PATENT DOCUMENTS

| | | |
|---|---|---|
| EP | 0534459 A2 | 3/1993 |
| JP | 5790867 | 6/1982 |

(Continued)

OTHER PUBLICATIONS

Mohammad Afzaal, Theivanayagam C. Deivaraj, Paul O'Brien, Jin-Ho Park, and Jagadese J. Vittal, Single-Source Approach for the Growth of I-III-VI Thin Films, Mat. Res. Soc. Symp. Proc. vol. 730, V5.22.1-V5.22.6 © 2002 Materials Research Society.*

(Continued)

*Primary Examiner* — Bijan Ahvazi
(74) *Attorney, Agent, or Firm* — Eckman Basu LLP

(57) ABSTRACT

This invention relates to methods for making materials using compounds, polymeric compounds, and compositions used to prepare semiconductor and optoelectronic materials and devices including thin film and band gap materials. This invention provides a range of compounds, polymeric compounds, compositions, materials and methods directed ultimately toward photovoltaic applications, transparent conductive materials, as well as devices and systems for energy conversion, including solar cells. This invention further relates to methods for making AIGS, AIS or AGS materials by providing one or more polymeric precursor compounds or inks thereof, providing a substrate, depositing the compounds or inks onto the substrate; and heating the substrate at a temperature of from about 20° C. to about 650° C.

19 Claims, 20 Drawing Sheets

(56) References Cited

U.S. PATENT DOCUMENTS

| | | | |
|---|---|---|---|
| 5,436,204 A | 7/1995 | Albin |
| 5,441,897 A | 8/1995 | Noufi |
| 5,681,975 A | 10/1997 | Brennan |
| 5,871,630 A | 2/1999 | Bhattacharya |
| 5,882,722 A | 3/1999 | Kydd |
| 5,976,614 A | 11/1999 | Bhattacharya |
| 5,981,868 A | 11/1999 | Kushiya |
| 5,985,691 A | 11/1999 | Basol |
| 6,066,196 A | 5/2000 | Kaloyeros |
| 6,126,740 A | 10/2000 | Schulz |
| 6,325,490 B1 | 12/2001 | Yang |
| 6,368,892 B1 | 4/2002 | Arya |
| 6,372,538 B1 | 4/2002 | Wendt |
| 6,500,733 B1 | 12/2002 | Stanbery |
| 6,518,086 B2 | 2/2003 | Beck |
| 6,635,307 B2 | 10/2003 | Huang |
| 6,797,874 B2 | 9/2004 | Stanbery |
| 6,830,778 B1 | 12/2004 | Schulz |
| 6,852,920 B2 | 2/2005 | Sager |
| 6,875,661 B2 | 4/2005 | Mitzi |
| 6,967,115 B1 | 11/2005 | Sheats |
| 6,974,976 B2 | 12/2005 | Hollars |
| 6,987,071 B1 | 1/2006 | Bollman |
| 6,992,202 B1 * | 1/2006 | Banger et al. .................. 556/28 |
| 7,026,258 B2 | 4/2006 | Taunier |
| 7,094,651 B2 | 8/2006 | Mitzi |
| 7,109,520 B2 | 9/2006 | Yu |
| 7,179,677 B2 | 2/2007 | Ramanathan |
| 7,194,197 B1 | 3/2007 | Wendt |
| 7,235,736 B1 | 6/2007 | Buller |
| 7,247,346 B1 | 7/2007 | Sager |
| 7,259,322 B2 | 8/2007 | Gronet |
| 7,306,823 B2 | 12/2007 | Sager |
| 7,341,917 B2 | 3/2008 | Milliron |
| 7,384,680 B2 | 6/2008 | Bi |
| 7,494,841 B2 | 2/2009 | Mitzi |
| 7,517,718 B2 | 4/2009 | Mitzi |
| 7,563,392 B1 | 7/2009 | Hsu |
| 7,618,841 B2 | 11/2009 | Mitzi |
| 7,663,057 B2 | 2/2010 | Yu |
| 2003/0123167 A1 | 7/2003 | Kolberg |
| 2004/0063320 A1 | 4/2004 | Hollars |
| 2004/0250848 A1 | 12/2004 | Sager |
| 2005/0121068 A1 | 6/2005 | Sager |
| 2005/0183767 A1 * | 8/2005 | Yu et al. ...................... 136/263 |
| 2006/0060237 A1 | 3/2006 | Leidholm |
| 2006/0062902 A1 | 3/2006 | Sager |
| 2006/0157103 A1 | 7/2006 | Sheats |
| 2007/0163383 A1 | 7/2007 | Van Duren |
| 2007/0163637 A1 | 7/2007 | Robinson |
| 2007/0163638 A1 | 7/2007 | Van Duren |
| 2007/0163639 A1 | 7/2007 | Robinson |
| 2007/0163640 A1 | 7/2007 | Van Duren |
| 2007/0163641 A1 | 7/2007 | Van Duren |
| 2007/0163642 A1 | 7/2007 | Van Duren |
| 2007/0163643 A1 | 7/2007 | Van Duren |
| 2007/0163644 A1 | 7/2007 | Van Duren |
| 2007/0169812 A1 | 7/2007 | Robinson |
| 2007/0169813 A1 | 7/2007 | Robinson |
| 2007/0178620 A1 | 8/2007 | Basol |
| 2007/0207565 A1 | 9/2007 | Kodas |
| 2007/0264488 A1 | 11/2007 | Lee |
| 2008/0057203 A1 | 3/2008 | Robinson |
| 2008/0057616 A1 | 3/2008 | Robinson |
| 2008/0124833 A1 | 5/2008 | Ruiz |
| 2008/0135099 A1 | 6/2008 | Yu |
| 2008/0135811 A1 | 6/2008 | Yu |
| 2008/0135812 A1 | 6/2008 | Yu |
| 2008/0138501 A1 | 6/2008 | Yu |
| 2008/0142072 A1 | 6/2008 | Yu |
| 2008/0142080 A1 | 6/2008 | Yu |
| 2008/0142081 A1 | 6/2008 | Yu |
| 2008/0142082 A1 | 6/2008 | Yu |
| 2008/0142083 A1 | 6/2008 | Yu |
| 2008/0142084 A1 | 6/2008 | Yu |
| 2008/0145633 A1 | 6/2008 | Kodas |
| 2008/0149176 A1 | 6/2008 | Sager |
| 2008/0175982 A1 | 7/2008 | Robinson |
| 2008/0213467 A1 | 9/2008 | Yu |
| 2008/0257201 A1 | 10/2008 | Harris |
| 2009/0084427 A1 | 4/2009 | Anderson |
| 2009/0107550 A1 | 4/2009 | Van Duren |
| 2009/0169723 A1 | 7/2009 | Hanket |
| 2009/0253227 A1 | 10/2009 | Defries |
| 2009/0260670 A1 | 10/2009 | Li |
| 2009/0280598 A1 | 11/2009 | Curtis |
| 2009/0280624 A1 | 11/2009 | Curtis |
| 2010/0029036 A1 | 2/2010 | Robinson |
| 2010/0291758 A1 | 11/2010 | Robinson |
| 2011/0030797 A1 * | 2/2011 | Fujdala et al. ................. 136/262 |

FOREIGN PATENT DOCUMENTS

| | | | | |
|---|---|---|---|---|
| JP | 10-273783 A | 10/1998 | | |
| JP | 2000-058893 A | 2/2000 | | |
| JP | 200283824 | 3/2002 | | |
| JP | 2008056511 | 8/2006 | | |
| JP | 2008-56511 A | 3/2008 | | |
| KR | 10-2009-0029495 A | 3/2009 | | |
| KR | 10-2009-0050558 A | 5/2009 | | |
| WO | WO9304212 A1 | 3/1993 | | |
| WO | WO2007082080 A1 | 7/2007 | | |
| WO | WO 2008057119 A1 * | 5/2008 | ............. C30B 29/46 |
| WO | WO2008057119 A1 | 5/2008 | | |
| WO | WO2008063190 A2 | 5/2008 | | |
| WO | WO2008104087 A1 | 9/2008 | | |
| WO | WO2009064056 A1 | 5/2009 | | |

OTHER PUBLICATIONS

Banger, K K et al., Applied Organometallic Chemistry, 2002 ; 16: 617-627.
Banger, K K et al., Inorg Chem, 2003 ; 42(24): 7713-7715.
Chen, Yu et al., Chem Mater, 2007 ; 19: 5256-5261.
Dennler, Gilles et al., Adv Mater, 2009 ; 21: 1323-1338.
Kaelin, M et al., Solar Energy, 2004 ; 77: 749-756.
Kundu, Sambhu N. et al., Thin Solid Films, 2006 ; 515: 2625-2631.
Yoon, Seok Hwan et al., Bull Korean Chem Soc, 2006 ; 27(12): 2071-2073.
Eichofer, J. Chem. Soc., Dalton Trans., 2000, 941-944.
Chen, Physical Review B 79, 165211, 1-10 (2009).
Beachley, Organometallics 1996, 15, 3653-3658.
Borisova, Organometallics 2002, 21, 4005-4008.
Deivaraj, Inorg. Chem. 2002, 41, 3755-3760.
Deivaraj, Chem. Mater. 2003, 15, 2383-2391.
Kuckmann, Inorg. Chem. 2005, 44, 3449-3458.
Lazell, Chem. Mater. 1999, 11, 3430-3432.
Malik, Chem. Mater. 2001, 13, 913-920.
McAleese, Chem. Vap. Deposition 1998, 4, No. 3, 94-96.
Nguyen, Chem. Commun., 2006, 2182-2184.
Nomura, Polyhedron 1989, vol. 8, No. 15, 1891-1896.
Nomura, J. Mater. Chem., 1992, 2(7), 765-766.
Stoll, Chem. Mater. 1998, 10, 650-657.
Tian, Inorg. Chem. 2006, 45, 8258-8263.
Tran, Organometallics 2000, 19, 5202-5208.
Wallbank, Organometallics 2005, 24, 788-790.
Kumar, J. Chem. Soc. Dalton Trans. 1988, p. 1045-1047, Reactions of Some Main Group Metals with Diphenyl Disulphide and Diphenyl Diselenide.
Green, Inorg. Chem. 1989, V28, 123-127.
Nomura, Polyhedron vol. 9, No. 2/3, pp. 361-366, 1990.
Nomura, Applied Organometallic Chemistry, vol. 6, 685-691 (1992).
Hirpo, J. Am. Chem. Soc. 1993, V115, 1597-1599.
Ohlmann, J. Chem. Soc., Chem. Commun., 1995, p. 1011-1012.
Beck, Thin Solid Films 272 ( 1996) 71-82.
Grigsby, J. Chem. Soc., Dalton Trans., 1998, pp. 2547-2556.
Suh, Inorg. Chem. 1999, 38, 1627-1633.
Banger, Chem. Mater. 2001, 13, 3827-3829.
Deivaraj, Chem. Commun., 2001, 2304-2305.

(56) References Cited

OTHER PUBLICATIONS

Kapur, Thin Solid Films 431-432 (2003) 53-57.
Ahlrichs, Eur. J. Inorg. Chem. 2006, 345-350.
Milliron, Chem. Mater., vol. 18, No. 3, 2006, p. 587-590.
Vittal, Acc. Chem. Res. 2006, 39, 869-877.
Yamada, Science and Technology of Advanced Materials 7 (2006) 42-45.
Borecki, Inorg. Chem. 2007, 46, 2478-2484.
Schneider, Chem. Mater. 2007, 19, 2780-2785.
Merdes, Thin Solid Films 516 (2008) 7335-7339.
Panthani, J. Am. Chem. Soc. 2008, 130, 16770-16777.
Hepp, Solution Processing of Inorganic Materials, edited by David Mitzi, 2009, Chapter 6, p. 157-198.
Hou, Thin Solid Films (2009) pp. 1-4, Low-temperature processing of a solution-deposited CuInSSe thin-film solar cell.
Malik, J. Mater. Res., vol. 24, No. 4, Apr. 2009, p. 1375-1387.
Mitzi, Thin Solid Films 517 (2009) 2158-2162.
Park, Journal of CrystalGrowth 311 (2009) 2621-2625.
Dwyer, Solar Energy Materials & Solar Cells 94 (2010) 598-605.
Hibberd, Prog. Photovolt: Res. Appl. 2010; 18:434-452.
Niki, Prog. Photovolt: Res. Appl. 2010; 18:453-466.
Yuan, Chem. Mater. 2010, 22, 285-287.
Zhong, Chem. Mater. 2008, vol. 20, pp. 6434-6443.

\* cited by examiner

[BA]₄ cyclic

METHODS FOR AIGS SILVER-CONTAINING PHOTOVOLTAICS

CROSS REFERENCE TO RELATED APPLICATIONS

This application is a continuation of prior U.S. application Ser. No. 12/848,890, filed Aug. 2, 2010, which claims the benefit of U.S. Provisional Application No. 61/231,158, filed Aug. 4, 2009, U.S. Provisional Application No. 61/302,094, filed Feb. 6, 2010, U.S. Provisional Application No. 61/302,095, filed Feb. 6, 2010, and U.S. Provisional Application No. 61/326,540, filed Apr. 21, 2010, each of which is hereby incorporated by reference in its entirety.

BACKGROUND

The development of photovoltaic devices such as solar cells is important for providing a renewable source of energy and many other uses. The demand for power is ever-rising as the human population increases. In many geographic areas, solar cells may be the only way to meet the demand for power. The total energy from solar light impinging on the earth for one hour is about $4 \times 10^{20}$ joules. It has been estimated that one hour of total solar energy is as much energy as is used worldwide for an entire year. Thus, billions of square meters of efficient solar cell devices will be needed.

Photovoltaic devices are made by a variety of processes in which layers of semiconducting material are created on a substrate. Layers of additional materials are used to protect the photovoltaic semiconductor layers and to conduct electrical energy out of the device. Thus, the usefulness of an optoelectronic or solar cell product is in general limited by the nature and quality of the photovoltaic layers.

For example, one way to produce a solar cell product involves depositing a thin, light-absorbing, solid layer of the material copper indium gallium diselenide, known as "CIGS," on a substrate. A solar cell having a thin film CIGS layer can provide low to moderate efficiency for conversion of sunlight to electricity. The CIGS layer can be made by processing at relatively high temperatures several elemental sources containing the atoms needed for CIGS. In general, CIGS materials are complex, having many possible solid phases.

The CIGS elemental sources must be formed or deposited, either individually or as a mixture, in a thin, uniform layer on the substrate. For example, deposition of the CIGS sources can be done as a co-deposition, or as a multistep deposition. The difficulties with these approaches include lack of uniformity of the CIGS layers, such as the appearance of different solid phases, imperfections in crystalline particles, voids, cracks, and other defects in the layers.

For example, some methods for solar cells are disclosed in U.S. Pat. Nos. 5,441,897, 5,976,614, 6,518,086, 5,436,204, 5,981,868, 7,179,677, 7,259,322, U.S. Patent Publication No. 2009/0280598, and PCT International Application Publication Nos. WO2008057119 and WO2008063190.

A significant problem is the inability in general to precisely control the stoichiometric ratios of the metal atoms in the layers. Many semiconductor and optoelectronic applications are highly dependent on the ratios of certain metal atoms in the material. Without direct control over those stoichiometric ratios, processes to make semiconductor and optoelectronic materials are often less efficient and less successful in achieving desired compositions and properties. For example, no molecule is currently known that can be used alone, without other compounds, to readily prepare a layer from which CIGS materials of any arbitrary stoichiometry can be made. Compounds or compositions that can fulfill this goal have long been needed.

A further difficulty is the need to heat the substrate to high temperatures to finish the film. This can cause unwanted defects due to rapid chemical or physical transformation of the layers. High temperatures may also limit the nature of the substrate that can be used. For example, it is desirable to make thin film photovoltaic layers on a flexible substrate such as a polymer or plastic that can be formed into a roll for processing and installation on a building or outdoor structure. Polymer substrates may not be compatible with the high temperatures needed to process the semiconductor layers. Preparing thin film photovoltaic layers on a flexible substrate is an important goal for providing renewable solar energy and developing new generations of electro-optical products.

Moreover, methods for large scale manufacturing of CIGS and related thin film solar cells can be difficult because of the chemical processes involved. In general, large scale processes for solar cells are unpredictable because of the difficulty in controlling numerous chemical and physical parameters involved in forming an absorber layer of suitable quality on a substrate, as well as forming the other layers required to make an efficient solar cell and provide electrical conductivity.

What is needed are compounds, compositions and processes to produce materials for photovoltaic layers, especially thin film layers for solar cell devices and other products.

BRIEF SUMMARY

This invention relates to compounds and compositions used to prepare semiconductor and optoelectronic materials and devices including thin film and band gap materials. This invention provides a range of compounds, compositions, materials and methods directed ultimately toward photovoltaic applications and other semiconductor materials, as well as devices and systems for energy conversion, including solar cells. In particular, this invention relates to novel processes, compounds and materials for preparing semiconductor materials including CAIGS Cu/Ag/In/Ga/S/Se materials.

This invention provides a range of compounds, compositions, materials and methods for preparing semiconductors and materials, as well as optoelectronic devices and photovoltaic layers. Among other things, this disclosure provides precursor molecules and compositions for making and using semiconductors such as for photovoltaic layers, solar cells and other uses. In particular, this invention encompasses compounds and compositions containing a combination of the elements copper, silver, indium, gallium, selenium, and sulfur, including CuAgInGaS/Se or CAIGS, which are useful for thin film solar cells and other uses.

In some embodiments, this invention includes polymeric precursor compounds and compositions for preparing semiconductors, optoelectronic devices and photovoltaic layers.

The compounds and compositions of this disclosure are stable and advantageously allow control of the stoichiometry of the atoms in the semiconductors, particularly the metal atoms.

In various embodiments of this invention, chemically and physically uniform semiconductor layers can be prepared with the polymeric precursor compounds described herein.

The compounds and compositions of this disclosure are useful to prepare semiconductor layers having enhanced uniformity and superior properties.

In further embodiments, solar cells and other products can be made in processes operating at relatively low temperatures with the compounds and compositions of this disclosure.

The polymeric precursor compounds and compositions of this disclosure can provide enhanced processability for solar cell production, and the ability to be processed on a variety of substrates including polymers at relatively low temperatures.

The advantages provided by the compounds, compositions, and materials of this invention in making photovoltaic layers and other semiconductors and devices are generally obtained regardless of the morphology or architecture of the semiconductors or devices.

In some embodiments, this invention provides a range of compounds comprising repeating units $\{M^B(ER)(ER)\}$ and $\{M^B(ER)(ER)\}$, wherein each $M^A$ is Cu or Ag, each $M^B$ is In or Ga, each E is S, Se, or Te, and each R is independently selected, for each occurrence, from alkyl, aryl, heteroaryl, alkenyl, amido, silyl, and inorganic and organic ligands. A compound may be a CAIGS, AIGS, CAIS, CAGS, AIS, or AGS precursor compound. A compound can have the empirical formula $(Cu_{1-x}Ag_x)_u(M^{B1}_{1-y}M^{B2}_y)_v((S_{1-z}Se_z)R)_w$, wherein $M^{B1}$ and $M^{B2}$ are different atoms of Group 13, wherein x is from 0 to 1, y is from 0 to 1, z is from 0 to 1, u is from 0.5 to 1.5, v is from 0.5 to 1.5, w is from 2 to 6, and R represents R groups, of which there are w in number, which are each independently selected from alkyl, aryl, heteroaryl, alkenyl, amido, silyl, and inorganic and organic ligands. A compound may be deficient or enriched in the quantity of a Group 11 atom. A compound can be an inorganic polymer or coordination polymer, and may be linear, branched, cyclic, or a mixture of any of the foregoing. A compound can be an alternating copolymer, a block copolymer, or a random copolymer.

In some aspects, a compound may have any one of the formulas: $(RE)_2$-$BB(AB)_n$, $(RE)_2$-$B(AB)_nB$, $(RE)_2$-$B(AB)_nB(AB)_m$, $(RE)_2$-$(BA)_nBB$, $(RE)_2$-$B(BA)_nB$, $(RE)_2$-$(BA)_nB(BA)_mB$, $^{cyclic}(AB)_n$, $^{cyclic}(BA)_n$, $(RE)_2$-$(BB)(AABB)_n$, $(RE)_2$-$(BB)(AABB)_n(AB)_m$, $(RE)_2$-$(B)(AABB)_n(B)(AB)_m$, $(RE)_2$-$[B(AB)_n]^-$, $(RE)_2$-$[(BA)_nB]^-$,

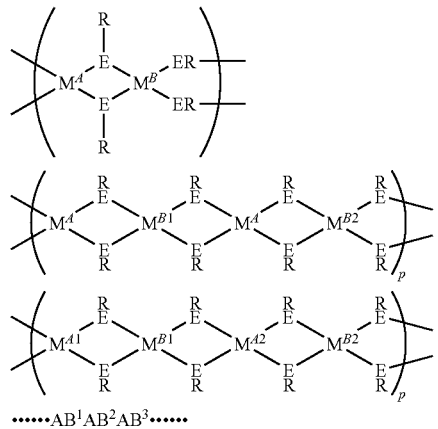

······$AB^1AB^2AB^3$······

$(RE)_2$-$BB(AB^1)_n(AB^2)_m$, $(RE)_2$-$BB(AB^1)_n(AB^2)_m(AB^1)_p$, $(RE)_2$-$BB(AB^1)_n(AB^2)_m(AB^1)_p$, $(RE)_2$-$BB(A^1B)_n(A^2B)_m$, $(RE)_2$-$BB(A^1B)_n(A^2B)_m(A^1B)_p$, and a mixture of any of the foregoing, wherein A is the repeat unit $\{M^A(ER)(ER)\}$, B is the repeat unit $\{M^B(ER)(ER)\}$, p is one or more, n is one or more, or n is two or more, or n is three or more, and m is one or more.

Embodiments of this invention may further provide an ink comprising one or more precursor compounds above and one or more carriers. An ink may be a solution of the compounds in an organic carrier, and may contain a dopant or alkali dopant. An ink may further contain one or more components selected from the group of a surfactant, a dispersant, an emulsifier, an anti-foaming agent, a dryer, a filler, a resin binder, a thickener, a viscosity modifier, an anti-oxidant, a flow agent, a plasticizer, a conductivity agent, a crystallization promoter, an extender, a film conditioner, an adhesion promoter, and a dye.

This disclosure further provides methods for making a precursor compound comprising: a) providing monomer compounds $M^{B1}(ER)_3$, $M^{B2}(ER)_3$, $M^{A1}(ER)$ and $M^{A2}(ER)$; and b) contacting the monomer compounds; wherein $M^{B1}$ is In, $M^{B2}$ is Ga, $M^{A1}$ is Cu, and $M^{A2}$ is Ag, each E is S, Se, or Te, and each R is independently selected, for each occurrence, from alkyl, aryl, heteroaryl, alkenyl, amido, silyl, and inorganic and organic ligands. In certain embodiments, the methods provide a CAIGS, AIGS, CAIS, CAGS, AIS, or AGS precursor compound.

In further aspects, this invention includes articles comprising one or more compounds or inks above deposited onto a substrate. The depositing can be done by spraying, spray coating, spray deposition, spray pyrolysis, printing, screen printing, inkjet printing, aerosol jet printing, ink printing, jet printing, stamp/pad printing, transfer printing, pad printing, flexographic printing, gravure printing, contact printing, reverse printing, thermal printing, lithography, electrophotographic printing, electrodepositing, electroplating, electroless plating, bath deposition, coating, dip coating, wet coating, spin coating, knife coating, roller coating, rod coating, slot die coating, meyerbar coating, lip direct coating, capillary coating, liquid deposition, solution deposition, layer-by-layer deposition, spin casting, solution casting, and combinations of any of the forgoing. The substrate may be selected from a semiconductor, a doped semiconductor, silicon, gallium arsenide, insulators, glass, molybdenum glass, silicon dioxide, titanium dioxide, zinc oxide, silicon nitride, a metal, a metal foil, molybdenum, aluminum, beryllium, cadmium, cerium, chromium, cobalt, copper, gallium, gold, lead, manganese, molybdenum, nickel, palladium, platinum, rhenium, rhodium, silver, stainless steel, steel, iron, strontium, tin, titanium, tungsten, zinc, zirconium, a metal alloy, a metal silicide, a metal carbide, a polymer, a plastic, a conductive polymer, a copolymer, a polymer blend, a polyethylene terephthalate, a polycarbonate, a polyester, a polyester film, a mylar, a polyvinyl fluoride, polyvinylidene fluoride, a polyethylene, a polyetherimide, a polyethersulfone, a polyetherketone, a polyimide, a polyvinylchloride, an acrylonitrile butadiene styrene polymer, a silicone, an epoxy, paper, coated paper, and combinations of any of the forgoing. The substrate may be a shaped substrate including a tube, a cylinder, a roller, a rod, a pin, a shaft, a plane, a plate, a blade, a vane, a curved surface or a spheroid.

In some embodiments, this invention provides methods for making an article by (a) providing one or more compounds or inks above; (b) providing a substrate; and (c) depositing the compounds or inks onto the substrate.

This invention includes materials having the empirical formula $(Cu_{1-x}Ag_x)_u(In_{1-y}Ga_y)_v(S_{1-z}Se_z)_w$, where x is from 0.001 to 1, y is from 0 to 1, z is from 0 to 1, u is from 0.5 to 1.5, v is from 0.5 to 1.5, and w is from 1 to 3.

In certain embodiments, this invention provides methods for making a material comprising, (a) providing one or more compounds or above; (b) providing a substrate; (c) depositing the compounds or inks onto the substrate; and (d) heating the substrate at a temperature of from about 20° C. to about 650° C. in an inert atmosphere, thereby producing a material.

In some embodiments, this disclosure provides a thin film material made by a process comprising, (a) providing one or more compounds or inks above; (b) providing a substrate; (c) depositing the compounds or inks onto the substrate; and (d) heating the substrate at a temperature of from about 20° C. to about 650° C. in an inert atmosphere, thereby producing a thin film material having a thickness of from 0.05 to 10 micrometers.

In further embodiments, this invention discloses a photovoltaic absorber having the empirical formula $(Cu_{1-x}Ag_x)_u(In_{1-y}Ga_y)_v(S_{1-z}Se_z)_w$, where x is from 0.001 to 1, y is from 0 to 1, z is from 0 to 1, u is from 0.5 to 1.5, v is from 0.5 to 1.5, and w is from 1 to 3.

Embodiments of this invention include methods for making a photovoltaic absorber layer on a substrate comprising, (a) providing one or more compounds or inks above; (b) providing a substrate; (c) depositing the compounds or inks onto the substrate; and (d) heating the substrate at a temperature of from about 100° C. to about 650° C. in an inert atmosphere, thereby producing a photovoltaic absorber layer having a thickness of from 0.001 to 100 micrometers.

In some embodiments, this invention includes a photovoltaic device made with polymeric precursors. In certain aspects, this invention contemplates a photovoltaic system and methods for providing electrical power using a photovoltaic device or system to convert light into electrical energy.

This brief summary, taken along with the detailed description of the invention, as well as the figures, the appended examples and claims, as a whole, encompass the disclosure of the invention.

BRIEF DESCRIPTION OF THE DRAWINGS

As shown in FIG. 1, the structure of the compound can be represented by the formula $(RE)_2$BABABB, wherein A is the repeat unit $\{M^A(ER)_2\}$, B is the repeat unit $\{M^B(ER)_2\}$, E is a chalcogen, and R is a functional group.

As shown in FIG. 2, the structure of the compound can be represented by the formula $(RE)_2$BABABBABAB, wherein A is the repeat unit $\{M^A(ER)_2\}$, B is the repeat unit $\{M^B(ER)_2\}$, E is a chalcogen, and R is a functional group.

As shown in FIG. 3, the structure of the compound can be represented by the formula $(RE)_2$BA(BA)$_n$BB, wherein A is the repeat unit $\{M^A(ER)_2\}$, B is the repeat unit $\{M^B(ER)_2\}$, E is a chalcogen, and R is a functional group.

As shown in FIG. 4, the structure of the compound can be represented by the formula $(RE)_2$BA(BA)$_n$B(BA)$_m$B, wherein A is the repeat unit $\{M^A(ER)_2\}$, B is the repeat unit $\{M^B(ER)_2\}$, E is a chalcogen, and R is a functional group.

As shown in FIG. 5, the structure of the compound can be represented by the formula $^{cyclic}(BA)_4$, wherein A is the repeat unit $\{M^A(ER)_2\}$, B is the repeat unit $\{M^B(ER)_2\}$, E is a chalcogen, and R is a functional group.

DETAILED DESCRIPTION

Figure 1:
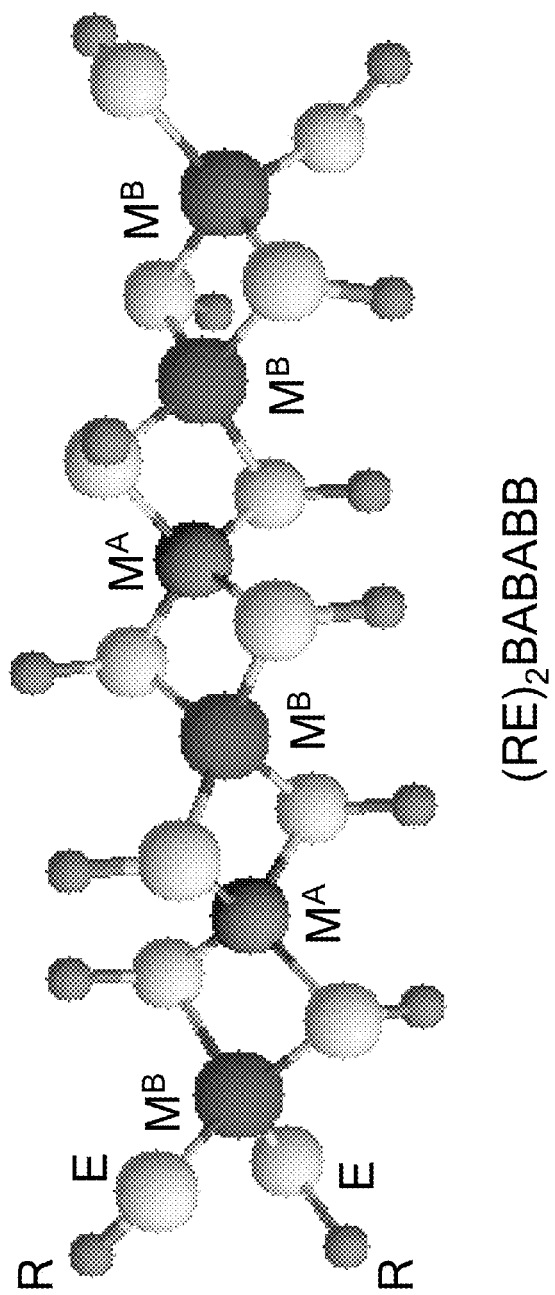
FIG. 1 shows an embodiment of a polymeric precursor compound (MPP-CAIGS).

This disclosure provides a range of novel polymeric compounds, compositions, materials and methods for semiconductor and optoelectronic materials and devices including thin film photovoltaics and various semiconductor band gap materials.

Among other advantages, the polymeric compounds, compositions, materials and methods of this invention can provide a precursor compound for making semiconductor and optoelectronic materials, including CAIGS absorber layers for solar cells and other devices. In some embodiments, the optoelectronic source precursor compounds of this invention can be used alone, without other compounds, to prepare a layer from which CAIGS, AIGS, CAIS, CAGS, AIS, AGS and other materials can be made. CAIGS refers to Cu/Ag/In/Ga/S/Se, and further definitions are given below.

Polymeric precursor compounds may also be used in a mixture with additional compounds to control stoichiometry of a layer or material.

In general, the ability to select a predetermined stoichiometry in advance means that the stoichiometry is controllable.

This invention provides polymeric compounds and compositions for photovoltaic applications, as well as devices and systems for energy conversion, including solar cells.

The polymeric compounds and compositions of this disclosure include polymeric precursor compounds and polymeric precursors for materials for preparing novel semiconductor and photovoltaic materials, films, and products. Among other advantages, this disclosure provides stable polymeric precursor compounds for making and using layered materials and photovoltaics, such as for solar cells and other uses.

A photovoltaic absorber material of this disclosure can retain the precise stoichiometry of the precursor used to make the absorber material.

Polymeric precursors can advantageously form a thin, uniform film. In some embodiments, a polymeric precursor is an oil that can be processed and deposited in a uniform layer on a substrate. This invention provides polymeric precursors that can be used neat to make a thin film, or can be processed in an ink composition for deposition on a substrate. The polymeric precursors of this invention can have superior processability to form a thin film for making photovoltaic absorber layers and solar cells.

In certain aspects, this invention provides polymeric precursor compounds having enhanced solubility in organic solvents. The solubility of a polymeric precursor makes it advantageous for preparing photovoltaic materials using any one of various processes that require deposition of the precursor on a substrate, such as for making thin film solar cells. A polymeric precursor may have enhanced solubility in one or more carriers for preparing an ink to be deposited on a substrate.

In further embodiments, this invention provides a range of polymeric precursor compounds for which the solubility can advantageously be controlled and selectively varied. In these embodiments, the solubility of a polymeric precursor can be enhanced by variation of the nature and molecular size and weight of one or more organic ligands attached to the compound. The control of polymeric precursor solubility can allow the preparation of inks having controlled viscosity, for example, among other properties.

In general, the structure and properties of the polymeric compounds, compositions, and materials of this invention provide advantages in making photovoltaic layers, semiconductors, and devices regardless of the morphology, architecture, or manner of fabrication of the semiconductors or devices.

The polymeric precursor compounds of this invention are desirable for preparing semiconductor materials and compositions. A polymeric precursor may have a chain structure containing two or more different metal atoms which may be bound to each other through interactions or bridges with one or more chalcogen atoms of chalcogen-containing moieties.

With this structure, when a polymeric precursor is used in a process such as deposition, coating or printing on a substrate or surface, as well as processes involving annealing, sintering, thermal pyrolysis, and other semiconductor manufacturing processes, use of the polymeric precursors can enhance the formation of a semiconductor and its properties.

The polymeric precursor compounds and compositions of this invention may advantageously be used in processes for solar cells that avoid additional sulfurization or selenization steps.

For example, the use of a polymeric precursor in semiconductor manufacturing processes can enhance the formation of M-E-M' bonding, such as is required for chalcogen-containing semiconductor compounds and materials, wherein M is an atom of one of Groups 3 to 12, M' is an atom of Group 13, and E is a chalcogen.

In some embodiments, a polymeric precursor compound contains a chalcogenide bridge having the formula $M^A(E)M^A$, $M^B(E)M^B$ or $M^A(E)M^B$.

A polymeric precursor compound may advantageously contain linkages between atoms, where the linkages are desirably found in a material of interest, such as a CAIGS, AIGS, CAIS, CAGS, AIS, or AGS material, which material can be made from the polymeric precursor, or a combination of polymeric precursors.

The polymeric precursor compounds of this disclosure are stable and advantageously allow control of the stoichiometry, structure, and ratios of the atoms in a semiconductor material or layer, in particular, the metal atoms.

Using polymeric precursor compounds in any particular semiconductor manufacturing process, the stoichiometry of the metal atoms can be determined and controlled. The structure of a polymeric precursor may contain a number of different metal atoms. Polymeric precursors having different metal atoms, and different numbers of metal atoms can be contacted in precise amounts to control the metal atom stoichiometry in a semiconductor manufacturing process. For processes operating at relatively low temperatures, such as certain printing, spraying, and deposition methods, the polymeric precursor compounds can maintain the desired stoichiometry. As compared to processes involving multiple sources for semiconductor preparation, the polymeric precursors of this invention can provide enhanced control of uniformity.

These advantageous features allow enhanced control over the structure of a semiconductor material made with the polymeric precursor compounds of this invention. The polymeric precursors of this disclosure are superior building blocks for semiconductor materials because they may provide atomic-level control of semiconductor composition.

The polymeric precursor compounds, compositions and methods of this disclosure may allow direct and precise control of the stoichiometric ratios of metal atoms. For example, in some embodiments, a polymeric precursor can be used alone, without other compounds, to readily prepare a layer from which CAIGS, AIGS, CAIS, CAGS, AIS, or AGS materials of any arbitrary stoichiometry can be made.

In certain aspects, polymeric precursor compounds can be used to form nanoparticles that can be used in various methods to prepare semiconductor materials. Embodiments of this invention may further provide processes using nanoparticles of polymeric precursors to enhance the formation and properties of a semiconductor material.

In aspects of this invention, chemically and physically uniform semiconductor layers can be prepared with polymeric precursor compounds.

The compounds and compositions of this disclosure are useful to prepare semiconductor layers having enhanced uniformity and superior properties.

In further embodiments, solar cells and other products can be made in processes operating at relatively low temperatures using the polymeric precursor compounds and compositions of this disclosure.

The polymeric precursors of this disclosure are useful to prepare inks that can be used in various methods to prepare semiconductor materials.

The polymeric precursor compounds and compositions of this disclosure can provide enhanced processability for solar cell production.

Certain polymeric precursor compounds and compositions of this disclosure provide the ability to be processed at relatively low temperatures, as well as the ability to use a variety of substrates including flexible polymers in solar cells.

Embodiments of Polymeric Precursors for CAIGS and AIGS Silver-Containing Photovoltaics Embodiments of this invention include:

A compound comprising repeating units $\{M^B(ER)(ER)\}$ and $\{M^A(ER)(ER)\}$, wherein each $M^A$ is Cu or Ag, each $M^B$ is In or Ga, each E is S, Se, or Te, and each R is independently selected, for each occurrence, from alkyl, aryl, heteroaryl, alkenyl, amido, silyl, and inorganic and organic ligands.

A compound comprising two or more repeating units $\{M^B(ER)(ER)\}$ and two or more repeating units $\{M^A(ER)(ER)\}$, wherein each $M^A$ is Cu or Ag, each $M^B$ is In or Ga, each E is S, Se, or Te, and each R is independently selected, for each occurrence, from alkyl, aryl, heteroaryl, alkenyl, amido, silyl, and inorganic and organic ligands.

A compound comprising repeating units $\{M^B(ER)(ER)\}$ or $\{M^A(ER)(ER)\}$, wherein each $M^A$ is Cu or Ag, each $M^B$ is In or Ga, each E is S, Se, or Te, and each R is independently selected, for each occurrence, from alkyl, aryl, heteroaryl, alkenyl, amido, silyl, and inorganic and organic ligands.

A polymeric compound comprising repeating units $\{M^B(ER)(ER)\}$ and $\{M^A(ER)(ER)\}$, wherein each $M^A$ is Cu or Ag, each $M^B$ is In or Ga, each E is S, Se, or Te, and each R is independently selected, for each occurrence, from alkyl, aryl, heteroaryl, alkenyl, amido, silyl, and inorganic and organic ligands.

The compound above wherein each E is sulfur or selenium.

The compound above wherein E is selenium.

The compound above wherein the compound is a CAIGS, AIGS, CAIS, CAGS, AIS, or AGS precursor compound.

The compound above wherein the compound has the empirical formula $(Cu_{1-x}Ag_x)_u(M^{B1}_{1-y}M^{B2}_y)_v((S_{1-z}Se_z)R)_w$, wherein $M^{B1}$ and $M^{B2}$ are different atoms of Group 13, wherein x is from 0 to 1, y is from 0 to 1, z is from 0 to 1, u is from 0.5 to 1.5, v is from 0.5 to 1.5, w is from 2 to 6, and R represents R groups, of which there are w in number, which are each independently selected from alkyl, aryl, heteroaryl, alkenyl, amido, silyl, and inorganic and organic ligands. In some embodiments, x is from 0.001 to 0.5, y is from 0 to 1, z is from 0.5 to 1, u is from 0.5 to 1.5, v is from 0.5 to 1.5, w is from 2 to 6. In some embodiments, x is from 0.001 to 0.3, y is from 0 to 1, z is from 0.7 to 1, u is from 0.5 to 1.5, v is 1, w is from 3 to 5. In some embodiments, x is from 0.001 to 0.1, y is from 0 to 1, z is from 0.8 to 1, u is from 0.5 to 1.5, v is 1, w is from 3.5 to 4.5.

The compound above wherein the compound is deficient or enriched in the quantity of a Group 11 atom.

The compound above wherein the compound is an inorganic polymer or coordination polymer.

The compound above wherein the compound is linear, branched, cyclic, or a mixture of any of the foregoing.

The compound above wherein each R is independently selected, for each occurrence, from (C1-8)alkyl, or from (C1-6)alkyl, or from (C1-4)alkyl, or from (C1-3)alkyl, or from (C1-2)alkyl.

The compound above wherein the compound is an oil at a temperature below about 100° C.

The compound above further comprising three or more repeating units $\{M^B(ER)(ER)\}$.

The compound above further comprising three or more repeating units $\{M^A(ER)(ER)\}$.

The compound above further comprising the formula $(AB)_n$, wherein A is the repeat unit $\{M^A(ER)(ER)\}$, B is the repeat unit $\{M^B(ER)(ER)\}$, n is two or more, and R is independently selected, for each occurrence, from alkyl, aryl, heteroaryl, alkenyl, amido, silyl, and inorganic and organic ligands.

The compound above wherein the compound is an alternating copolymer, a block copolymer, or a random copolymer.

The compound above wherein the compound has any one of the formulas: $(RE)_2\text{-BB}(AB)_n$, $(RE)_2\text{-B}(AB)_nB$, $(RE)_2\text{-B}(AB)_nB(AB)_m$, $(RE)_2\text{-}(BA)_nBB$, $(RE)_2\text{-B}(BA)_nB$, $(RE)_2\text{-}(BA)_nB(BA)_mB$, $^{cyclic}(AB)_n$, $^{cyclic}(BA)_n$, $(RE)_2\text{-}(BB)(AABB)_n$, $(RE)_2\text{-}(BB)(AABB)_n(AB)_m$, $(RE)_2\text{-}(B)(AABB)_n(B)(AB)_m$, $(RE)_2\text{-}[B(AB)_n]^-$, $(RE)_2\text{-}[(BA)_nB]^-$,

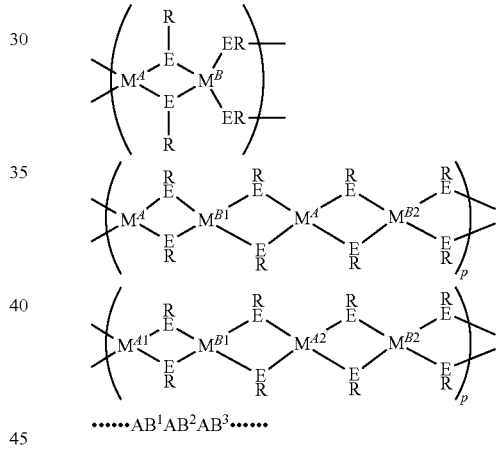

······AB¹AB²AB³······

$(RE)_2\text{-BB}(AB^1)_n(AB^2)_m$, $(RE)_2\text{-BB}(AB^1)_n(AB^2)_m(AB^1)_p$, $(RE)_2\text{-BB}(AB^1)_n(AB^2)_m(AB^1)_p$, $(RE)_2\text{-BB}(A^1B)_n(A^2B)_m$, $(RE)_2\text{-BB}(A^1B)_n(A^2B)_m(A^1B)_p$, and a mixture of any of the foregoing, wherein A is the repeat unit $\{M^A(ER)(ER)\}$, B is the repeat unit $\{M^B(ER)(ER)\}$, p is one or more, n is one or more, and m is one or more.

An ink comprising one or more compounds above and one or more carriers.

The ink above wherein the ink is a solution of the compounds in an organic carrier.

The ink above wherein the ink is a slurry or suspension of the compounds in an organic carrier.

The ink above further comprising a dopant or alkali dopant.

The ink above further comprising an additional indium-containing compound, an additional gallium-containing compound, or a molybdenum-containing compound.

The ink above further comprising one or more components selected from the group of a surfactant, a dispersant, an emulsifier, an anti-foaming agent, a dryer, a filler, a resin binder, a thickener, a viscosity modifier, an anti-oxidant, a flow agent, a plasticizer, a conductivity agent, a crystallization promoter, an extender, a film conditioner, an adhesion promoter, and a dye.

The ink above further comprising one or more components selected from the group of a conducting polymer, silver metal, silver selenide, silver sulfide, copper metal, indium metal, gallium metal, zinc metal, an alkali metal, an alkali metal salt, an alkaline earth metal salt, a sodium chalcogenate, a calcium chalcogenate, cadmium sulfide, cadmium selenide, cadmium telluride, indium sulfide, indium selenide, indium telluride, gallium sulfide, gallium selenide, gallium telluride, zinc sulfide, zinc selenide, zinc telluride, copper sulfide, copper selenide, copper telluride, molybdenum sulfide, molybdenum selenide, molybdenum telluride, and mixtures of any of the foregoing.

A method for making a precursor compound comprising:
a) providing monomer compounds $M^{B1}(ER)_3$, $M^{B2}(ER)_3$, $M^{A1}(ER)$ and $M^{A2}(ER)$; and
b) contacting the monomer compounds;
wherein $M^{B1}$ is In, $M^{B2}$ is Ga, $M^{A1}$ is Cu, and $M^{A2}$ is Ag, each E is S, Se, or Te, and each R is independently selected, for each occurrence, from alkyl, aryl, heteroaryl, alkenyl, amido, silyl, and inorganic and organic ligands.

The method above wherein $M^{B1}$ and $M^{B2}$ are both In, or $M^{B1}$ and $M^{B2}$ are both Ga.

The method above wherein $M^{A1}$ and $M^{A2}$ are both Ag.

The method above wherein $M^{A1}$ and $M^{A2}$ are both Ag, and $M^{B1}$ and $M^{B2}$ are both In or $M^{B1}$ and $M^{B2}$ are both Ga.

The method above wherein the compound is a CAIGS, AIGS, CAIS, CAGS, AIS, or AGS precursor compound.

A compound made by a process comprising reacting monomers $M^{B1}(ER)_3$, $M^{B2}(ER)_3$, $M^{A1}(ER)$ and $M^{A2}(ER)$, wherein $M^{B1}$ is In, $M^{B2}$ is Ga, $M^{A1}$ is Cu, and $M^{A2}$ is Ag, each E is S, Se, or Te, and each R is independently selected, for each occurrence, from alkyl, aryl, heteroaryl, alkenyl, amido, silyl, and inorganic and organic ligands.

An article comprising one or more compounds or inks above deposited onto a substrate.

The article above wherein the depositing is done by spraying, spray coating, spray deposition, spray pyrolysis, printing, screen printing, inkjet printing, aerosol jet printing, ink printing, jet printing, stamp/pad printing, transfer printing, pad printing, flexographic printing, gravure printing, contact printing, reverse printing, thermal printing, lithography, electrophotographic printing, electrodepositing, electroplating, electroless plating, bath deposition, coating, dip coating, wet coating, spin coating, knife coating, roller coating, rod coating, slot die coating, meyerbar coating, lip direct coating, capillary coating, liquid deposition, solution deposition, layer-by-layer deposition, spin casting, solution casting, and combinations of any of the forgoing.

The article above wherein the substrate is selected from the group of a semiconductor, a doped semiconductor, silicon, gallium arsenide, insulators, glass, molybdenum glass, silicon dioxide, titanium dioxide, zinc oxide, silicon nitride, a metal, a metal foil, molybdenum, aluminum, beryllium, cadmium, cerium, chromium, cobalt, copper, gallium, gold, lead, manganese, molybdenum, nickel, palladium, platinum, rhenium, rhodium, silver, stainless steel, steel, iron, strontium, tin, titanium, tungsten, zinc, zirconium, a metal alloy, a metal silicide, a metal carbide, a polymer, a plastic, a conductive polymer, a copolymer, a polymer blend, a polyethylene terephthalate, a polycarbonate, a polyester, a polyester film, a mylar, a polyvinyl fluoride, polyvinylidene fluoride, a polyethylene, a polyetherimide, a polyethersulfone, a polyetherketone, a polyimide, a polyvinylchloride, an acrylonitrile butadiene styrene polymer, a silicone, an epoxy, paper, coated paper, and combinations of any of the forgoing.

The article above wherein the substrate is a shaped substrate including a tube, a cylinder, a roller, a rod, a pin, a shaft, a plane, a plate, a blade, a vane, a curved surface or a spheroid.

A method for making an article, the method comprising:
(a) providing one or more compounds or inks above;
(b) providing a substrate; and
(c) depositing the compounds or inks onto the substrate.

The method above wherein step (c) is repeated.

The method above further comprising heating the substrate at a temperature of from about 100° C. to about 400° C. to convert the compounds or inks to a material.

The method above further comprising heating the substrate at a temperature of from about 100° C. to about 400° C. to convert the compounds or inks to a material, followed by repeating step (c).

The method above further comprising annealing the material by heating the substrate at a temperature of from about 300° C. to about 650° C.

The method above further comprising heating the substrate at a temperature of from about 100° C. to about 400° C. to convert the compounds or inks to a material, and annealing the material by heating the substrate at a temperature of from about 300° C. to about 650° C.

The method above further comprising heating the substrate at a temperature of from about 100° C. to about 400° C. to convert the compounds or inks to a material, depositing the compounds or inks onto the substrate, and annealing the material by heating the substrate at a temperature of from about 300° C. to about 650° C.

The method above further comprising:
(d) heating the substrate at a temperature of from about 100° C. to about 400° C. to convert the compounds or inks to a material;
(e) depositing the compounds or inks onto the substrate;
(f) repeating steps (d) and (e); and
(g) annealing the material by heating the substrate at a temperature of from about 300° C. to about 650° C.

The method above further comprising:
(d) heating the substrate at a temperature of from about 100° C. to about 400° C. to convert the compounds or inks to a material;
(e) annealing the material by heating the substrate at a temperature of from about 300° C. to about 650° C.; and
(f) repeating steps (c), (d) and (e).

The method above further comprising an optional step of selenization or sulfurization, either before, during or after any step of heating or annealing.

An article made by the method above.

A photovoltaic device made by the method above.

A material having the empirical formula $(Cu_{1-x}Ag_x)_u(In_{1-y}Ga_y)_v(S_{1-z}Se_z)_w$, where x is from 0.001 to 1, y is from 0 to 1, z is from 0 to 1, u is from 0.5 to 1.5, v is from 0.5 to 1.5, and w is from 1 to 3.

The material above wherein x is from 0.001 to 0.3, y is from 0 to 1, z is from 0.5 to 1, u is from 0.7 to 1.1, v is from 0.9 to 1.1, and w is from 1.8 to 2.4.

The material above wherein x is from 0.3 to 0.6, y is from 0 to 1, z is from 0.5 to 1, u is from 0.7 to 1.1, v is from 0.9 to 1.1, and w is from 1.8 to 2.4.

The material above wherein x is from 0.6 to 1, y is from 0 to 1, z is from 0.5 to 1, u is from 0.7 to 1.1, v is from 0.9 to 1.1, and w is from 1.8 to 2.4.

The material above wherein the material is a semiconductor.

The material above wherein the material is in the form of a thin film.

An optoelectronic device comprising the material above.

A method for making a material comprising,
(a) providing one or more compounds or inks above;
(b) providing a substrate;
(c) depositing the compounds or inks onto the substrate; and
(d) heating the substrate at a temperature of from about 20° C. to about 650° C. in an inert atmosphere, thereby producing a material.

A thin film material made by a process comprising,
(a) providing one or more compounds or inks above;
(b) providing a substrate;
(c) depositing the compounds or inks onto the substrate; and
(d) heating the substrate at a temperature of from about 20° C. to about 650° C. in an inert atmosphere, thereby producing a thin film material having a thickness of from 0.05 to 10 micrometers.

A photovoltaic absorber having the empirical formula $(Cu_{1-x}Ag_x)_u(In_{1-y}Ga_y)_v(S_{1-z}Se_z)_w$, where x is from 0.001 to 1, y is from 0 to 1, z is from 0 to 1, u is from 0.5 to 1.5, v is from 0.5 to 1.5, and w is from 1 to 3.

The photovoltaic absorber above wherein x is from 0.001 to 0.7, y is from 0 to 1, z is from 0.5 to 1, u is from 0.7 to 1.1, v is from 0.9 to 1.1, and w is from 1.5 to 2.5.

The photovoltaic absorber above wherein x is from 0.001 to 0.5, y is from 0 to 1, z is from 0.5 to 1, u is from 0.7 to 1.1, v is from 0.9 to 1.1, and w is from 1.5 to 2.5.

The photovoltaic absorber above wherein x is from 0.001 to 0.3, y is from 0 to 1, z is from 0.5 to 1, u is from 0.7 to 1.1, v is from 0.9 to 1.1, and w is from 1.5 to 2.5.

A photovoltaic device comprising the photovoltaic absorber above.

A system for providing electrical power comprising a photovoltaic device above.

A method for providing electrical power comprising using a photovoltaic system above to convert light into electrical energy.

A method for making a photovoltaic absorber layer on a substrate comprising,
(a) providing one or more compounds or inks above;
(b) providing a substrate;
(c) depositing the compounds or inks onto the substrate; and
(d) heating the substrate at a temperature of from about 100° C. to about 650° C. in an inert atmosphere, thereby producing a photovoltaic absorber layer having a thickness of from 0.001 to 100 micrometers.

Empirical Formulas of Precursor Compounds

This disclosure provides a range of polymeric precursor compounds having two or more different metal atoms and chalcogen atoms.

In certain aspects, a polymeric precursor compound contains metal atoms, and atoms of Group 13, as well as combinations thereof. Any of these atoms may be bonded to one or more atoms selected from atoms of Group 15, S, Se, and Te, as well as one or more ligands.

A polymeric precursor compound may be a neutral compound, or an ionic form, or have a charged complex or counterion. In some embodiments, an ionic form of a polymeric precursor compound may contain a divalent metal atom, or a divalent metal atom as a counterion.

A polymeric precursor compound may contain atoms selected from the transition metals of Group 3 through Group 12, B, Al, Ga, In, Tl, Si, Ge, Sn, Pb, As, Sb, and Bi. Any of these atoms may be bonded to one or more atoms selected from atoms of Group 15, S, Se, and Te, as well as one or more ligands.

A polymeric precursor compound may contain atoms selected from Ni, Pd, Pt, Cu, Ag, Au, Zn, Cd, Hg, B, Al, Ga, In, Tl, Si, Ge, Sn, Pb, and Bi. Any of these atoms may be bonded to one or more atoms selected from atoms of Group 15, S, Se, and Te, as well as one or more ligands.

In some embodiments, a polymeric precursor compound may contain atoms selected from Cu, Zn, Ga, In, Tl, Si, Ge, Sn, and Pb. Any of these atoms may be bonded to one or more atoms selected from atoms of Group 15, S, Se, and Te, as well as one or more ligands.

In some embodiments, a polymeric precursor compound may contain atoms selected from Cu, Zn, Ga, In, Tl, Si, Ge, Sn, and Pb. Any of these atoms may be bonded to one or more chalcogen atoms, as well as one or more ligands.

In some variations, a polymeric precursor compound may contain atoms selected from Ag, Cu, Ga, and In. Any of these atoms may be bonded to one or more atoms selected from S, Se, and Te, as well as one or more ligands.

Polymeric Precursor Structure and Properties (MPP)

A polymeric precursor compound of this disclosure is stable at ambient temperatures. Polymeric precursors can be used for making layered materials, optoelectronic materials, and devices. Using polymeric precursors advantageously allows control of the stoichiometry, structure, and ratios of various atoms in a material, layer, or semiconductor.

Polymeric precursor compounds of this invention may be solids, solids with low melting temperatures, semisolids, flowable solids, gums, or rubber-like solids, oily substances, or liquids at ambient temperatures, or temperatures moderately elevated from ambient. Embodiments of this disclosure that are fluids at temperatures moderately elevated from ambient can provide superior processability for production of solar cells and other products, as well as the enhanced ability to be processed on a variety of substrates including flexible substrates.

In general, a polymeric precursor compound can be processed through the application of heat, light, kinetic, mechanical or other energy to be converted to a material, including a semiconductor material. In these processes, a polymeric precursor compound undergoes a transition to become a material. The conversion of a polymeric precursor compound to a material can be done in processes known in the art, as well as the novel processes of this disclosure.

Embodiments of this invention may further provide processes for making optoelectronic materials. Following the synthesis of a polymeric precursor compound, the compound can be deposited, sprayed, or printed onto a substrate by various means. Conversion of the polymeric precursor compound to a material can be done during or after the process of depositing, spraying, or printing the compound onto the substrate.

A polymeric precursor compound of this disclosure may have a transition temperature below about 400° C., or below about 300° C., or below about 280° C., or below about 260° C., or below about 240° C., or below about 220° C., or below about 200° C.

In some aspects, polymeric precursors of this disclosure include molecules that are melt processable at temperatures below about 100° C. In certain aspects, a polymeric precursor can be fluid, flowable, flowable melt, or semisolid at relatively low temperatures and can be processed as a neat solid, semisolid, neat flowable melt, flowable solid, gum, rubber-like solid, oily substance, or liquid. In certain embodiments, a polymeric precursor is melt processable as a flowable melt at a temperature below about 200° C., or below about 180° C., or below about 160° C., or below about 140° C., or below about 120° C., or below about 100° C., or below about 80° C., or below about 60° C., or below about 40° C.

A polymeric precursor compound of this invention can be crystalline or amorphous, and can be soluble in various non-aqueous solvents.

A polymeric precursor compound may contain ligands, or ligand fragments, or portions of ligands that can be removed under mild conditions, at relatively low temperatures, and therefore provide a facile route to convert the polymeric precursor to a material or semiconductor. The ligands, or some atoms of the ligands, may be removable in various processes, including certain methods for depositing, spraying, and printing, as well as by application of energy.

These advantageous features allow enhanced control over the compositional structure of a semiconductor material made with the polymeric precursor compounds of this invention.

Polymeric Precursors for Semiconductors and Optoelectronics (MPP-CAIGS)

This invention provides a range of polymeric precursor structures, compositions, and molecules having two or more different metal atoms.

In some embodiments, a polymeric precursor compound contains atoms $M^B$ of Group 13 selected from Ga, In, and a combination thereof.

These polymeric precursor compounds further contain monovalent metal atoms $M^A$ selected from Cu, Ag, and a mixture thereof. The atoms $M^A$ may be any combination of atoms of Cu and Ag.

The polymeric precursors of this disclosure can be considered inorganic polymers or coordination polymers.

The polymeric precursors of this disclosure may be represented in different ways, using different formulas to describe the same structure.

In some aspects, a polymeric precursor of this disclosure may be a distribution of polymer molecules or chains. The distribution may encompass molecules or chains having a range of chain lengths or molecular sizes. A polymeric precursor can be a mixture of polymers, polymer molecules or chains. The distribution of a polymeric precursor can be centered or weighted about a particular molecular weight or chain mass.

Embodiments of this invention further provide polymeric precursors that can be described as AB alternating addition copolymers.

The AB alternating addition copolymer is in general composed of repeat units A and B. The repeat units A and B are each derived from a monomer. The repeat units A and B may also be referred to as being monomers, although the empirical formula of monomer A is different from the empirical formula of repeat unit A.

The monomer for $M^A$ can be $M^A(ER)$, where $M^A$ is Cu or Ag. In certain embodiments, $M^A$ is Ag.

The monomer for $M^B$ can be $M^B(ER)_3$, where $M^B$ is Ga, In, or a mixture of Ga and In.

In a polymeric precursor, monomers of A link to monomers of B to provide a polymer chain, whether linear, cyclic, or branched, or of any other shape, that has repeat units A, each having the formula $\{M^A(ER)_2\}$, and repeat units B, each having the formula $\{M^B(ER)_2\}$. The repeat units A and B may appear in alternating order in the chain, for example, •••ABABABAB•••.

In some aspects, a polymeric precursor may have atoms $M^B$ in the structure, where $M^B$ is Ga or In in random order.

The polymeric precursor compounds of this invention may be made with any desired stoichiometry with respect to the number of different metal atoms and Group 13 elements and their respective ratios. The stoichiometry of a polymeric precursor compound may be controlled through the concentrations of monomers, or repeating units in the polymer chains of the precursors.

In some aspects, this disclosure provides polymeric precursors which are inorganic AB alternating addition copolymers having one of the following Formulas 1 through 13:

| | |
|---|---|
| $(RE)_2\text{-}[B(AB)_n]^-$ | Formula 1 |
| $(RE)_2\text{-}[(BA)_nB]^-$ | Formula 2 |
| $(RE)_2\text{-}BB(AB)_n$ | Formula 3 |
| $(RE)_2\text{-}B(AB)_nB$ | Formula 4 |
| $(RE)_2\text{-}B(AB)_nB(AB)_m$ | Formula 5 |
| $(RE)_2\text{-}(BA)_nBB$ | Formula 6 |
| $(RE)_2\text{-}B(BA)_nB$ | Formula 7 |
| $(RE)_2\text{-}(BA)_nB(BA)_mB$ | Formula 8 |
| $^{cyclic}(AB)_n$ | Formula 9 |
| $^{cyclic}(BA)_n$ | Formula 10 |
| $(RE)_2\text{-}(BB)(AABB)_n$ | Formula 11 |
| $(RE)_2\text{-}(BB)(AABB)_n(AB)_m$ | Formula 12 |
| $(RE)_2\text{-}(B)(AABB)_n(B)(AB)_m$ | Formula 13 | where A and B are as defined above, E is S, Se, or Te, and R is defined below.

Formulas 1 and 2 describe ionic forms that have a counterion or counterions not shown. Examples of counterions include alkali metal ions, Na, Li, and K.

The formulas $RE\text{-}B(AB)_n$ and $RE\text{-}(BA)_nB$ may describe stable molecules under certain conditions.

For example, an embodiment of a polymeric precursor compound of Formula 4 is shown in FIG. 1. As shown in FIG. 1, the structure of the compound can be represented by the formula $(RE)_2BABABB$, wherein A is the repeat unit $\{M^A(ER)_2\}$, B is the repeat unit $\{M^B(ER)_2\}$, E is a chalcogen, and R is a functional group defined below.

Figure 2:
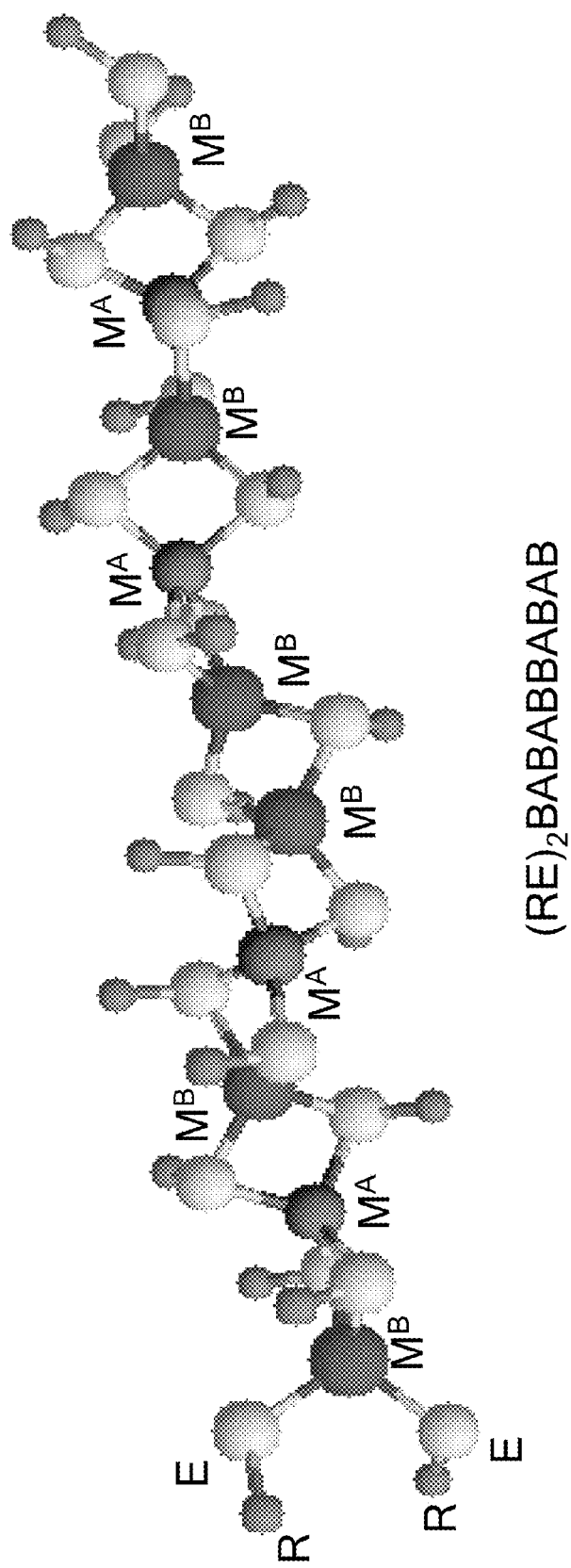
FIG. 2 shows an embodiment of a polymeric precursor compound (MPP-CAIGS).

In another example, an embodiment of a polymeric precursor compound of Formula 5 is shown in FIG. 2. As shown in FIG. 2, the structure of the compound can be represented by the formula $(RE)_2BABABBABAB$, wherein A is the repeat unit $\{M^A(ER)_2\}$, B is the repeat unit $\{M^B(ER)_2\}$, E is a chalcogen, and R is a functional group defined below.

Figure 3:
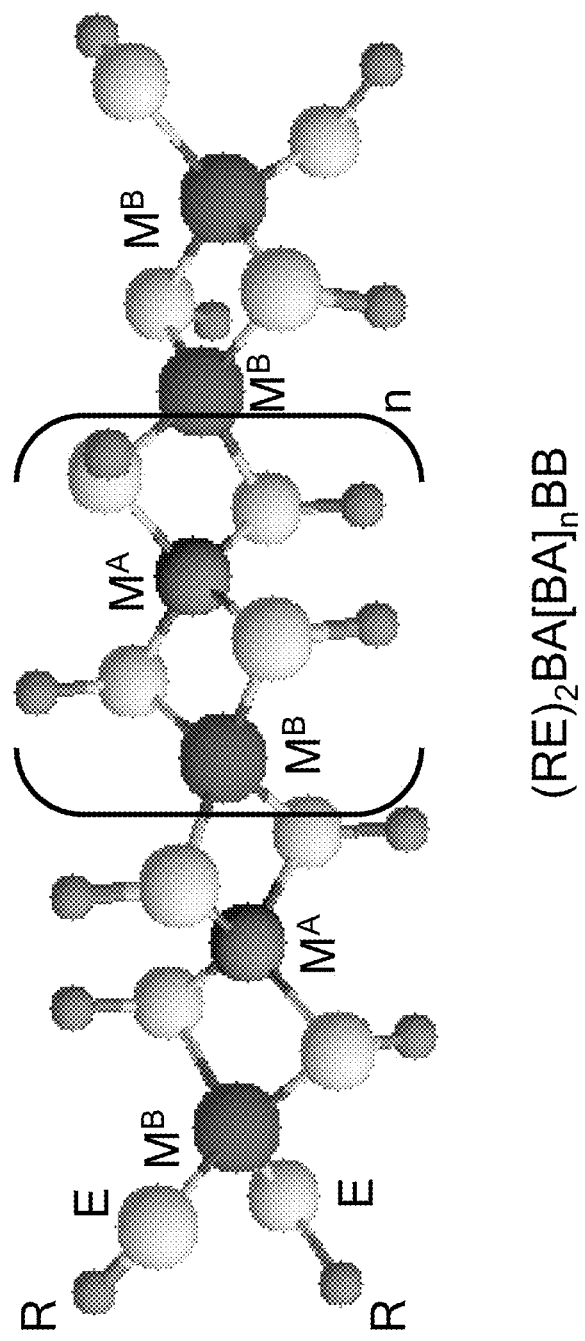
FIG. 3 shows an embodiment of a polymeric precursor compound (MPP-CAIGS).

In a further example, an embodiment of a polymeric precursor compound of Formula 6 is shown in FIG. 3. As shown in FIG. 3, the structure of the compound can be represented by the formula $(RE)_2BA(BA)_nBB$, wherein A is the repeat unit $\{M^A(ER)_2\}$, B is the repeat unit $\{M^B(ER)_2\}$, E is a chalcogen, and R is a functional group defined below.

Figure 4:
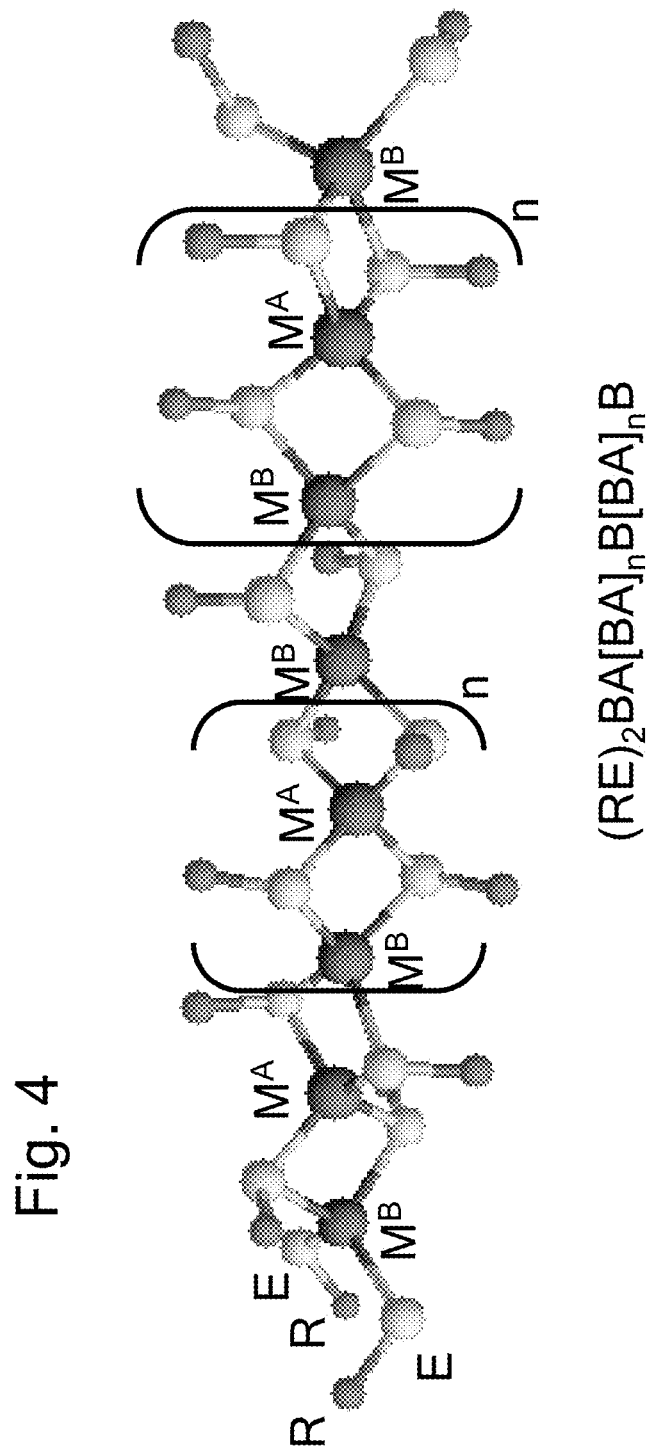
FIG. 4 shows an embodiment of a polymeric precursor compound (MPP-CAIGS).

In another example, an embodiment of a polymeric precursor compound of Formula 8 is shown in FIG. 4. As shown in FIG. 4, the structure of the compound can be represented by the formula $(RE)_2BA(BA)_n B(BA)_mB$, wherein A is the repeat unit $\{M^A(ER)_2\}$, B is the repeat unit $\{M^B(ER)_2\}$, E is a chalcogen, and R is a functional group defined below.

Figure 5:
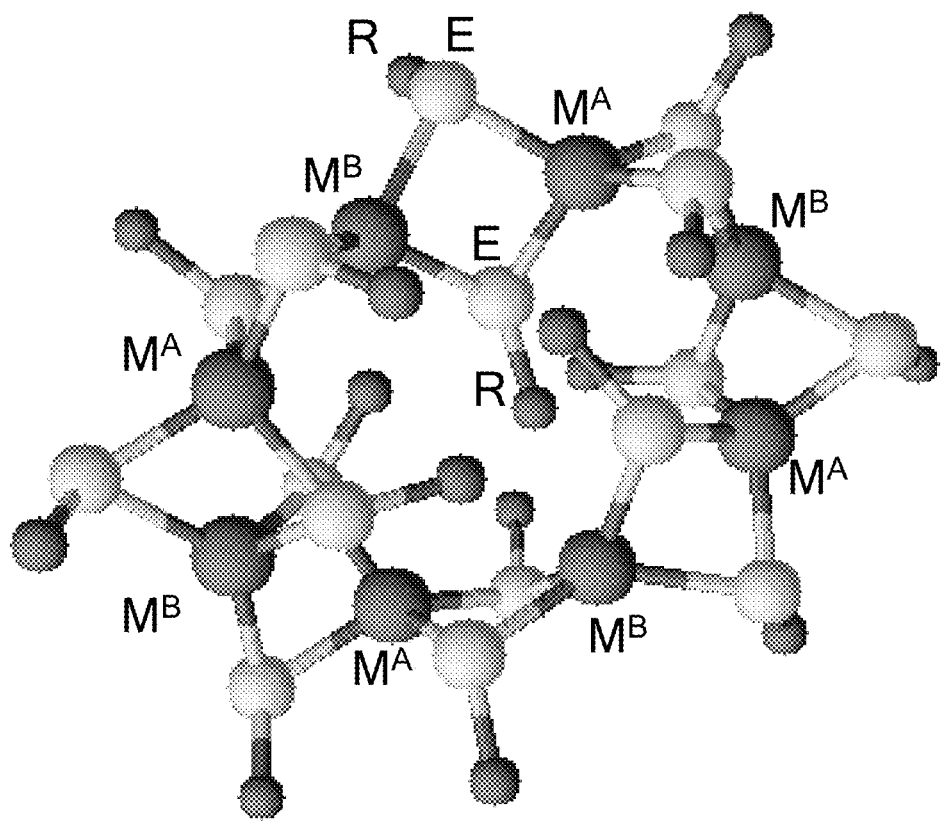
FIG. 5 shows an embodiment of a polymeric precursor compound (MPP-CAIGS).

In a further example, an embodiment of a polymeric precursor compound of Formula 10 is shown in FIG. 5. As shown in FIG. 5, the structure of the compound can be represented by the formula $^{cyclic}(BA)_4$, wherein A is the repeat unit $\{M^A(ER)_2\}$, B is the repeat unit $\{M^B(ER)_2\}$, E is a chalcogen, and R is a functional group defined below.

A polymeric precursor having one of Formulas 1-8 and 11-13 may be of any length or molecular size. The values of n and m can be one (1) or more. In certain embodiments, the values of n and m are 2 or more, or 3 or more, or 4 or more, or 5 or more, or 6 or more, or 7 or more, or 8 or more, or 9 or more, or 10 or more. In some embodiments, n and m are independently from 2 to about one million, or from 2 to about 100,000, or from 2 to about 10,000, or from 2 to about 5000, or from 2 to about 1000, or from 2 to about 500, or from 2 to about 100, or from 2 to about 50.

A cyclic polymeric precursor having one of Formulas 9 or 10 may be of any molecular size. The value of n may be two (2) or more. In certain variations, the values of n and m are 2 or more, or 3 or more, or 4 or more, or 5 or more, or 6 or more, or 7 or more, or 8 or more, or 9 or more, or 10 or more. In some embodiments, for cyclic Formulas 9 and 10, n is from 2 to about 50, or from 2 to about 20, or from 2 to about 16, or from 2 to about 14, or from 2 to about 12, or from 2 to about 10, or from 2 to about 8.

In another aspect, the repeat units $\{M^B(ER)_2\}$ and $\{M^A(ER)_2\}$ may be considered "handed" because the metal atom $M^A$ and the Group 13 atom $M^B$ appear on the left, while the chalcogen atom E appears to the right side. Thus, a linear terminated chain will in general require an additional chalcogen group or groups on the left terminus, as in Formulas 1-8 and 11-13, to complete the structure. A cyclic chain, as described by Formulas 9 and 10, does not require an additional chalcogen group or groups for termination.

In certain aspects, structures of Formulas 1-8 and 11-13, where n and m are one (1), may be described as adducts. For example, adducts include $(RE)_2$-BBAB, $(RE)_2$-BABB, and $(RE)_2$-BABBAB.

In some embodiments, a polymeric precursor may include a structure that is an AABB alternating block copolymer. For example, a polymeric precursor or portions of a precursor structure may contain one or more consecutive repeat units {AABB}. A polymeric precursor having an AABB alternating block copolymer may be represented by Formula 11 above.

In some aspects, this disclosure provides polymeric precursors which are inorganic AB alternating addition copolymers having the repeat units of Formula 14

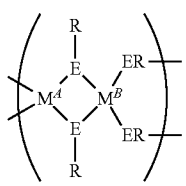

Formula 14 where atoms $M^B$ are Ga or In, and each E is S, Se, or Te.

In certain aspects, this invention provides polymeric precursors having a number n of the repeat units of Formula 14, where n may be 1 or more, or 2 or more, or 3 or more, or 4 or more, or 5 or more, or 6 or more, or 7 or more, or 8 or more, or 9 or more, or 10 or more, or 11 or more, or 12 or more.

The AB copolymer of Formula 14 may also be represented as $(AB)_n$ or $(BA)_n$, which represents a polymer of any chain length. Another way to represent certain AB copolymers is the formula •••ABAB•••.

In further variations, this invention provides polymeric precursors that may be represented by Formula 15

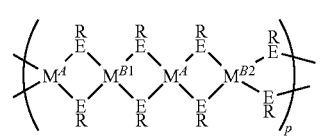

Formula 15 where atoms $M^{B1}$ and $M^{B2}$ are the same or different atoms of Group 13 selected from Ga, and In, each E is S, Se, or Te, and p is one (1) or more.

In further aspects, this invention provides polymeric precursors which may be represented by Formula 16

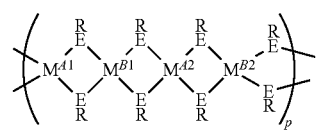

Formula 16 where atoms $M^{B1}$ and $M^{B2}$ are the same or different atoms of Group 13 selected from Ga and In, atoms $M^{A1}$ and $M^{A2}$ are the same or different and are atoms selected from Cu and Ag, each E is S, Se, or Te, and p is one (1) or more.

In another aspect, this disclosure provides inorganic AB alternating copolymers which may be represented by Formula 17

•••••AB$^1$AB$^2$AB$^3$•••••      Formula 17 where B$^1$, B$^2$, and B$^3$ are repeat units containing atoms $M^{B1}$, $M^{B2}$, and $M^{B3}$, respectively, which are atoms of Ga and In.

Some examples of empirical formulas for monomers and polymeric precursors of this invention are summarized in Table 1.

TABLE 1

Empirical formulas for monomers, repeat units and polymeric precursors

| Formula | Representative Constitutional Chain Unit | Description |
|---|---|---|
| A | $\{M^A(ER)_2\}$ | From monomer $M^A(ER)$, where M is Cu or Ag |

TABLE 1-continued

Empirical formulas for monomers, repeat units and polymeric precursors

| Formula | Representative Constitutional Chain Unit | Description |
|---|---|---|
| B | $\{M^B(ER)_2\}$ | From monomer $M^B(ER)_3$, where $M^B$ is Ga, In |
| AB | $\{M^A(ER)_2 M^B(ER)_2\}$ | Polymer chain repeat unit |
| ABA | $\{M^A(ER)_2 M^B(ER)_2 M^A(ER)_2\}$ | An adduct trimer, or oligomer |
| $B^1 A B^2$ | $\{M^{B1}(ER)_2 M^A(ER)_2 M^{B2}(ER)_2\}$ | Polymer chain repeat unit, $M^{B1}$ and $M^{B2}$ may be the same or different, a trimer or oligomer |
| $AB^1 AB^2$ | $\{M^A(ER)_2 M^{B1}(ER)_2 M^A(ER)_2 M^{B2}(ER)_2\}$ | Alternating copolymer $(AB)_n$, a tetramer or oligomer |
| $AB^1 AB^2 AB^3$ | $\{M^A(ER)_2 M^{B1}(ER)_2 M^A(ER)_2 M^{B2}(ER)_2 M^A(ER)_2 M^{B1}(ER)_2\}$ | Polymer, or an AB trimer, or an oligomer |
| $(AB)_n$ or $(BA)_n$ | $\dashv A\text{—}B\dashv_n$ or $\dashv B\text{—}A\dashv_n$ | Polymer of any chain length |
| •••ABAB••• | $\dashv A\text{—}B\text{—}A\text{—}B\dashv$ | Polymer of any length, whether linear, branched, or cyclic |
| {AABB} | $\dashv A\text{—}A\text{—}B\text{—}B\dashv$ | AABB alternating block copolymer |
| $^{cyclic}(AB)_4$ or $^{cyclic}(BA)_4$ | 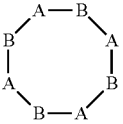 | Cyclic polymer chain, oligomer or octamer |

In Table 1, the "representative constitutional chain unit" refers to the repeating unit of the polymer chain. In general, the number and appearance of electrons, ligands, or R groups in a representative constitutional chain repeating unit does not necessarily reflect the oxidation state of the metal atom. For example, the chain repeating unit A, which is $\{M^A(ER)_2\}$, arises from the monomer $M^A(ER)$, where $M^A$ is a metal atom of monovalent oxidation state 1 (I or one) selected from Cu and Ag. It is to be understood that the repeating unit exists in the polymer chain bonded to two other repeating units, or to a repeating unit and a chain terminating unit. Likewise, the chain repeating unit B, which is $\{M^B(ER)_2\}$, arises from the monomer $M^B(ER)_3$, where $M^B$ is a Group 13 atom of trivalent oxidation state 3 (III or three) selected from Ga, In, and a mixture thereof. In one aspect, monomer $M^A(ER)$, and monomer $M^B(ER)_3$, combine to form an AB repeating unit, which is $\{M^A(ER)_2 M^B(ER)_2\}$.

In some aspects, this disclosure provides AB alternating copolymers which may also be alternating with respect to $M^A$ or $M^B$. A polymeric precursor that is alternating with respect to $M^A$ may contain chain regions having alternating atoms $M^{A1}$ and $M^{A2}$. A polymeric precursor that is alternating with respect to $M^B$ may contain chain regions having alternating atoms $M^{B1}$ and $M^{B2}$.

In further aspects, this disclosure provides AB alternating block copolymers which may contain one or more blocks of n repeat units, represented as $(AB^1)_n$ or $(B^1A)_n$, where the block of repeat units contains only one kind of atom $M^{B1}$ selected from Group 13. A block may also be a repeat unit represented as $(A^1B)_n$ or $(BA^1)_n$, where the block of repeat units contains only one kind of atom $M^{A1}$. A polymeric precursor of this disclosure may contain one or more blocks of repeat units having different Group 13 atoms in each block, or different atoms $M^A$ in each block. For example, a polymeric precursor may have one of the following formulas:

| | |
|---|---|
| $(RE)_2\text{-BB}(AB^1)_n(AB^2)_m$ | Formula 18 |
| $(RE)_2\text{-BB}(AB^1)_n(AB^2)_m(AB^1)_p$ | Formula 19 |
| $(RE)_2\text{-BB}(AB^1)_n(AB^2)_m(AB^1)_p$ | Formula 20 |
| $(RE)_2\text{-BB}(A^1B)_n(A^2B)_m$ | Formula 21 |
| $(RE)_2\text{-BB}(A^1B)_n(A^2B)_m(A^1B)_p$ | Formula 22 | where $B^1$, $B^2$ represent repeat units $\{M^{B1}(ER)_2\}$ and $\{M^{B2}(ER)_2\}$ respectively, where $M^{B1}$, $M^{B2}$ are In, Ga, respectively, and where $A^1$, $A^2$ represent repeat units $\{M^{A1}(ER)_2\}$ and $\{M^{A2}(ER)^2\}$ respectively, where $M^{A1}$, $M^{A2}$ are Cu and Ag, respectively. In Formulas 18 through 22, the values of n, m, and p may be 2 or more, or 3 or more, or 4 or more, or 5 or more, or 6 or more, or 7 or more, or 8 or more, or 9 or more, or 10 or more, or 11 or more, or 12 or more.

In certain embodiments, an $M^B$ monomer can contain a chelating group -ERE-, for example, having the formula $M^B(ERE)$.

In some embodiments, a monomer may exist in a dimeric form under ambient conditions, or a trimeric or higher form, and can be used as a reagent in such forms. It is understood that the term monomer would refer to all such forms, whether found under ambient conditions, or found during the process for synthesizing a polymeric precursor from the monomer. The formulas $M^A(ER)$ and $M^B(ER)_3$, for example, should be taken to encompass the monomer in such naturally-occurring dimeric or higher forms, if any. A monomer in a dimeric or higher form, when used as a reagent can provide the monomer form. For example, compounds of the empirical formula Cu(ER) may occur in aggregated forms that are insoluble, and when used as a reagent can provide the monomer form for reaction with $M^B(ER)_3$.

The polymeric precursors of this invention obtained by reacting monomers $M^A(ER)$ and $M^B(ER)_3$ can be advantageously highly soluble in organic solvent, whereas one or more of the monomers may have been insoluble.

As used herein, the terms "polymer" and "polymeric" refer to a polymerized moiety, a polymerized monomer, a repeating chain made of repeating units, or a polymer chain or polymer molecule. A polymer or polymer chain may be defined by recitation of its repeating unit or units, and may have various shapes or connectivities such as linear, branched, cyclic, and dendrimeric. Unless otherwise specified, the terms polymer and polymeric include homopolymers, copolymers, block copolymers, alternating polymers, terpolymers, polymers containing any number of different monomers, oligomers, networks, two-dimensional networks, three-dimensional networks, crosslinked polymers, short and long chains, high and low molecular weight polymer chains, macromolecules, and other forms of repeating structures such as dendrimers. Polymers include those having linear, branched and cyclic polymer chains, and polymers having long or short branches.

As used herein, the term "polymeric component" refers to a component of a composition, where the component is a polymer, or may form a polymer by polymerization. The term polymeric component includes a polymerizable monomer or polymerizable molecule. A polymeric component may have any combination of the monomers or polymers which make up any of the example polymers described herein, or may be a blend of polymers.

Embodiments of this invention may further provide polymeric precursors having polymer chain structures with repeating units. The stoichiometry of these polymeric precursors may be precisely controlled to provide accurate levels of any desired arbitrary ratio of particular atoms. Precursor compounds having controlled stoichiometry can be used to make bulk materials, layers, and semiconductor materials having controlled stoichiometry. In some aspects, precisely controlling the stoichiometry of a polymeric precursor may be achieved by controlling the stoichiometry of the reagents, reactants, monomers or compounds used to prepare the polymeric precursor.

For the polymeric precursors of this invention, the group R in the formulas above, or a portion thereof, may be a good leaving group in relation to a transition of the polymeric precursor compound at elevated temperatures or upon application of energy.

The functional groups R in the formulas above and in Table 1 may each be the same or different from the other and are groups attached through a carbon or non-carbon atom, including alkyl, aryl, heteroaryl, alkenyl, amido, silyl, and inorganic and organic ligands. In some embodiments, the groups R are each the same or different from the other and are alkyl groups attached through a carbon atom.

In some aspects, the monomer for $M^B$ can be represented as $M^B(ER^1)_3$, and the monomer for $M^A$ can be represented as $M^A(ER^2)$, where $R^1$ and $R^2$ are the same or different and are groups attached through a carbon or non-carbon atom, including alkyl, aryl, heteroaryl, alkenyl, amido, silyl, and inorganic and organic ligands. In some embodiments, the groups $R^1$ and $R^2$ are each the same or different from the other and are alkyl groups attached through a carbon atom.

In certain variations, the monomer for $M^B$ may be $M^B(ER^1)(ER^3)_2$, where $R^1$ and $R^3$ are different and are groups attached through a carbon or non-carbon atom, including alkyl, aryl, heteroaryl, alkenyl, amido, silyl, and inorganic and organic ligands. In some embodiments, the groups $R^1$ and $R^3$, of $M^B(ER^1)(ER^3)_2$, are different and are alkyl groups attached through a carbon atom.

In some embodiments, polymeric precursor compounds advantageously do not contain a phosphine ligand, or a ligand or attached compound containing phosphorus, arsenic, or antimony, or a halogen ligand.

In further embodiments, the groups R may independently be (C1-22)alkyl groups. In these embodiments, the alkyl group may be a (C1)alkyl (methyl), or a (C2)alkyl (ethyl), or a (C3)alkyl, or a (C4)alkyl, or a (C5)alkyl, or a (C6)alkyl, or a (C7)alkyl, or a (C8)alkyl, or a (C9)alkyl, or a (C10)alkyl, or a (C11)alkyl, or a (C12)alkyl, or a (C13)alkyl, or a (C14)alkyl, or a (C15)alkyl, or a (C16)alkyl, or a (C17)alkyl, or a (C18)alkyl, or a (C19)alkyl, or a (C20)alkyl, or a (C21)alkyl, or a (C22)alkyl.

In certain embodiments, the groups R may independently be (C1-12)alkyl groups. In these embodiments, the alkyl group may be a (C1)alkyl (methyl), or a (C2)alkyl (ethyl), or a (C3)alkyl, or a (C4)alkyl, or a (C5)alkyl, or a (C6)alkyl, or a (C7)alkyl, or a (C8)alkyl, or a (C9)alkyl, or a (C10)alkyl, or a (C11)alkyl, or a (C12)alkyl.

In certain embodiments, the groups R may independently be (C1-6)alkyl groups. In these embodiments, the alkyl group may be a (C1)alkyl (methyl), or a (C2)alkyl (ethyl), or a (C3)alkyl, or a (C4)alkyl, or a (C5)alkyl, or a (C6)alkyl.

A polymeric precursor compound may be crystalline, or non-crystalline.

In some embodiments, a polymeric precursor may be a compound comprising repeating units $\{M^B(ER)(ER)\}$ and $\{M^A(ER)(ER)\}$, wherein $M^A$ is a monovalent metal atom selected from Cu and Ag, $M^B$ is an atom of Group 13, E is S, Se, or Te, and R is independently selected, for each occurrence, from alkyl, aryl, heteroaryl, alkenyl, amido, silyl, and inorganic and organic ligands. In certain embodiments, the atoms $M^B$ in the repeating units $\{M^B(ER)(ER)\}$ are randomly selected from atoms of Group 13. In certain variations, $M^A$ is Ag and the atoms $M^B$ are selected from indium and gallium. E may be only selenium in a polymeric precursor, and the groups R may be independently selected, for each occurrence, from (C1-6)alkyl.

Embodiments of this invention may further provide polymeric precursors that are linear, branched, cyclic, or a mixture of any of the foregoing. Some polymeric precursors may be a flowable melt at a temperature below about 100° C.

In some aspects, a polymeric precursor may contain n repeating units $\{M^B(ER)(ER)\}$ and n repeating units $\{M^A(ER)(ER)\}$, wherein n is one or more, or n is two or more, or n is three or more, or n is four or more, or n is eight or more. The repeating units $\{M^B(ER)(ER)\}$ and $\{M^A(ER)(ER)\}$ may be alternating. A polymeric precursor may be described by the formula $(AB)_n$, wherein A is the repeat unit $\{M^A(ER)(ER)\}$, B is the repeat unit $\{M^B(ER)(ER)\}$, n is one or more, or n is two or more, and R is independently selected, for each occurrence, from alkyl, aryl, heteroaryl, alkenyl, amido, silyl, and inorganic and organic ligands. In some variations, a polymeric precursor may have any one of the formulas $(RE)_2$-BB $(AB)_n$, $(RE)_2$-B$(AB)_n$ B, $(RE)_2$-B$(AB)_n$B$(AB)_m$, $(RE)_2$-$(BA)_n$ BB, $(RE)_2$-B$(BA)_n$B, $(RE)_2$-$(BA)_n$B$(BA)_m$ B, $^{cyclic}(AB)_n$, $^{cyclic}(BA)_n$, $(RE)_2$-(BB)$(AABB)_n$, $(RE)_2$-(BB)$(AABB)_n(AB)_m$, $(RE)_2$-(B)$(AABB)_n(B)(AB)_m$, $(RE)_2$-[B$(AB)_n]^-$, and $(RE)_2$-[$(BA)_nB]^-$, wherein A is the repeat unit $\{M^A(ER)(ER)\}$, B is the repeat unit $\{M^B(ER)(ER)\}$, n is one or more, or n is two or more, or n is three or more, and m is one or more. In further aspects, a polymeric precursor may be a block copolymer containing one or more blocks of repeat units, wherein each block contains only one kind of atom $M^B$.

A precursor compound of this disclosure may be a combination of u*(1−x) equivalents of $M^{A1}$(ER), u*x equivalents of $M^{A2}$(ER), v*(1−y) equivalents of $M^{B1}$(ER)$_3$, v*y equivalents of $M^{B2}$(ER)$_3$, wherein $M^{A1}$ is Cu and $M^{A2}$ is Ag, $M^{B1}$ and $M^{B2}$ are different atoms of Group 13, wherein the compound has the empirical formula $(M^{A1}_{1-x}M^{A2}_{x})_u(M^{B1}_{1-y}M^{B2}_{y})_v((S_{1-z}Se_z)R)_w$, wherein x is from 0 to 1, y is from 0 to 1, z is from 0 to 1, u is from 0.5 to 1.5, v is from 0.5 to 1.5, w is from 2 to 6, and R represents R groups, of which there are w in number, which are independently selected from alkyl, aryl, heteroaryl, alkenyl, amido, silyl, and inorganic and organic ligands. In these embodiments, a precursor compound can have the stoichiometry useful to prepare CAIGS, AIGS, CAIS, CAGS, AIS and AGS materials, including materials deficient or enriched in the quantity of a Group 11 atom. In certain embodiments, $M^{B2}$ is In and y is from 0.65 to 0.85.

A precursor compound of this disclosure may contain a quantity of atoms of Group 11 from 0.33 to 3, or from 0.33 to 0.9, or from 0.33 to 1, or from 1 to 2, or from 1.2 to 2.5, or from 2 to 3, as a ratio of moles of atoms of Group 11 to the total moles of atoms of Group 13, for example as the ratio (Cu plus Ag) to (In plus Ga), or (Cu+Ag):(In +Ga).

In further embodiments, a precursor compound can contain S, Se and Te.

A precursor compound of this disclosure may be a combination of u*(1−x) equivalents of Cu(ER), u*x equivalents of Ag(ER), v*(1−y) equivalents of In(ER)$_3$, v*y equivalents of Ga(ER)$_3$, wherein the compound has the empirical formula $(Cu_{1-x}Ag_x)_u(In_{1-y}Ga_y)_v(S_{1-z}Se_z)_w$, wherein x is from 0 to 1, y is from 0 to 1, z is from 0 to 1, u is from 0.5 to 1.5, v is from 0.5 to 1.5, w is from 2 to 6, and R represents R groups, of which there are w in number, which are independently selected from alkyl, aryl, heteroaryl, alkenyl, amido, silyl, and inorganic and organic ligands.

In some embodiments, a precursor compound can be a combination of w*(1−z) equivalents of $M^{A1}$(ER$^1$), w*z equivalents of $M^{A2}$(ER$^2$), x equivalents of $M^{B1}$(ER$^3$)$_3$, y equivalents of $M^{B1}$(ER$^4$)$_3$, wherein $M^{A1}$ is Cu and $M^{A2}$ is Ag, $M^{B1}$ and $M^{B2}$ are different atoms of Group 13, wherein the compound has the empirical formula $(Cu_{1-z}Ag_z)_wIn_xGa_y(ER^1)_{w(1-z)}(ER^2)_{(w*z)}(ER^3)_{3x}(ER^4)_{3y}$, w is from 0.5 to 1.5, z is from 0 to 1, x is from 0 to 1, y is from 0 to 1, x plus y is one, and wherein R$^1$, R$^2$, R$^3$, R$^4$ are the same or each different, and are independently selected, for each occurrence, from alkyl, aryl, heteroaryl, alkenyl, amido, silyl, and inorganic and organic ligands. In these embodiments, a precursor compound can have the stoichiometry useful to prepare CAIGS, AIGS, CAIS, CAGS, AIS and AGS materials, including materials deficient in the quantity of a Group 11 atom.

In some embodiments, a precursor compound can be a combination of w equivalents of Ag(ER$^2$), x equivalents of In(ER$^3$)$_3$, y equivalents of Ga(ER$^4$)$_3$, wherein the compound has the empirical formula $Ag_wIn_xGa_y(ER^2)_w(ER^3)_{3x}(ER^4)_{3y}$, w is from 0.5 to 1.5, x is from 0 to 1, y is from 0 to 1, x plus y is one, and wherein R$^2$, R$^3$, R$^4$ are the same or each different, and are independently selected, for each occurrence, from alkyl, aryl, heteroaryl, alkenyl, amido, silyl, and inorganic and organic ligands.

This disclosure provides a range of polymeric precursor compounds made by reacting a first monomer $M^B$(ER$^1$)$_3$ with a second monomer $M^A$(ER$^2$), where $M^A$ is a monovalent metal atom selected from Cu and Ag, $M^B$ is an atom of Group 13, each E is S, Se, or Te, and R$^1$ and R$^2$ are the same or different and are independently selected from alkyl, aryl, heteroaryl, alkenyl, amido, silyl, and inorganic and organic ligands. The compounds may contain n repeating units {$M^B$(ER)(ER)} and n repeating units {$M^B$(ER)(ER)}, wherein n is one or more, or n is two or more, and R is defined, for each occurrence, the same as R$^1$ and R$^2$.

A polymeric precursor molecule can be represented by the formula {$M^A$(ER)(ER)$M^B$(ER)(ER)}, or {$M^A$(ER)$_2M^B$(ER)$_2$}, which are each understood to represent an {AB} repeating unit of a polymeric precursor (AB)$_n$. This shorthand representation is used in the following paragraphs to describe further examples of polymeric precursors. Further, when more than one kind of atom $M^B$ is present, the amount of each kind may be specified in these examples by the notation (x $M^{B1}$,y $M^{B2}$). For example, the polymeric compound {Ag(Se$^n$Bu)$_2$(0.75 In,0.25 Ga)(Se$^n$Bu)$_2$} is composed of repeating units, where the repeating units appear in random order, and 75% of the repeating units contain an indium atom and 25% contain a gallium atom.

Examples of polymeric precursor compounds of this disclosure include compounds having any one of the repeat unit formulas: {Ag(Se$^{sec}$Bu)$_4$In}, {Ag$^{0.6}$(Se$^{sec}$Bu)$_{3.6}$In}, {Ag$_{0.9}$(Se$^s$Bu)$_{3.9}$In}, {Ag$_{1.5}$(Se$^s$Bu)$_{4.5}$In}, {Ag(Se$^s$Bu)$_3$(Se$^t$Bu)In}, {Ag(Se$^s$Bu)$_4$Ga}, {Ag$_{0.8}$(Se$^s$Bu)$_{3.8}$In$_{0.2}$Ga$_{0.8}$}, {Ag(Se$^s$Bu)$_4$In$_{0.3}$Ga$_{0.7}$}, {Ag(Se$^s$Bu)$_4$In$_{0.7}$Ga$_{0.3}$}, {Ag(Se$^s$Bu)$_4$In$_{0.5}$Ga$_{0.5}$}, {Ag(Se$^s$Bu)$_3$(Se$^t$Bu)Ga$_{0.3}$In$_{0.7}$}.

Examples of polymeric precursor compounds of this disclosure include compounds having any one of the repeat unit formulas: {Ag(S$^t$Bu)(S$^i$Pr)In(S$^i$Pr)$_2$}; {Ag(S$^t$Bu)$_2$In(S$^t$Bu)$_2$}; {Ag(S$^t$Bu)(S$^n$Bu)In(S$^n$Bu)$_2$}; {Ag(Se$^t$Bu)(Se$^n$Bu)In(Se$^n$Bu)$_2$}; {Ag(S$^t$Bu)(Se$^t$Bu)In(Se$^t$Bu)$_2$}; {Ag(Se$^t$Bu)(S$^t$Bu)Ga(S$^t$Bu)$_2$}; {Ag(Se$^t$Bu)$_2$Ga(Se$^t$Bu)$_2$}; {Ag(S$^t$Bu)$_2$Ga(S$^t$Bu)$_2$}; {Ag(Se$^t$Bu)$_2$In(Se$^t$Bu)$_2$}; {Ag(Se$^t$Bu)(Se$^i$Pr)In(Se$^i$Pr)$_2$}; {Ag(Se$^t$Bu)(S$^s$Bu)In(S$^s$Bu)$_2$}; {Ag(Se$^t$Bu)(Se$^i$Pr)Ga(Se$^i$Pr)$_2$}; and {Ag(S$^t$Bu)(S$^i$Pr)Ga(S$^i$Pr)$_2$}.

Examples of polymeric precursor compounds of this disclosure include compounds having any one of the repeat unit formulas: {Ag(Se$^t$Bu)(Se$^n$Bu)In(Se$^n$Bu)$_2$}; {Ag(S$^t$Bu)(S$^i$Pr)In(S$^i$Pr)$_2$}; {Ag(S$^n$Bu)(S$^t$Bu)In(S$^t$Bu)$_2$}; {Ag(Se$^n$Bu)(Se$^t$Bu)In(Se$^t$Bu)$_2$}; {Ag(S$^t$Bu)(Se$^t$Bu)In(Se$^t$Bu)$_2$}; {Ag(Se$^t$Bu)(S$^t$Bu)Ga(S$^t$Bu)$_2$}; {Ag(S$^n$Bu)(S$^t$Bu)Ga(S$^t$Bu)$_2$}; {Ag(Se$^s$Bu)(Se$^t$Bu)In(Se$^t$Bu)$_2$}; {Ag(Se$^t$Bu)(Se$^i$Pr)In(Se$^i$Pr)$_2$}; {Ag(Se$^t$Bu)(S$^s$Bu)In(S$^s$Bu)$_2$}; {Ag(Se$^t$Bu)(Se$^i$Pr)Ga(Se$^i$Pr)$_2$}; and {Ag(S$^t$Bu)(S$^i$Pr)Ga(S$^i$Pr)$_2$}.

Examples of polymeric precursor compounds of this disclosure include compounds having any one of the repeat unit formulas: {Ag(S$^t$Bu)(S$^i$Pr)(In,Ga)(S$^i$Pr)$_2$}; {Ag(S$^t$Bu)$_2$(In,Ga)(S$^t$Bu)$_2$}; {Ag(S$^t$Bu)(S$^n$Bu)(In,Ga)(S$^n$Bu)$_2$}; {Ag(Se$^t$Bu)(Se$^n$Bu)(In,Ga)(Se$^n$Bu)$_2$}; {Ag(S$^t$Bu)(Se$^t$Bu)(In,Ga)(Se$^t$Bu)$_2$}; {Ag(Se$^t$Bu)(S$^t$Bu)(In,Ga)(S$^t$Bu)$_2$}; {Ag(Se$^t$Bu)$_2$(In,Ga)(Se$^t$Bu)$_2$}; {Ag(S$^t$Bu)$_2$(In,Ga)(S$^t$Bu)$_2$}; {Ag(Se$^t$Bu)$_2$(In,Ga)(Se$^t$Bu)$_2$}; {Ag(Se$^t$Bu)(Se$^i$Pr)(In,Ga)(Se$^i$Pr)$_2$}; {Ag(Se$^t$Bu)(S$^s$Bu)(In,Ga)(S$^s$Bu)$_2$}; {Ag(Se$^t$Bu)(Se$^i$Pr)(In,Ga)(Se$^i$Pr)$_2$}; and {Ag(S$^t$Bu)(S$^i$Pr)(In,Ga)(S$^i$Pr)$_2$}.

Examples of polymeric precursor compounds of this disclosure include compounds having any one of the repeat unit formulas: {Ag(Se$^t$Bu)(Se$^n$Bu)(In,Ga)(Se$^n$Bu)$_2$}; {Ag(S$^t$Bu)(S$^i$Pr)(In,Ga)(S$^i$Pr)$_2$}; {Ag(S$^n$Bu)(S$^t$Bu)(In,Ga)(S$^t$Bu)$_2$}; {Ag(Se$^n$Bu)(Se$^t$Bu)(In,Ga)(Se$^t$Bu)$_2$}; {Ag(S$^t$Bu)(Se$^t$Bu)(In,Ga)(Se$^t$Bu)$_2$}; {Ag(Se$^t$Bu)(S$^t$Bu)(In,Ga)(S$^t$Bu)$_2$}; {Ag(S$^n$Bu)(S$^t$Bu)(In,Ga)(S$^t$Bu)$_2$}; {Ag(Se$^s$Bu)(Se$^t$Bu)(In,Ga)(Se$^t$Bu)$_2$}; {Ag(Se$^t$Bu)(S$^i$Pr)(In,Ga)(S$^i$Pr)$_2$}; {Ag(Se$^t$Bu)(S$^s$Bu)(In,Tl)(S$^s$Bu)$_2$}; {Ag(Se$^t$Bu)(Se$^i$Pr)(Ga,Tl)(Se$^i$Pr)$_2$; and {Ag(S$^t$Bu)(S$^i$Pr)(In,Ga)(S$^i$Pr)$_2$}.

Examples of polymeric precursor compounds of this disclosure include compounds having any one of the repeat unit formulas: {(0.85 Ag)(0.85 Se$^t$Bu)(Se$^n$Bu)(0.7 In,0.3 Ga)(Se$^n$Bu)$_2$}; {(0.9 Ag)(0.9 S$^t$Bu)(S$^t$Bu)(0.85 In,0.15 Ga)(S$^t$ Bu)$_2$}; {(0.75 Ag)(0.75 S$^t$Bu)(S''Bu)(0.80 In,0.20 Ga)(S''Bu)$_2$}; {(0.8 Ag)(0.8 Se$^t$Bu)(Se''Bu)(0.75 In,0.25 Ga)(Se''Bu)$_2$}; {(0.95 Ag)(0.95 S$^t$Bu)(Se''Bu)(0.70 In,0.30 Ga)(Se$^t$Bu)$_2$}; {(0.98 Ag)(0.98 Se$^t$Bu)(S$^t$Bu)(0.600 In,0.400 Ga)(S$^t$Bu)$_2$}; {(0.835 Ag)(0.835 Se$^t$Bu)$_2$(0.9 In,0.1 Ga)(Se$^t$Bu)$_2$}; {Ag(S$^t$Bu)$_2$(0.8 In,0.2 Ga)(S$^t$Bu)$_2$}; {Ag(Se$^t$Bu)$_2$(0.75 In,0.25 Ga)(Se$^t$Bu)$_2$}; {Ag(Se$^t$Bu)(Se$^i$Pr)(0.67 In,0.33 Ga)(Se$^i$Pr)$_2$}; {Ag(Se$^t$Bu)(S$^s$Bu)(0.875 In,0.125 Ga)(S$^s$Bu)$_2$}; {Ag(Se$^t$Bu)(Se$^i$Pr)(0.99 In,0.01 Ga)(Se$^i$Pr)$_2$}; and {Ag(S$^t$Bu)(S$^i$Pr)(0.97 In,0.030 Ga)(S$^i$Pr)$_2$}.

Examples of polymeric precursor compounds of this disclosure include compounds having any one of the repeat unit formulas: {Ag(Se$^s$Bu)$_2$In(Se$^s$Bu)$_2$}; {Ag(Se$^s$Bu)$_2$Ga(Se$^s$Bu)$_2$}; {Ag(S$^t$Bu)$_2$In(S$^t$Bu)$_2$}; {Ag(S$^t$Bu)$_2$In(S''Bu)$_2$}; {Ag(Se$^t$Bu)$_2$Ga(Se''Bu)$_2$}; {Ag(Se$^t$Bu)$_2$Ga(Se$^t$Bu)$_2$}; {Ag(S$^t$Bu)$_2$In(S$^t$Bu)$_2$}; {Ag(Se''Bu)(Se$^t$Bu)In(Se$^t$Bu)$_2$}; {Ag(S$^t$Bu)$_2$Ga(S$^t$Bu)$_2$}; and {Ag(Se''Bu)(Se$^t$Bu)Ga(Se$^t$Bu)$_2$}.

Examples of polymeric precursor compounds of this disclosure include compounds having any one of the repeat unit formulas: {Ag(Se$^t$Bu)(Se''Bu)(0.5 In,0.5 Ga)(Se''Bu)$_2$}; {Ag(Se$^t$Bu)(Se''Bu)(0.75 In,0.25 Ga)(Se''Bu)$_2$}; {Ag(S$^t$Bu)$_2$(0.75 In,0.25 Ga)(S$^t$Bu)$_2$}; and {Ag(S$^t$Bu)$_2$(0.9 In,0.1 Ga)(S$^t$Bu)$_2$}.

Examples of polymeric precursor compounds of this disclosure include compounds having any one of the repeat unit formulas: {Ag(Se(n-pentyl))(Se''Bu)(0.5 In,0.5 Ga)(Se''Bu)$_2$}; {Ag(Se(n-hexyl))(Se''Bu)(0.75 In,0.25 Ga)(Se''Bu)$_2$}; {Ag(S(n-heptyl))(S$^t$Bu)(0.75 In,0.25 Ga)(S$^t$Bu)$_2$}; and {Ag(S(n-octyl))(S$^t$Bu)(0.9 In,0.1 Ga)(S$^t$Bu)$_2$}.

Examples of polymeric precursor compounds of this disclosure include compounds having any one of the repeat unit formulas: {Ag(Se$^t$Bu)(Se''Bu)(In,Ga)(Se''Bu)$_2$}; {Ag(S$^t$Bu)(S$^i$Pr)(In,Ga)(S$^i$Pr)$_2$}; {Ag(S$^t$Bu)(S$^i$Pr)(In,Ga)(S$^i$Pr)$_2$}; {Ag(S$^t$Bu)$_2$(In,Ga)(S$^t$Bu)$_2$}; {Ag(S$^t$Bu)(S$^i$Pr)(0.9 In,0.1 Ga)(S$^i$Pr)$_2$}; {Ag(S$^t$Bu)$_2$(0.85 In,0.15 Ga)(S$^t$Bu)$_2$}.

Examples of polymeric precursor compounds of this disclosure include compounds having any one of the repeat unit formulas: {Cu$_{0.5}$Ag$_{0.5}$(Se$^s$Bu)$_4$In}, {Cu$_{0.7}$Ag$_{0.1}$(Se$^s$Bu)$_{3.8}$Ga$_{0.3}$In$_{0.7}$}, {Cu$_{0.8}$Ag$_{0.2}$(Se$^s$Bu)$_4$In}, {Cu$_{0.2}$Ag$_{0.8}$(Se$^s$Bu)$_4$In}, {Cu$_{0.5}$Ag$_{0.5}$(Se$^s$Bu)$_4$Ga$_{0.5}$In$_{0.5}$}, {Cu$_{0.85}$Ag$_{0.1}$(Se$^s$Bu)$_{3.95}$Ga$_{0.3}$In$_{0.7}$}, {Cu$_{0.5}$Ag$_{0.5}$(Se$^s$Bu)$_4$Ga$_{0.3}$In$_{0.7}$}, and {Cu$_{0.8}$Ag$_{0.05}$(Se$^s$Bu)$_{3.85}$Ga$_{0.3}$In$_{0.7}$}.

Examples of polymeric precursor compounds of this disclosure include compounds having any one of the repeat unit formulas: {(Cu,Ag)(Se$^t$Bu)(Se''Bu)(In,Ga)(Se''Bu)$_2$}; {(Cu,Ag)(S$^t$Bu)(S$^i$Pr)(In,Ga)(S$^i$Pr)$_2$}; {(Cu,Ag)(Se$^t$Bu)(Se''Bu)In(Se''Bu)$_2$}; and {(Cu,Ag)(S$^t$Bu)(S$^i$Pr)In(S$^i$Pr)$_2$}.

Examples of polymeric precursor compounds of this disclosure include compounds having any one of the repeat unit formulas: {Cu$_{1.40}$Ag$_{0.10}$(Se$^t$Bu)$_{1.5}$(Se''Bu)(In$_{0.7}$Ga$_{0.3}$)(Se''Bu)$_2$}; {Cu$_{1.30}$Ag$_{0.10}$(S$^t$Bu)$_{1.4}$(S$^t$Bu)(In$_{0.85}$Ga$_{0.15}$)(S$^t$Bu)$_2$}; {Cu$_{1.20}$Ag$_{0.20}$(S$^t$Bu)$_{1.4}$(S''Bu)(In$_{0.80}$Ga$_{0.20}$)(S''Bu)$_2$}; {Cu$_{1.10}$Ag$_{0.20}$(Se$^t$Bu)$_{1.3}$(Se''Bu)(In$_{0.75}$Ga$_{0.25}$)(Se''Bu)$_2$}; {Cu$_{1.10}$Ag$_{0.10}$(S$^t$Bu)$_{1.2}$(Se''Bu)(In$_{0.7}$Ga$_{0.3}$)(Se$^t$Bu)$_2$}; and {Cu$_{1.05}$Ag$_{0.05}$(Se$^t$Bu)$_{1.1}$(S$^t$Bu)(In$_{0.6}$Ga$_{0.4}$)(S$^t$Bu)$_2$}.

Examples of polymeric precursor compounds of this disclosure include compounds having any one of the repeat unit formulas: {Cu$_{0.90}$Ag$_{0.10}$(Se$^t$Bu)(Se''Bu)(In$_{0.7}$Ga$_{0.3}$)(Se''Bu)$_2$}; {Cu$_{0.85}$Ag$_{0.10}$(S$^t$Bu)$_{0.95}$(S$^t$Bu)(In$_{0.85}$Ga$_{0.15}$)(S$^t$Bu)$_2$}; {Cu$_{0.80}$Ag$_{0.20}$(S$^t$Bu)(S''Bu)(In$_{0.80}$Ga$_{0.20}$)(S''Bu)$_2$}; {Cu$_{0.75}$Ag$_{0.20}$(Se$^t$Bu)$_{0.95}$(Se''Bu)(In$_{0.75}$Ga$_{0.25}$)(Se''Bu)$_2$}; {Cu$_{0.70}$Ag$_{0.30}$(S$^t$Bu)(Se$^t$Bu)(In$_{0.7}$Ga$_{0.3}$)(Se$^t$Bu)$_2$}; {Cu$_{0.65}$Ag$_{0.30}$(Se$^t$Bu)$_{0.95}$(S$^t$Bu)(In$_{0.6}$Ga$_{0.4}$)(S$^t$Bu)$_2$}; {Cu$_{0.60}$Ag$_{0.40}$(Se$^t$Bu)$_2$(In$_{0.5}$Ga$_{0.5}$)(Se$^t$Bu)$_2$}; {Cu$_{0.50}$Ag$_{0.50}$(Se$^t$Bu)(Se''Bu)(In$_{0.5}$Ga$_{0.5}$)(Se''Bu)$_2$}; {Cu$_{0.30}$Ag$_{0.65}$(S$^t$Bu)$_{0.95}$(S$^t$Bu)(In$_{0.5}$Ga$_{0.5}$)(S$^t$Bu)$_2$}; {Cu$_{0.30}$Ag$_{0.70}$(S$^t$Bu)(S''Bu)(In$_{0.4}$Ga$_{0.6}$)(S''Bu)$_2$}; {Cu$_{0.20}$Ag$_{0.75}$(Se$^t$Bu)$_{0.95}$(Se''Bu)(In$_{0.4}$Ga$_{0.6}$)(Se''Bu)$_2$}; {Cu$_{0.20}$Ag$_{0.80}$(S$^t$Bu)(Se$^t$Bu)(In$_{0.3}$Ga$_{0.7}$)(Se$^t$Bu)$_2$}; {Cu$_{0.10}$Ag$_{0.85}$(Se$^t$Bu)$_{0.95}$(S$^t$Bu)(In$_{0.3}$Ga$_{0.7}$)(S$^t$Bu)$_2$}; and {Cu$_{0.10}$Ag$_{0.90}$(Se$^t$Bu)$_2$(In$_{0.3}$Ga$_{0.7}$)(Se$^t$Bu)$_2$}.

Preparation of Polymeric Precursors (MPP)

Embodiments of this invention provide a family of polymeric precursor molecules and compositions which can be synthesized from monomers. Monomers of this disclosure include a compound containing an atom $M^B$ of Group 13 selected from Ga and In, and a compound containing a monovalent atom $M^A$ selected from Cu and Ag.

Advantageously facile routes for the synthesis and isolation of polymeric precursor compounds of this invention have been discovered, as described below.

This disclosure provides a range of polymeric precursor compositions which can be transformed into semiconductor materials and semiconductors. In some aspects, the polymeric precursor compositions are precursors for the formation of semiconductor materials and semiconductors.

In general, the polymeric precursor compositions of this invention are non-oxide chalcogen compositions.

In some embodiments, the polymeric precursor compositions are sources or precursors for the formation of absorber layers for solar cells, including CAIGS, AIGS, CAIS, CAGS, AIS, and AGS absorber layers.

A polymeric precursor compound may be made with any desired stoichiometry with respect to the number of different metal atoms and Group 13 elements and their respective ratios.

As discussed below, a polymeric precursor compound may be made by reacting monomers to produce a polymer chain. The polymeric precursor formation reactions can include initiation, propagation, and termination.

Methods for making a polymeric precursor may include the step of contacting a compound $M^B(ER)_3$ with a compound $M^A(ER)$, where $M^A$, $M^B$, E, and R are as defined above.

As shown in Reaction Scheme 1, a method for making a polymeric precursor may include the step of contacting a compound $M^B(ER^1)_3$ with a compound $M^A(ER^2)$, where $M^A$, $M^B$, and E are as defined above and the groups $R^1$ and $R^2$ of the compounds may be the same or different and are as defined above.

REACTION SCHEME 1:

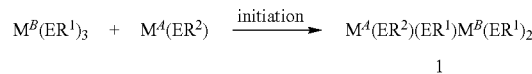

1

In Reaction Scheme 1, $M^B(ER^1)_3$ and $M^A(ER^2)$ are monomers that form the first adduct 1, $M^A(ER)_2 M^B(ER)_2$. Reaction Scheme 1 represents the initiation of a polymerization of monomers. In one aspect, Reaction Scheme 1 represents the formation of the intermediate adduct AB. In general, among other steps, the polymerization reaction may form polymer chains by adding monomers to the first adduct 1, so that the first adduct 1 may be a transient molecule that is not observed when a longer chain is ultimately produced. When additional monomers are bound to either end of the first adduct 1, then the first adduct 1 becomes a repeating unit AB in the polymer chain.

In general, to prepare a polymeric precursor, the compounds $M^B(ER)_3$ and $M^A(ER)$ can be generated by various reactions.

For example, a compound $M^A(ER)$ can be prepared by reacting $M^AX$ with $M^+(ER)$. $M^+(ER)$ can be prepared by reacting E with LiR to provide Li(ER). Li(ER) can be acidified to provide HER, which can be reacted with Na(OR) or K(OR) to provide Na(ER) and K(ER), respectively. In these reactions, E, R and $M^A$ are as defined above.

In another example, a compound $M^A(ER)$ can be prepared by reacting $M^AX$ with $(RE)Si(CH_3)_3$. The compound $(RE)Si(CH_3)_3$ can be made by reacting $M^+(ER)$ with $XSi(CH_3)_3$, where $M^+$ is Na, Li, or K, and X is halogen.

In another example, a compound $M^A(ER)$ can be prepared by reacting $M^A{}_2O$ with HER. In particular, Cu(ER) can be prepared by reacting $Cu_2O$ with HER.

For example, a compound $M^B(ER)_3$ can be prepared by reacting $M^BX_3$ with $M^+(ER)$. $M^+(ER)$ can be prepared as described above.

In another example, a compound $M^B(ER)_3$ can be prepared by reacting $M^BX_3$ with $(RE)Si(CH_3)_3$. The compound $(RE)Si(CH_3)_3$ can be made as described above.

In another example, a compound $M^B(ER)_3$ can be prepared by reacting $M^BR_3$ with HER.

Moreover, in the preparation of a polymeric precursor, a compound $M^+M^B(ER)_4$ can optionally be used in place of a portion of the compound $M^B(ER)_3$. For example, a compound $M^+M^B(ER)_4$ can be prepared by reacting $M^BX_3$ with 4 equivalents of $M^+(ER)$, where $M^+$ is Na, Li, or K, and X is halogen. The compound $M^+(ER)$ can be prepared as described above.

The propagation of the polymeric precursor can be represented in part by the formulas in Reaction Scheme 2. The formulas in Reaction Scheme 2 represent only some of the reactions and additions which may occur in propagation of the polymeric precursor.

REACTION SCHEME 2:

$$1 + M^B(ER^1)_3 \xrightarrow{\text{propogation}} (R^1E)M^B(ER^1)_2M^A(ER^2)(ER^1)M^B(ER^1)_2$$
$$2$$

$$1 + M^A(ER^2) \xrightarrow{\text{propogation}} M^A(ER^2)(ER^1)M^B(ER^1)_2M^A(ER^2)$$
$$3$$

In Reaction Scheme 2, the addition of a monomer $M^B(ER^1)_3$ or $M^A(ER^2)$ to the first adduct 1, may produce additional adducts 2 and 3, respectively. In one aspect, Reaction Scheme 2 represents the formation of the adduct (RE)-BAB, as well as the adduct intermediate AB-$M^A$(ER). In general, the adducts 2 and 3 may be transient moieties that are not observed when a longer chain is ultimately produced.

The products of the initial propagation steps may continue to add monomers in propagation. As shown in Reaction Scheme 3, adduct 2 may add a monomer $M^B(ER^1)_3$ or $M^A(ER^2)$.

REACTION SCHEME 3:

$$2 + M^A(ER^2) \xrightarrow{\text{propogation}} (R^1E)M^B(ER^1)_2M^A(ER^2)(ER^1)M^B(ER^1)_2M^A(ER^2)$$
$$4$$
$$+$$

-continued
$$M^A(ER^2)(ER^1)M^B(ER^1)_2M^A(ER^2)(ER^1)M^B(ER^1)_2$$
$$5$$

$$2 + M^B(ER^1)_3 \xrightarrow{\text{propogation}} (R^1E)_2M^B(ER^1)_2M^B(ER^1)_2M^A(ER^2)(ER^1)M^B(ER^1)_2$$
$$6$$

In one aspect, Reaction Scheme 3 represents the formation of the intermediate adduct $(RE)$-BAB-$M^A(ER)_4$, as well as the adduct $(RE)_2$-BBAB 6. In general, the molecules 4, 5 and 6 may be transient molecules that are not observed when a longer chain is ultimately produced.

Other reactions and additions which may occur include the addition of certain propagating chains to certain other propagating chains. For example, as shown in Reaction Scheme 4, adduct 1 may add to adduct 2 to form a longer chain.

REACTION SCHEME 4:

$$1 + 2 \xrightarrow{\text{propogation}} (R^1E)M^B(ER^1)_2M^A(ER^2)(ER^1)M^B(ER^1)_2M^A(ER^2)(ER^1)M^B(ER^1)_2$$
$$7$$

In one aspect, Reaction Scheme 4 represents the formation of the adduct (RE)-BABAB 7.

Any of the moieties 4, 5, 6, and 7 may be transient, and may not be observed when a longer chain is ultimately produced.

In some variations, a propagation step may provide a stable molecule. For example, moiety 6 may be a stable molecule.

In general, AB alternating block copolymers as described in Formulas 18 through 22 may be prepared by sequential addition of the corresponding monomers $M^{B1}(ER)_3$ and $M^{B2}(ER)_3$, as well as $M^{A1}(ER)$ and $M^{A2}(ER)$ during polymerization or propagation.

Certain reactions or additions of the polymeric precursor propagation may include the formation of chain branches. As shown in Reaction Scheme 5, the addition of a monomer $M^A(ER^2)$ to the adduct molecule 2 may produce a branched chain 8.

REACTION SCHEME 5:

$$7 + M^A(ER^2) \xrightarrow{\text{branching}}$$

$$(R^1E)M^B(ER^1)_2M^A(ER^2)(ER^1)M^B(ER^1)_2M^A(ER^2)(ER^1)M^B(ER^1)_2$$

$$\begin{array}{c} M^A \\ ER^1 \quad ER^2 \\ M^B \\ ER^1 \quad ER^1 \\ M^A \\ ER^1 \quad ER^2 \\ M^B \\ R^1E \quad ER^1 \end{array}$$
$$8$$

The propagation of the polymeric precursor can be represented in part by the formulas in Reaction Schemes 2, 3, 4 and 5. The formulas in Reaction Schemes 2, 3, 4 and 5 represent only some representative reactions and additions which may occur in propagation of the polymeric precursor.

Termination of the propagating polymer chain may occur by several mechanisms. In general, because of the valencies of the atoms $M^A$ and $M^B$, a completed polymer chain may terminate in a $M^B$ unit, but not an $M^A$ unit. In some aspects, a chain terminating unit is a •••B unit, or a $(ER)_2B$••• unit.

In some aspects, the propagation of the polymeric precursor chain may terminate when either of the monomers $M^B(ER)_3$ or $M^A(ER)$ becomes depleted.

In certain aspects, as shown in Reaction Scheme 6, the propagation of the polymeric precursor chain may terminate when a growing chain represented by the formula (RE)-B••••••B reacts with another chain having the same terminal (RE)-B unit to form a chain having the formula B••••••BB••••••B.

REACTION SCHEME 6:

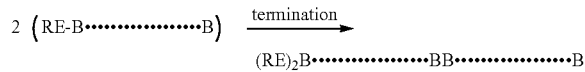

In Reaction Scheme 6, two chains have combined, where the propagation of the polymer chain is essentially terminated and the product chain $(RE)_2B$••••••$BB$••••••B has chain terminating units that are B units.

In further aspects, the propagation of the polymeric precursor chain may terminate when the growing chain forms a ring. As shown in Reaction Scheme 7, a propagating chain such as 5 may terminate by cyclization in which the polymer chain forms a ring.

REACTION SCHEME 7:

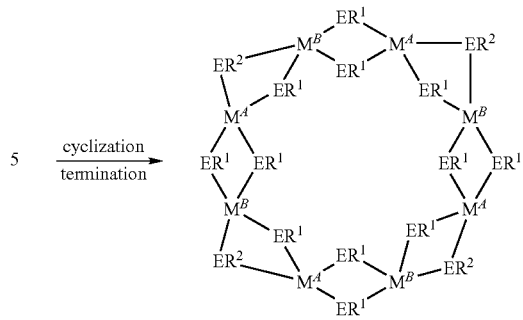

A polymeric precursor compound may be a single chain, or a distribution of chains having different lengths, structures or shapes, such as branched, networked, dendrimeric, and cyclic shapes, as well as combinations of the forgoing. A polymeric precursor compound may be any combination of the molecules, adducts and chains described above in Reaction Schemes 1 through 7.

A polymeric precursor of this disclosure may be made by the process of providing a first monomer compound having the formula $M^B(ER^1)_3$, providing a second monomer compound having the formula $M^A(ER^2)$, and contacting the first monomer compound with the second monomer compound.

In some embodiments, the first monomer compound may be a combination of compounds having the formulas $M^{B1}(ER^1)_3$ and $M^{B2}(ER^2)_3$, wherein $M^{B1}$ and $M^{B2}$ are different atoms of Group 13, and $R^1$, $R^2$ are the same or different and are independently selected from alkyl, aryl, heteroaryl, alkenyl, amido, silyl, and inorganic and organic ligands.

In some variations, the second monomer compound may be a combination of compounds having the formulas $M^{A1}(ER^3)$ and $M^{A2}(ER^4)$, wherein $M^{A1}$ is Cu and $M^{A2}$ is Ag, and $R^3$, $R^4$ are defined the same as $R^1$ and $R^2$.

In further aspects, a method for making a polymeric precursor may include the synthesis of a compound containing two or more atoms of $M^B$ and contacting the compound with a compound $M^A(ER)$, where $M^A$, $M^B$, E and R are as defined above. For example, $(ER)_2M^{B1}(ER)_2M^{B2}(ER)_2$ can be reacted with $M^A(ER^2)$, where $M^{B1}$ and $M^{B2}$ are the same or different atoms of Group 13.

Methods for making a polymeric precursor include embodiments in which the first monomer compound and the second monomer compound may be contacted in a process of depositing, spraying, coating, or printing. In certain embodiments, the first monomer compound and the second monomer compound may be contacted at a temperature of from about −60° C. to about 100° C., or from about 0° C. to about 200° C.

Controlled Stoichiometry of Polymeric Precursors (MPP)

A polymeric precursor compound may be made with any desired stoichiometry with respect to the number of different metal atoms and Group 13 elements and their respective ratios.

In some embodiments, the stoichiometry of a polymeric precursor compound may be controlled through the numbers of equivalents of the monomers in the formation reactions.

In some aspects, the monomers $M^{B1}(ER)_3$ and $M^{B2}(ER^1)_3$ can be used for polymerization. Examples of these monomers are $In(ER)_3$ and $Ga(ER^1)_3$, where the groups R, $R^1$ are the same or different and are groups attached through a carbon or non-carbon atom, including alkyl, aryl, heteroaryl, alkenyl, amido, silyl, and inorganic and organic ligands. In some embodiments, the groups R, $R^1$ are the same or different and are alkyl groups attached through a carbon atom.

In further aspects, the monomers $M^{B1}(ER)(ER^1)_2$ and $M^{B2}(ER^2)(ER^3)_2$ can be used for polymerization, where the groups R, $R^1$, $R^2$, $R^3$ are each the same or different from the others and are groups attached through a carbon or non-carbon atom, including alkyl, aryl, heteroaryl, alkenyl, amido, silyl, and inorganic and organic ligands. In some embodiments, the groups R, $R^1$, $R^2$, $R^3$ are each the same or different from the others and are alkyl groups attached through a carbon atom.

Embodiments of this invention may further provide that the stoichiometry of a polymeric precursor compound may be controlled to any desired level through the adjustment of the amounts of each of the monomers provided in the formation reactions.

As shown in Reaction Scheme 8, a polymerization to form a polymeric precursor may be initiated with a mixture of monomers $M^A(ER^3)$, $M^{B1}(ER^1)_3$, and $M^{B2}(ER^2)_3$ having any arbitrary ratios of stoichiometry.

REACTION SCHEME 8:

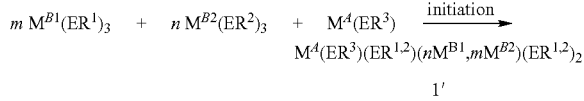

In Reaction Scheme 8, a polymerization can be performed with a mixture of monomers in any desired amounts. In certain variations, a polymerization to form a polymeric precursor may be initiated with a mixture of any combination of the monomers described above, where the number of equivalents of each monomer is adjusted to any arbitrary level.

In some variations, a polymerization to form a polymeric precursor can be done using the monomers $M^{A1}(ER^1)$ and $M^{A2}(ER^2)$, for example, which can be contacted in any desired quantity to produce any arbitrary ratio of $M^{A1}$ to $M^{A2}$.

In some aspects, for alternating copolymers of monomers $M^A(ER)$ and $M^B(ER)_3$, the ratio of $M^A$ to $M^B$ in the polymeric precursor can be controlled from a ratio as low as 1:2 in the unit BAB, for example, to a ratio of 1:1 in an alternating $(AB)_n$ polymeric precursor, to a ratio of 1.5:1 or higher. The ratio of $M^A$ to $M^B$ in the polymeric precursor may be 0.5 to 1.5, or 0.5 to 1, or 1 to 1, or 1 to 0.5, or 1.5 to 0.5. As discussed above, in further embodiments, a polymeric precursor compound may be made with any desired stoichiometry with respect to the number of different metal atoms and Group 13 elements and their respective ratios.

In certain aspects, a polymerization to form a polymeric precursor can be done to form a polymeric precursor having any ratio of $M^A$ to $M^B$. As shown in Reaction Scheme 9, a polymeric precursor having the composition $\{p\, M^A(ER)/m\, M^{B1}(ER)_3/n\, M^{B2}(ER)_3\}$ may be formed using the mixture of monomers $m\, M^{B1}(ER)_3 + n\, M^{B2}(ER)_3 + p\, M^A(ER)$.

REACTION SCHEME 9:

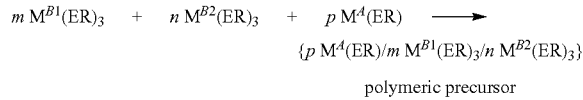

$m\, M^{B1}(ER)_3 + n\, M^{B2}(ER)_3 + p\, M^A(ER) \longrightarrow$
$\{p\, M^A(ER)/m\, M^{B1}(ER)_3/n\, M^{B2}(ER)_3\}$ polymeric precursor In certain variations, any number of monomers of $M^A(ER)$ and any number of monomers of $M^B(ER)_3$ can be used in the formation reactions. For example, a polymeric precursor may be made with the monomers $M^{A1}(ER)$, $M^{A2}(ER)$, $M^{B1}(ER)_3$, and $M^{B2}(ER^1)_3$, where the number of equivalents of each monomer is an independent and arbitrary amount.

For example, the ratios of the atoms $M^A:M^B$ in a polymeric precursor may be about 0.5:1 or greater, or about 0.6:1 or greater, or about 0.7:1 or greater, or about 0.8:1 or greater, or about 0.9:1 or greater, or about 0.95:1 or greater. In certain variations, the ratios of the atoms $M^A:M^B$ in a polymeric precursor may be about 1:1 or greater, or about 1.1:1 or greater.

In further examples, the ratios of the atoms $M^A:M^B$ in a polymeric precursor may be from about 0.5 to about 1.2, or from about 0.6 to about 1.2, or from about 0.7 to about 1.1, or from about 0.8 to about 1.1, or from about 0.8 to about 1, or from about 0.9 to about 1. In some examples, the ratios of the atoms $M^A:M^B$ in a polymeric precursor may be about 0.80, or about 0.82, or about 0.84, or about 0.86, or about 0.88, or about 0.90, or about 0.92, or about 0.94, or about 0.96, or about 0.98, or about 1.00, or about 1.02, or about 1.1, or about 1.2, or about 1.3, or about 1.5. In the foregoing ratios $M^A:M^B$, the ratio refers to the sum of all atoms of $M^A$ or $M^B$, respectively, when there are more than one kind of $M^A$ or $M^B$, such as $M^{A1}$ and $M^{A2}$ and $M^{B1}$ and $M^{B2}$.

As shown in Reaction Scheme 10, a polymeric precursor compound having the repeating unit composition $\{M^A(ER)_2(m\, M^{B1}, n\, M^{B2})(ER)_2\}$ may be formed using the mixture of monomers $m\, M^{B1}(ER)_3 + n\, M^{B2}(ER)_3 + M^A(ER)$.

REACTION SCHEME 10:

$m\, M^{B1}(ER)_3 + n\, M^{B2}(ER)_3 + M^A(ER) \longrightarrow$

$\{M^A(ER)_2(m\, M^{B1}, n\, M^{B2})(ER)_3\}$ polymeric precursor repeating unit In Reaction Scheme 10, the sum of m and n is one.

Embodiments of this invention may further provide a polymeric precursor made from monomers of $M^A(ER)$ and $M^B(ER)_3$, where the total number of equivalents of monomers of $M^A(ER)$ is less than the total number of equivalents of monomers of $M^B(ER)_3$. In certain embodiments, a polymeric precursor may be made that is substoichiometric or deficient in atoms of $M^A$ relative to atoms of $M^B$.

As used herein, the expression $M^A$ is deficient, or $M^A$ is deficient to $M^B$ refers to a composition or formula in which there are fewer atoms of $M^A$ than $M^B$. For example, for a compound having the empirical formula $(Cu_{1-x}Ag_x)_u(M^{B1}_{1-y}M^{B2}_y)_v((S^1_{1-z}Se^2_z)R)_w$, the compound would be deficient in a Group 11 atom when u is less than v.

As used herein, the expression $M^A$ is enriched, or $M^A$ is enriched relative to $M^B$ refers to a composition or formula in which there are more atoms of $M^A$ than $M^B$.

As shown in Reaction Scheme 11, a polymeric precursor having the empirical formula $M^A_x(M^{B1}_{1-y}M^{B2}_y)_v((S_{1-z}Se_z)R)_w$ may be formed using the mixture of monomers $M^{B1}(ER)_3$, $M^{B2}(ER)_3$ and $M^A(ER)$.

REACTION SCHEME 11:

$v(1-y)\, M^{B1}(ER)_3 + v(y)\, M^{B2}(ER)_3 + x\, M^A(ER) \longrightarrow$

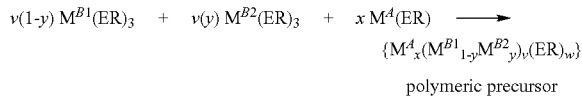

$\{M^A_x(M^{B1}_{1-y}M^{B2}_y)_v(ER)_w\}$ polymeric precursor where w is (3v+x).

A precursor compound of this disclosure may be a combination of u*(1−x) equivalents of Cu(ER), u*x equivalents of Ag(ER), v*(1−y) equivalents of In(ER)$_3$, v*y equivalents of Ga(ER)$_3$, wherein the compound has the empirical formula $(Cu_{1-x}Ag_x)_u(In_{1-y}Ga_y)_v((S_{1-z}Se_z)R)_w$, wherein x is from 0 to 1, y is from 0 to 1, z is from 0 to 1, u is from 0.5 to 1.5, v is from 0.5 to 1.5, w is from 2 to 6, and R represents R groups, of which there are w in number, which are independently selected from alkyl, aryl, heteroaryl, alkenyl, amido, silyl, and inorganic and organic ligands.

A precursor compound of this disclosure may be a combination of u*(1−x) equivalents of Cu(ER), u*x equivalents of Ag(ER), v*(1−y) equivalents of In(ER)$_3$, v*y equivalents of Ga(ER)$_3$, wherein the compound has the empirical formula $(Cu_{1-x}Ag_x)_u(In_{1-y}Ga_y)_v((S_{1-z}Se_z)R)_w$, wherein x is from 0 to 1, y is from 0 to 1, z is from 0 to 1, u is from 0.7 to 1.0, v is from 0.9 to 1.1, w is from 3.6 to 4.4, and R represents R groups, of which there are w in number, which are independently selected from alkyl, aryl, heteroaryl, alkenyl, amido, silyl, and inorganic and organic ligands.

In some embodiments, a precursor compound can be a combination of w*(1−z) equivalents of Cu(ER$^1$), w*z equivalents of Ag(ER$^2$), x equivalents of In(ER$^3$)$_3$, y equivalents of Ga(ER$^4$)$_3$, wherein the compound has the empirical formula $(Cu_{1-z}Ag_z)_wIn_xGa_y(ER^1)_{w(1-z)}(ER^2)_{(w*z)}(ER^3)_{3x}(ER^4)_{3y}$, w is from 0.5 to 1.5, z is from 0 to 1, x is from 0 to 1, y is from 0 to 1, x plus y is one, and wherein $R^1$, $R^2$, $R^3$, $R^4$ are the same or each different, and are independently selected, for each occurrence, from alkyl, aryl, heteroaryl, alkenyl, amido, silyl, and inorganic and organic ligands.

In some embodiments, a precursor compound can be a combination of w*(1−z) equivalents of Cu(ER$^1$), w*z equivalents of Ag(ER$^2$), x equivalents of In(ER$^3$)$_3$, y equivalents of Ga(ER$^4$)$_3$, wherein the compound has the empirical formula (Cu$_{1-z}$Ag$_z$)$_w$In$_x$Ga$_y$(ER$^1$)$_{w(1-z)}$(ER$^2$)$_{(w*z)}$(ER$^3$)$_{3x}$(ER$^4$)$_{3y}$, w is from 0.7 to 1.0, z is from 0 to 1, x is from 0 to 1, y is from 0 to 1, x plus y is one, and wherein R$^1$, R$^2$, R$^3$, R$^4$ are the same or each different, and are independently selected, for each occurrence, from alkyl, aryl, heteroaryl, alkenyl, amido, silyl, and inorganic and organic ligands.

The empirical formula of a polymeric precursor can be, for example, the following: M$^A_u$(M$^{B1}_{1-y}$M$^{B2}_y$)$_v$((S$_{1-z}$Se$_z$)R)$_w$, where M$^A$, M$^{B1}$ and M$^{B2}$ are as defined above, R is as defined above, u is from 0.5 to 1.5, y is from 0 to 1, and z is from 0 to 1, v is from 0.5 to 1.5, and w is from 2 to 6.

In some embodiments, the empirical formula of a polymeric precursor is Ag$_u$(In$_{1-y}$Ga$_y$)$_v$((S$_{1-z}$Se$_z$)R)$_w$, where R is as defined above, u is from 0.5 to 1.5, y is from 0 to 1, and z is from 0 to 1, v is from 0.5 to 1.5, and w is from 2 to 6.

In some embodiments, the empirical formula of a polymeric precursor is Ag$_u$(In$_{1-y}$Ga$_y$)$_v$((S$_{1-z}$Se$_z$)R)$_w$, where R is as defined above, u is from 0.7 to 1.2, y is from 0 to 1, and z is from 0 to 1, v is from 0.7 to 1.2, and w is from 2 to 6.

In some embodiments, the empirical formula of a polymeric precursor is Ag$_u$(In$_{1-y}$Ga$_y$)$_v$((S$_{1-z}$Se$_z$)R)$_w$, where R is as defined above, u is from 0.7 to 1.1, y is from 0 to 1, and z is from 0 to 1, v is from 0.7 to 1.1, and w is from 2 to 6.

In some embodiments, the empirical formula of a polymeric precursor is Ag$_u$(In$_{1-y}$Ga$_y$)$_v$((S$_{1-z}$Se$_z$)R)$_w$, where R is as defined above, u is from 0.7 to 1.1, y is from 0 to 1, and z is from 0.5 to 1, v is from 0.7 to 1.1, and w is from 2 to 6.

In some embodiments, the empirical formula of a polymeric precursor is Ag$_u$(In$_{1-y}$Ga$_y$)$_v$((S$_{1-z}$Se$_z$)R)$_w$, where R is as defined above, u is from 0.8 to 0.95, y is from 0.5 to 1, and z is from 0.5 to 1, v is from 0.95 to 1.05, and w is from 3.6 to 4.4.

In further aspects, a mixture of polymeric precursor compounds may advantageously be prepared with any desired stoichiometry with respect to the number of different metal atoms and Group 13 elements and their respective ratios.

As shown in Reaction Scheme 12, a polymeric precursor compound may be prepared by contacting x equivalents of M$^{B1}$(ER$^1$)$_3$, y equivalents of M$^{B2}$(ER$^2$)$_3$, and z equivalents of M$^A$(ER$^3$), where M$^{B1}$ and M$^{B2}$ are different atoms of Group 13, x is from 0.5 to 1.5, y is from 0.5 to 1.5, and z is from 0.5 to 1.5. A polymeric precursor compound may have the empirical formula Ag$_x$In$_y$Ga$_z$(ER$^1$)$_x$(ER$^2$)$_{3y}$(ER$^3$)$_{3z}$, where R$^1$, R$^2$ and R$^3$ are the same or each different from each other.

REACTION SCHEME 12:

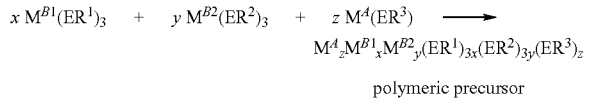

polymeric precursor

Crosslinking Polymeric Precursors

Embodiments of this invention encompass methods and compositions for crosslinking polymeric precursors and compositions.

In some aspects, a crosslinked polymeric precursor may be used to control the viscosity of a precursor composition, or a polymeric precursor ink composition. The crosslinking of a polymeric precursor can increase its molecular weight. The molecular weight of a polymeric precursor can be varied over a wide range by incorporating crosslinking into the preparation of the precursor. The viscosity of an ink composition can be varied over a wide range by using a crosslinked precursor to prepare an ink composition.

In some embodiments, the crosslinking of a polymeric precursor composition may be used to control the viscosity of the composition, or of a polymeric precursor ink composition. A polymeric precursor component of a composition can be crosslinked by adding a crosslinking agent to the composition. The viscosity of an ink composition may be varied over a wide range by adding a crosslinking agent to the ink composition.

In further aspects, the crosslinking of a polymeric precursor composition may be used to control the variation of properties of thin films made with the precursor.

Examples of a crosslinking agent include E(Si(CH$_3$)$_3$)$_2$, where E is as defined above, which can link polymer chains via an M-E-M crosslink.

Examples of a crosslinking agent include HEREH, M$^A$(E-RE)H and M$^A$(ERE)M$^A$, where M$^A$, E, and R are as defined above.

A crosslinking agent can be made by reacting Cu$_2$O with HEREH to form Cu(ERE)H or Cu(ERE)Cu.

Examples of a crosslinking agent include dithiols and diselenols, for example, HER'EH, where E and R are as defined above. A diselenol can react with two ER groups of different polymeric precursor chains to link the chains together.

An example of crosslinking using HER'EH is shown in Reaction Scheme 14. In Reaction Scheme 14, two chains of a polymeric precursor are linked by the diselenol with elimination of 2 HER.

REACTION SCHEME 14

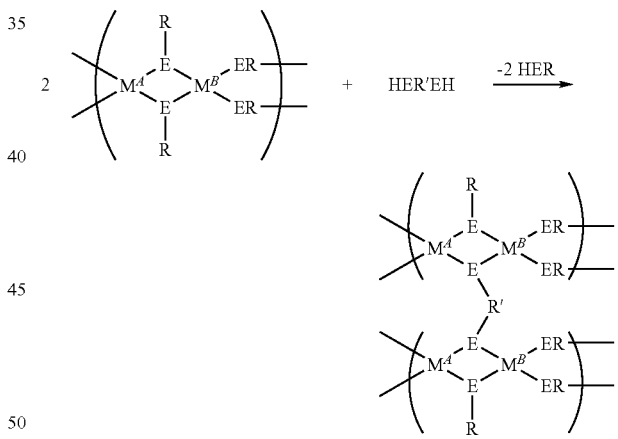

In another example, Cu(ER'E)Cu can be used during synthesis of a polymeric precursor to form crosslinks.

Embodiments of this invention may further provide a crosslinking agent having the formula (RE)$_2$M$^{13}$(ER'E)M$^{13}$(ER)$_2$, where M$^{13}$, E, R' and R are as defined above. A crosslinking agent of this kind may be used either during synthesis of a polymeric precursor to form crosslinks, or in formation of an ink or other composition.

In some embodiments, a polymeric precursor may incorporate crosslinkable functional groups. A crosslinkable functional group may be attached to a portion of the R groups of one or more kinds in the polymeric precursor.

Examples of crosslinkable functional groups include vinyl, vinylacrylate, epoxy, and cycloaddition and Diels-Alder reactive pairs. Crosslinking may be performed by methods known in the art including the use of heat, light or a catalyst, as well as by vulcanization with elemental sulfur.

Dopants

In some embodiments, a polymeric precursor composition may include a dopant. A dopant may be introduced into a polymeric precursor in the synthesis of the precursor, or alternatively, can be added to a composition or ink containing the polymeric precursor. A semiconductor material or thin film of this disclosure made from a polymeric precursor may contain atoms of one or more dopants. Methods for introducing a dopant into a photovoltaic absorber layer include preparing the absorber layer with a polymeric precursor of this invention containing the dopant.

The quantity of a dopant in an embodiment of this disclosure can be from about $1 \times 10^{-7}$ atom percent to about 5 atom percent relative to the most abundant Group 11 atom, or greater. In some embodiments, a dopant can be included at a level of from about $1 \times 10^{16}$ cm$^{-3}$ to about $1 \times 10^{21}$ cm$^{-3}$. A dopant can be included at a level of from about 1 ppm to about 10,000 ppm.

In some embodiments, a dopant may be an alkali metal atom including Li, Na, K, Rb, and a mixture of any of the foregoing.

Embodiments of this invention may further include a dopant being an alkaline earth metal atom including Be, Mg, Ca, Sr, Ba, and a mixture of any of the foregoing.

In some embodiments, a dopant may be a transition metal atom from Group 3 through Group 12.

In some embodiments, a dopant may be a transition metal atom from Group 5 including V, Nb, Ta, and a mixture of any of the foregoing.

In some embodiments, a dopant may be a transition metal atom from Group 6 including Cr, Mo, W, and a mixture of any of the foregoing.

In some embodiments, a dopant may be a transition metal atom from Group 10 including Ni, Pd, Pt, and a mixture of any of the foregoing.

In some embodiments, a dopant may be a transition metal atom from Group 12 including Zn, Cd, Hg, and a mixture of any of the foregoing.

In some embodiments, a dopant may be an atom from Group 14 including C, Si, Ge, Sn, Pb, and a mixture of any of the foregoing.

In some embodiments, a dopant may be an atom from Group 15 including P, As, Sb, Bi, and a mixture of any of the foregoing.

In some aspects, a polymeric precursor composition may advantageously be prepared to incorporate alkali metal ions as dopants. For example, a polymeric precursor composition may be prepared using an amount of Na(ER), where E is S or Se and R is alkyl or aryl. In certain embodiments, a polymeric precursor composition may be prepared using an amount of NaIn(ER)$_4$, NaGa(ER)$_4$, LiIn(ER)$_4$, LiGa(ER)$_4$, KIn(ER)$_4$, KGa(ER)$_4$, or mixtures thereof, where E is S or Se and R is alkyl or aryl. A polymeric precursor compound of this kind can be used to control the level of alkali metal ions.

A dopant may be provided in a precursor as a counterion or introduced into a thin film by any of the deposition methods described herein. A dopant may also be introduced into a thin film by methods known in the art including ion implantation.

A dopant of this disclosure may be p-type or n-type.

Any of the foregoing dopants may be used in an ink of this invention.

Capping Compounds

In some embodiments, a polymeric precursor composition may be formed as shown in Reaction Schemes 1 through 6, where one or more capping compounds are added to the reactions. A capping compound may control the extent of polymer chain formation. A capping compound may also be used to control the viscosity of an ink containing the polymeric precursor compound or composition, as well as its solubility and ability to from a suspension. Examples of capping compounds include inorganic or organometallic complexes which bind to repeating units A or B, or both, and prevent further chain propagation. Examples of capping compounds include R$_2$M$^B$ER, and RM$^B$(ER)$_2$.

Ligands

As used herein, the term ligand refers to any atom or chemical moiety that can donate electron density in bonding or coordination.

A ligand can be monodentate, bidentate or multidentate.

As used herein, the term ligand includes Lewis base ligands.

As used herein, the term organic ligand refers to an organic chemical group composed of atoms of carbon and hydrogen, having from 1 to 22 carbon atoms, and optionally containing oxygen, nitrogen, sulfur or other atoms, which can bind to another atom or molecule through a carbon atom. An organic ligand can be branched or unbranched, substituted or unsubstituted.

As used herein, the term inorganic ligand refers to an inorganic chemical group which can bind to another atom or molecule through a non-carbon atom.

Examples of ligands include halogens, water, alcohols, ethers, hydroxyls, amides, carboxylates, chalcogenylates, thiocarboxylates, selenocarboxylates, tellurocarboxylates, carbonates, nitrates, phosphates, sulfates, perchlorates, oxalates, and amines.

As used herein, the term chalcogenylate refers to thiocarboxylate, selenocarboxylate, and tellurocarboxylate, having the formula RCE$_2^-$, where E is S, Se, or Te.

As used herein, the term chalcocarbamate refers to thiocarbamate, selenocarbamate, and tellurocarbamate, having the formula R$^1$R$^2$NCE$_2^-$, where E is S, Se, or Te, and R$^1$ and R$^2$ are the same or different and are hydrogen, alkyl, aryl, or an organic ligand.

Examples of ligands include F$^-$, Cl$^-$, H$_2$O, ROH, R$_2$O, OH$^-$, RO$^-$, NR$_2^-$, RCO$_2^-$, RCE$_2^-$, CO$_3^{2-}$, NO$_3^-$, PO$_4^{3-}$, SO$_4^{2-}$, ClO$_4^-$, C$_2$O$_4^{2-}$, NH$_3$, NR$_3$, R$_2$NH, and RNH$_2$, where R is alkyl, and E is chalcogen.

Examples of ligands include azides, heteroaryls, thiocyanates, arylamines, arylalkylamines, nitrites, and sulfites.

Examples of ligands include Br$^-$, N$_3^-$, pyridine, [SCN—]$^-$, ArNH$_2$, NO$_2^-$, and SO$_3^{2-}$ where Ar is aryl.

Examples of ligands include cyanides or nitriles, isocyanides or isonitriles, alkylcyanides, alkylnitriles, alkylisocyanides, alkylisonitriles, arylcyanides, arylnitriles, arylisocyanides, and arylisonitriles.

Examples of ligands include hydrides, carbenes, carbon monoxide, isocyanates, isonitriles, thiolates, alkylthiolates, dialkylthiolates, thioethers, thiocarbamates, phosphines, alkylphosphines, arylphosphines, arylalkylphosphines, arsenines, alkylarsenines, arylarsenines, arylalkylarsenines, stilbines, alkylstilbines, arylstilbines, and arylalkylstilbines.

Examples of ligands include I$^-$, H$^-$, R$^-$, —CN$^-$, —CO, RNC, RSH, R$_2$S, RS$^-$, —SCN$^-$, R$_3$P, R$_3$As, R$_3$Sb, alkenes, and aryls, where each R is independently alkyl, aryl, or heteroaryl.

Examples of ligands include trioctylphosphine, trimethylvinylsilane and hexafluoroacetylacetonate.

Examples of ligands include nitric oxide, silyls, alkylgermyls, arylgermyls, arylalkylgermyls, alkylstannyls, arylstannyls, arylalkylstannyls, selenocyanates, selenolates, alkylselenolates, dialkylselenolates, selenoethers, selenocarbamates, tellurocyanates, tellurolates, alkyltellurolates, dialkyltellurolates, telluroethers, and tellurocarbamates.

Examples of ligands include chalcogenates, thiothiolates, selenothiolates, thioselenolates, selenoselenolates, alkyl thiothiolates, alkyl selenothiolates, alkyl thioselenolates, alkyl selenoselenolates, aryl thiothiolates, aryl selenothiolates, aryl thioselenolates, aryl selenoselenolates, arylalkyl thiothiolates, arylalkyl selenothiolates, arylalkyl thioselenolates, and arylalkyl selenoselenolates.

Examples of ligands include selenoethers and telluroethers.

Examples of ligands include NO, $O^{2-}$, $NH_nR_{3-n}$, $PH_nR_{3-n}$, $SiR_3^-$, $GeR_3^-$, $SnR_3^-$, $^-SR$, $^-SeR$, $^-TeR$, $^-SSR$, $^-SeSR$, $^-SSeR$, $^-SeSeR$, and RCN, where n is from 1 to 3, and each R is independently alkyl or aryl.

As used herein, the term transition metals refers to atoms of Groups 3 though 12 of the Periodic Table of the elements recommended by the Commission on the Nomenclature of Inorganic Chemistry and published in *IUPAC Nomenclature of Inorganic Chemistry, Recommendations* 2005.

Photovoltaic Absorber Layer Compositions

A polymeric precursor may be used to prepare a material for use in developing semiconductor products.

The polymeric precursors of this invention may advantageously be used in mixtures to prepare a material with controlled or predetermined stoichiometric ratios of the metal atoms in the material.

In some aspects, processes for solar cells that avoid additional sulfurization or selenization steps may advantageously use polymeric precursor compounds and compositions of this invention.

The absorber material may be either an n-type or a p-type semiconductor, when such compound is known to exist.

In some embodiments, one or more polymeric precursor compounds may be used to prepare a CAIS layer on a substrate, wherein the layer has the empirical formula $(Cu_{1-x}Ag_x)_u In_v(S_{1-z}Se_z)_w$, where x is from 0.001 to 0.999, z is from 0 to 1, v is from 0.5 to 1.5, and w is from 1 to 3. In certain embodiments, x is from 0.001 to 1, or from 0.01 to 1, or from 0.02 to 1, or from 0.03 to 1, or from 0.05 to 1, or from 0.07 to 1, or from 0.1 to 1, or from 0.15 to 1, or from 0.2 to 1, or from 0.25 to 1, or from 0.3 to 1, or from 0.35 to 1, or from 0.4 to 1.

In some embodiments, one or more polymeric precursor compounds may be used to prepare a CAIS layer on a substrate, wherein the layer has the empirical formula $(Cu_{1-x}Ag_x)_u In_v(S_{1-z}Se_z)_w$, where x is from 0.001 to 0.999, z is from 0 to 1, v is from 0.7 to 1.2, and w is from 1 to 3.

In some embodiments, one or more polymeric precursor compounds may be used to prepare a CAIS layer on a substrate, wherein the layer has the empirical formula $(Cu_{1-x}Ag_x)_u In_v(S_{1-z}Se_z)_w$, where x is from 0.001 to 0.999, z is from 0 to 1, v is from 0.7 to 1.1, and w is from 1.5 to 2.5.

In some embodiments, one or more polymeric precursor compounds may be used to prepare a CAIS layer on a substrate, wherein the layer has the empirical formula $(Cu_{1-x}Ag_x)_u In_v(S_{1-z}Se_z)_w$, where x is from 0.001 to 0.999, z is from 0.5 to 1, v is from 0.7 to 1.1, and w is from 1.5 to 2.5.

In some embodiments, one or more polymeric precursor compounds may be used to prepare a CAIS layer on a substrate, wherein the layer has the empirical formula $(Cu_{1-x}Ag_x)_u In_v(S_{1-z}Se_z)_w$, where x is from 0.001 to 0.999, z is from 0.5 to 1, v is from 0.7 to 1.1, and w is from 1.5 to 2.5.

In some embodiments, one or more polymeric precursor compounds may be used to prepare an CAIS material having a quantity of Ag atoms of from 1 to 37.5 mol %, or from 2 to 37.5 mol %, or from 3 to 37.5 mol %, or from 5 to 37.5 mol %, or from 7 to 37.5 mol %, or from 10 to 37.5 mol %, or from 12 to 37.5 mol %.

In some embodiments, one or more polymeric precursor compounds may be used to prepare a CAIGS layer on a substrate, wherein the layer has the empirical formula $(Cu_{1-x}Ag_x)_u(In_{1-y}Ga_y)_v(S_{1-z}Se_z)_w$, where x is from 0.001 to 0.999, y is from 0 to 1, z is from 0 to 1, u is from 0.5 to 1.5, v is from 0.5 to 1.5, and w is from 1 to 3. In certain embodiments, x is from 0.001 to 1, or from 0.01 to 1, or from 0.02 to 1, or from 0.03 to 1, or from 0.05 to 1, or from 0.07 to 1, or from 0.1 to 1, or from 0.15 to 1, or from 0.2 to 1, or from 0.25 to 1, or from 0.3 to 1, or from 0.35 to 1, or from 0.4 to 1. In certain embodiments, x is from 0.001 to 1 and y is from 0.001 to 1, or x is from 0.01 to 1 and y is from 0.01 to 1, or x is from 0.02 to 1 and y is from 0.02 to 1, or x is from 0.03 to 1 and y is from 0.03 to 1, or x is from 0.05 to 1 and y is from 0.05 to 1, or x is from 0.07 to 1 and y is from 0.07 to 1, or x is from 0.1 to 1 and y is from 0.1 to 1, or x is from 0.15 to 1 and y is from 0.15 to 1, or x is from 0.2 to 1 and y is from 0.2 to 1, or x is from 0.25 to 1 and y is from 0.25 to 1, or x is from 0.3 to 1 and y is from 0.3 to 1, or x is from 0.35 to 1 and y is from 0.35 to 1, or x is from 0.4 to 1 and y is from 0.4 to 1.

In some embodiments, one or more polymeric precursor compounds may be used to prepare a CAIGS layer on a substrate, wherein the layer has the empirical formula $(Cu_{1-x}Ag_x)_u(In_{1-y}Ga_y)_v(S_{1-z}Se_z)_w$, where x is from 0.001 to 0.999, y is from 0 to 1, z is from 0 to 1, u is from 0.7 to 1.2, v is from 0.7 to 1.2, and w is from 1 to 3.

In some embodiments, one or more polymeric precursor compounds may be used to prepare a CAIGS layer on a substrate, wherein the layer has the empirical formula $(Cu_{1-x}Ag_x)_u(In_{1-y}Ga_y)_v(S_{1-z}Se_z)_w$, where x is from 0.001 to 0.999, y is from 0 to 1, z is from 0 to 1, u is from 0.7 to 1.1, v is from 0.7 to 1.1, and w is from 1.5 to 2.5.

In some embodiments, one or more polymeric precursor compounds may be used to prepare a CAIGS layer on a substrate, wherein the layer has the empirical formula $(Cu_{1-x}Ag_x)_u(In_{1-y}Ga_y)_v(S_{1-z}Se_z)_w$, where x is from 0.001 to 0.999, y is from 0 to 1, z is from 0.5 to 1, u is from 0.7 to 1.1, v is from 0.7 to 1.1, and w is from 1.5 to 2.5.

In some embodiments, one or more polymeric precursor compounds may be used to prepare a CAIGS layer on a substrate, wherein the layer has the empirical formula $(Cu_{1-x}Ag_x)_u(In_{1-y}Ga_y)_v(S_{1-z}Se_z)_w$, where x is from 0.001 to 0.999, y is from 0 to 1, z is from 0.5 to 1, u is from 0.8 to 0.95, v is from 0.7 to 1.1, and w is from 1.5 to 2.5.

In some embodiments, one or more polymeric precursor compounds may be used to prepare an CAIGS material having a quantity of Ag atoms of from 1 to 37.5 mol %, or from 2 to 37.5 mol %, or from 3 to 37.5 mol %, or from 5 to 37.5 mol %, or from 7 to 37.5 mol %, or from 10 to 37.5 mol %, or from 12 to 37.5 mol %.

A polymeric precursor may be used to prepare an absorber material for a solar cell product. The absorber material may have the empirical formula $M^A_u(M^B_{1-y}M^C_y)_v(S_{1-z}Se_z)_w$, where $M^A$ is Ag, $M^B$ and $M^C$ are Ga and In, respectively, u is from 0.5 to 1.5, y is from 0 to 1, and z is from 0 to 1, v is from 0.5 to 1.5, and w is from 1.5 to 2.5.

In some embodiments, one or more polymeric precursor compounds may be used to prepare a AIGS layer on a substrate, wherein the layer has the empirical formula $Ag_u(In_{1-y}Ga_y)_v(S_{1-z}Se_z)_w$, where u is from 0.5 to 1.5, y is from 0 to 1, and z is from 0 to 1, v is from 0.5 to 1.5, and w is from 1 to 3. In certain embodiments, u is from 0.5 to 1, or u is from 0.5 to 0.95, or u is from 1 to 1.5, or u is from 1.05 to 1.5, or u is from 1.1 to 1.5.

In some aspects, one or more polymeric precursor compounds may be used to prepare a AIGS layer on a substrate, wherein the layer has the empirical formula $Ag_u(In_{1-y}Ga_y)_v(S_{1-z}Se_z)_w$, where u is from 0.7 to 1.2, y is from 0 to 1, and z is from 0 to 1, v is from 0.7 to 1.2, and w is from 1 to 3.

In some variations, one or more polymeric precursor compounds may be used to prepare a AIGS layer on a substrate, wherein the layer has the empirical formula $Ag_u(In_{1-y}Ga_y)_v(S_{1-z}Se_z)_w$, where u is from 0.7 to 1.1, y is from 0 to 1, and z is from 0 to 1, v is from 0.7 to 1.1, and w is from 2 to 2.4.

In certain embodiments, one or more polymeric precursor compounds may be used to prepare a AIGS layer on a substrate, wherein the layer has the empirical formula $Ag_u(In_{1-y}Ga_y)_v(S_{1-z}Se_z)_w$, where u is from 0.7 to 1.1, y is from 0 to 1, and z is from 0.5 to 1, v is from 0.7 to 1.1, and w is from 2 to 2.4.

In certain embodiments, one or more polymeric precursor compounds may be used to prepare a AIGS layer on a substrate, wherein the layer has the empirical formula $Ag_u(In_{1-y}Ga_y)_v(S_{1-z}Se_z)_w$, where u is from 0.8 to 0.95, y is from 0.5 to 1, and z is from 0.5 to 1, v is from 0.95 to 1.05, and w is from 1.8 to 2.2.

In certain embodiments, one or more polymeric precursor compounds may be used to prepare a AIGS layer on a substrate, wherein the layer has the empirical formula $Ag_u(In_{1-y}Ga_y)_v(S_{1-z}Se_z)_w$, where u is from 0.8 to 0.95, y is from 0.5 to 1, and z is from 0.5 to 1, v is from 0.95 to 1.05, and w is from 2.0 to 2.2.

In some embodiments, one or more polymeric precursor compounds may be used to prepare an AIGS material having a quantity of Ag atoms of from 1 to 37.5 mol %, or from 2 to 37.5 mol %, or from 3 to 37.5 mol %, or from 5 to 37.5 mol %, or from 7 to 37.5 mol %, or from 10 to 37.5 mol %, or from 12 to 37.5 mol %.

Embodiments of this invention may further provide polymeric precursors that can be used to prepare a CAIGS, AIGS, CAIS, CAGS, AIS, or AGS material for a solar cell product.

In some aspects, one or more polymeric precursors may be used to prepare a CAIGS, AIGS, CAIS, CAGS, AIS, or AGS material as a chemically and physically uniform layer.

In some variations, one or more polymeric precursors may be used to prepare a CAIGS, AIGS, CAIS, CAGS, AIS, or AGS material wherein the stoichiometry of the metal atoms of the material can be controlled.

In certain variations, one or more polymeric precursors may be used to prepare a CAIGS, AIGS, CAIS, CAGS, AIS, or AGS material using nanoparticles prepared with the polymeric precursors.

In certain embodiments, one or more polymeric precursors may be used to prepare a CAIGS, AIGS, CAIS, CAGS, AIS, or AGS material as a layer that may be processed at relatively low temperatures to achieve a solar cell.

In some aspects, one or more polymeric precursors may be used to prepare a CAIGS, AIGS, CAIS, CAGS, AIS, or AGS material as a photovoltaic layer.

In some variations, one or more polymeric precursors may be used to prepare a chemically and physically uniform semiconductor CAIGS, AIGS, CAIS, CAGS, AIS, or AGS layer on a variety of substrates, including flexible substrates.

Examples of an absorber material include $AgGaS_2$, $AgInS_2$, $AgTlS_2$, $AgGaSe_2$, $AgInSe_2$, $AgTlSe_2$, $AgGaTe_2$, $AgInTe_2$, and $AgTlTe_2$.

Examples of an absorber material include AgInGaSSe, AgInTlSSe, AgGaTlSSe, AgInGaSeTe, AgInTlSeTe, AgGaTlSeTe, AgInGaSTe, AgInTlSTe, and AgGaTlSTe.

An CAIGS, AIGS, CAIS, CAGS, AIS, or AGS layer may be used with various junction partners to produce a solar cell. Examples of junction partner layers are known in the art and include CdS, ZnS, ZnSe, and CdZnS. See, for example, Martin Green, *Solar Cells: Operating Principles, Technology and System Applications* (1986); Richard H. Bube, *Photovoltaic Materials* (1998); Antonio Luque and Steven Hegedus, *Handbook of Photovoltaic Science and Engineering* (2003).

In some aspects, the thickness of an absorber layer may be from about 0.001 to about 100 micrometers, or from about 0.001 to about 20 micrometers, or from about 0.01 to about 10 micrometers, or from about 0.05 to about 5 micrometers, or from about 0.1 to about 4 micrometers, or from about 0.1 to about 3.5 micrometers, or from about 0.1 to about 3 micrometers, or from about 0.1 to about 2.5 micrometers.

Substrates

The polymeric precursors of this invention can be used to form a layer on a substrate. The substrate can be made of any substance, and can have any shape. Substrate layers of polymeric precursors can be used to create a photovoltaic layer or device.

Examples of substrates on which a polymeric precursor of this disclosure can be deposited or printed include semiconductors, doped semiconductors, silicon, gallium arsenide, insulators, glass, molybdenum glass, silicon dioxide, titanium dioxide, zinc oxide, silicon nitride, and combinations thereof.

A substrate may be coated with molybdenum or a molybdenum-containing compound.

In some embodiments, a substrate may be pre-treated with a molybdenum-containing compound, or one or more compounds containing molybdenum and selenium.

Examples of substrates on which a polymeric precursor of this disclosure can be deposited or printed include metals, metal foils, molybdenum, aluminum, beryllium, cadmium, cerium, chromium, cobalt, copper, gallium, gold, lead, manganese, nickel, palladium, platinum, rhenium, rhodium, silver, stainless steel, steel, iron, strontium, tin, titanium, tungsten, zinc, zirconium, metal alloys, metal silicides, metal carbides, and combinations thereof.

Examples of substrates on which a polymeric precursor of this disclosure can be deposited or printed include polymers, plastics, conductive polymers, copolymers, polymer blends, polyethylene terephthalates, polycarbonates, polyesters, polyester films, mylars, polyvinyl fluorides, polyvinylidene fluoride, polyethylenes, polyetherimides, polyethersulfones, polyetherketones, polyimides, polyvinylchlorides, acrylonitrile butadiene styrene polymers, silicones, epoxys, and combinations thereof.

Examples of substrates on which a polymeric precursor of this disclosure can be deposited or printed include roofing materials.

Examples of substrates on which a polymeric precursor of this disclosure can be deposited or printed include papers and coated papers.

A substrate of this disclosure can be of any shape. Examples of substrates on which a polymeric precursor of this disclosure can be deposited include a shaped substrate including a tube, a cylinder, a roller, a rod, a pin, a shaft, a plane, a plate, a blade, a vane, a curved surface or a spheroid.

A substrate may be layered with an adhesion promoter before the deposition, coating or printing of a layer of a polymeric precursor of this invention.

Examples of adhesion promoters include a glass layer, a metal layer, a titanium-containing layer, a tungsten-containing layer, a tantalum-containing layer, tungsten nitride, tantalum nitride, titanium nitride, titanium nitride silicide, tantalum nitride silicide, a chromium-containing layer, a vanadium-containing layer, a nitride layer, an oxide layer, a carbide layer, and combinations thereof.

Examples of adhesion promoters include organic adhesion promoters such as organofunctional silane coupling agents, silanes, hexamethyldisilazanes, glycol ether acetates, ethylene glycol bis-thioglycolates, acrylates, acrylics, mercaptans, thiols, selenols, tellurols, carboxylic acids, organic phosphoric acids, triazoles, and mixtures thereof.

Substrates may be layered with a barrier layer before the deposition of printing of a layer of a polymeric precursor of this invention.

Examples of a barrier layer include a glass layer, a metal layer, a titanium-containing layer, a tungsten-containing layer, a tantalum-containing layer, tungsten nitride, tantalum nitride, titanium nitride, titanium nitride silicide, tantalum nitride silicide, and combinations thereof.

A substrate can be of any thickness, and can be from about 20 micrometers to about 20,000 micrometers or more in thickness.

Ink Compositions

Embodiments of this invention further provide ink compositions which contain one or more polymeric precursor compounds. The polymeric precursors of this invention may be used to make photovoltaic materials by printing an ink onto a substrate.

An ink of this disclosure advantageously allows precise control of the stoichiometric ratios of certain atoms in the ink because the ink can be composed of a mixture of polymeric precursors.

Inks of this disclosure can be made by any methods known in the art.

In some embodiments, an ink can be made by mixing a polymeric precursor with one or more carriers. The ink may be a suspension of the polymeric precursors in an organic carrier. In some variations, the ink is a solution of the polymeric precursors in an organic carrier. The carrier can be an organic liquid or solvent.

An ink can be made by providing one or more polymeric precursor compounds and solubilizing, dissolving, solvating, or dispersing the compounds with one or more carriers. The compounds dispersed in a carrier may be nanocrystalline, nanoparticles, microparticles, amorphous, or dissolved molecules.

The concentration of the polymeric precursors in an ink of this disclosure can be from about 0.001% to about 99% (w/w), or from about 0.001% to about 90%, or from about 0.1% to about 90%.

A polymeric precursor may exist in a liquid or flowable phase under the temperature and conditions used for deposition, coating or printing.

In some variations of this invention, polymeric precursors that are partially soluble, or are insoluble in a particular carrier can be dispersed in the carrier by high shear mixing.

As used herein, the term dispersing encompasses the terms solubilizing, dissolving, and solvating.

The carrier for an ink of this disclosure may be an organic liquid or solvent. Examples of a carrier for an ink of this disclosure include one or more organic solvents, which may contain an aqueous component.

Embodiments of this invention further provide polymeric precursor compounds having enhanced solubility in one or more carriers for preparing inks. The solubility of a polymeric precursor compound can be selected by variation of the nature and molecular size and weight of one or more organic ligands attached to the compound.

An ink composition of this invention may contain any of the dopants disclosed herein, or a dopant known in the art.

Ink compositions of this disclosure can be made by methods known in the art, as well as methods disclosed herein.

Examples of a carrier for an ink of this disclosure include alcohol, methanol, ethanol, isopropyl alcohol, thiols, butanol, butanediol, glycerols, alkoxyalcohols, glycols, 1-methoxy-2-propanol, acetone, ethylene glycol, propylene glycol, propylene glycol laurate, ethylene glycol ethers, diethylene glycol, triethylene glycol monobutylether, propylene glycol monomethylether, 1,2-hexanediol, ethers, diethyl ether, aliphatic hydrocarbons, aromatic hydrocarbons, pentane, hexane, heptane, octane, isooctane, decane, cyclohexane, p-xylene, m-xylene, o-xylene, benzene, toluene, xylene, tetrahydrofuran, 2-methyltetrahydrofuran, siloxanes, cyclosiloxanes, silicone fluids, halogenated hydrocarbons, dibromomethane, dichloromethane, dichloroethane, trichloroethane chloroform, methylene chloride, acetonitrile, esters, acetates, ethyl acetate, butyl acetate, acrylates, isobornyl acrylate, 1,6-hexanediol diacrylate, polyethylene glycol diacrylate, ketones, acetone, methyl ethyl ketone, cyclohexanone, butyl carbitol, cyclopentanone, lactams, N-methylpyrrolidone, N-(2-hydroxyethyl)-pyrrolidone, cyclic acetals, cyclic ketals, aldehydes, amides, dimethylformamide, methyl lactate, oils, natural oils, terpenes, and mixtures thereof.

An ink of this disclosure may further include components such as a surfactant, a dispersant, an emulsifier, an anti-foaming agent, a dryer, a filler, a resin binder, a thickener, a viscosity modifier, an anti-oxidant, a flow agent, a plasticizer, a conductivity agent, a crystallization promoter, an extender, a film conditioner, an adhesion promoter, and a dye. Each of these components may be used in an ink of this disclosure at a level of from about 0.001% to about 10% or more of the ink composition.

Examples of surfactants include siloxanes, polyalkyleneoxide siloxanes, polyalkyleneoxide polydimethylsiloxanes, polyester polydimethylsiloxanes, ethoxylated nonylphenols, nonylphenoxy polyethyleneoxyethanol, fluorocarbon esters, fluoroaliphatic polymeric esters, fluorinated esters, alkylphenoxy alkyleneoxides, cetyl trimethyl ammonium chloride, carboxymethylamylose, ethoxylated acetylene glycols, betaines, N-n-dodecyl-N,N-dimethylbetaine, dialkyl sulfosuccinate salts, alkylnaphthalenesulfonate salts, fatty acid salts, polyoxyethylene alkylethers, polyoxyethylene alkylallylethers, polyoxyethylene-polyoxypropylene block copolymers, alkylamine salts, quaternary ammonium salts, and mixtures thereof.

Examples of surfactants include anionic, cationic, amphoteric, and nonionic surfactants. Examples of surfactants include SURFYNOL, DYNOL, ZONYL, FLUORAD, and SILWET surfactants.

A surfactant may be used in an ink of this disclosure at a level of from about 0.001% to about 2% of the ink composition.

Examples of a dispersant include a polymer dispersant, a surfactant, hydrophilic-hydrophobic block copolymers, acrylic block copolymers, acrylate block copolymers, graft polymers, and mixtures thereof.

Examples of an emulsifier include a fatty acid derivative, an ethylene stearamide, an oxidized polyethylene wax, mineral oils, a polyoxyethylene alkyl phenol ether, a polyoxyethylene glycol ether block copolymer, a polyoxyethylene sorbitan fatty acid ester, a sorbitan, an alkyl siloxane polyether polymer, polyoxyethylene monostearates, polyoxyethylene monolaurates, polyoxyethylene monooleates, and mixtures thereof.

Examples of an anti-foaming agent include polysiloxanes, dimethylpolysiloxanes, dimethyl siloxanes, silicones, polyethers, octyl alcohol, organic esters, ethyleneoxide propyleneoxide copolymers, and mixtures thereof.

Examples of a dryer include aromatic sulfonic acids, aromatic carboxylic acids, phthalic acid, hydroxyisophthalic acid, N-phthaloylglycine, 2-Pyrrolidone 5-carboxylic acid, and mixtures thereof.

Examples of a filler include metallic fillers, silver powder, silver flake, metal coated glass spheres, graphite powder, carbon black, conductive metal oxides, ethylene vinyl acetate polymers, and mixtures thereof.

Examples of a resin binder include acrylic resins, alkyd resins, vinyl resins, polyvinyl pyrrolidone, phenolic resins, ketone resins, aldehyde resins, polyvinyl butyral resin, amide resins, amino resins, acrylonitrile resins, cellulose resins, nitrocellulose resins, rubbers, fatty acids, epoxy resins, ethylene acrylic copolymers, fluoropolymers, gels, glycols, hydrocarbons, maleic resins, urea resins, natural rubbers, natural gums, phenolic resins, cresols, polyamides, polybutadienes, polyesters, polyolefins, polyurethanes, isocynates, polyols, thermoplastics, silicates, silicones, polystyrenes, and mixtures thereof.

Examples of thickeners and viscosity modifiers include conducting polymers, celluloses, urethanes, polyurethanes, styrene maleic anhydride copolymers, polyacrylates, polycarboxylic acids, carboxymethylcelluoses, hydroxyethylcelluloses, methylcelluloses, methyl hydroxyethyl celluloses, methyl hydroxypropyl celluloses, silicas, gellants, aluminates, titanates, gums, clays, waxes, polysaccharides, starches, and mixtures thereof.

Examples of anti-oxidants include phenolics, phosphites, phosphonites, thioesters, stearic acids, ascorbic acids, catechins, cholines, and mixtures thereof.

Examples of flow agents include waxes, celluloses, butyrates, surfactants, polyacrylates, and silicones.

Examples of a plasticizer include alkyl benzyl phthalates, butyl benzyl phthalates, dioctyl phthalates, diethyl phthalates, dimethyl phthalates, di-2-ethylhexy-adipates, diisobutyl phthalates, diisobutyl adipates, dicyclohexyl phthalates, glycerol tribenzoates, sucrose benzoates, polypropylene glycol dibenzoates, neopentyl glycol dibenzoates, dimethyl isophthalates, dibutyl phthalates, dibutyl sebacates, tri-n-hexyltrimellitates, and mixtures thereof.

Examples of a conductivity agent include lithium salts, lithium trifluoromethanesulfonates, lithium nitrates, dimethylamine hydrochlorides, diethylamine hydrochlorides, hydroxylamine hydrochlorides, and mixtures thereof.

Examples of a crystallization promoter include copper chalcogenides, alkali metal chalcogenides, alkali metal salts, alkaline earth metal salts, sodium chalcogenates, cadmium salts, cadmium sulfates, cadmium sulfides, cadmium selenides, cadmium tellurides, indium sulfides, indium selenides, indium tellurides, gallium sulfides, gallium selenides, gallium tellurides, molybdenum, molybdenum sulfides, molybdenum selenides, molybdenum tellurides, molybdenum-containing compounds, and mixtures thereof.

An ink may contain one or more components selected from the group of a conducting polymer, silver metal, silver selenide, silver sulfide, copper metal, indium metal, gallium metal, zinc metal, alkali metals, alkali metal salts, alkaline earth metal salts, sodium chalcogenates, calcium chalcogenates, cadmium sulfide, cadmium selenide, cadmium telluride, indium sulfide, indium selenide, indium telluride, gallium sulfide, gallium selenide, gallium telluride, zinc sulfide, zinc selenide, zinc telluride, copper sulfide, copper selenide, copper telluride, molybdenum sulfide, molybdenum selenide, molybdenum telluride, and mixtures of any of the foregoing.

An ink of this disclosure may contain particles of a metal, a conductive metal, or an oxide. Examples of metal and oxide particles include silica, alumina, titania, copper, iron, steel, aluminum and mixtures thereof.

In certain variations, an ink may contain a biocide, a sequestering agent, a chelator, a humectant, a coalescent, or a viscosity modifier.

In certain aspects, an ink of this disclosure may be formed as a solution, a suspension, a slurry, or a semisolid gel or paste. An ink may include one or more polymeric precursors solubilized in a carrier, or may be a solution of the polymeric precursors. In certain variations, a polymeric precursor may include particles or nanoparticles that can be suspended in a carrier, and may be a suspension or paint of the polymeric precursors. In certain embodiments, a polymeric precursor can be mixed with a minimal amount of a carrier, and may be a slurry or semisolid gel or paste of the polymeric precursor.

The viscosity of an ink of this disclosure can be from about 0.5 centipoises (cP) to about 50 cP, or from about 0.6 to about 30 cP, or from about 1 to about 15 cP, or from about 2 to about 12 cP.

The viscosity of an ink of this disclosure can be from about 20 cP to about $2 \times 10^6$ cP, or greater. The viscosity of an ink of this disclosure can be from about 20 cP to about $1 \times 10^6$ cP, or from about 200 cP to about 200,000 cP, or from about 200 cP to about 100,000 cP, or from about 200 cP to about 40,000 cP, or from about 200 cP to about 20,000 cP.

The viscosity of an ink of this disclosure can be about 1 cP, or about 2 cP, or about 5 cP, or about 20 cP, or about 100 cP, or about 500 cP, or about 1,000 cP, or about 5,000 cP, or about 10,000 cP, or about 20,000 cP, or about 30,000 cP, or about 40,000 cP.

In some embodiments, an ink may contain one or more components from the group of a surfactant, a dispersant, an emulsifier, an anti-foaming agent, a dryer, a filler, a resin binder, a thickener, a viscosity modifier, an anti-oxidant, a flow agent, a plasticizer, a conductivity agent, a crystallization promoter, an extender, a film conditioner, an adhesion promoter, and a dye. In certain variations, an ink may contain one or more compounds from the group of cadmium sulfide, cadmium selenide, cadmium telluride, zinc sulfide, zinc selenide, zinc telluride, copper sulfide, copper selenide, and copper telluride. In some aspects, an ink may contain particles of a metal, a conductive metal, or an oxide.

An ink may be made by dispersing one or more polymeric precursor compounds of this disclosure in one or more carriers to form a dispersion or solution.

A polymeric precursor ink composition can be prepared by dispersing one or more polymeric precursors in a solvent, and heating the solvent to dissolve or disperse the polymeric precursors. The polymeric precursors may have a concentration of from about 0.001% to about 99% (w/w), or from about 0.001% to about 90%, or from about 0.1% to about 90%, or from about 0.1% to about 50%, or from about 0.1% to about 40%, or from about 0.1% to about 30%, or from about 0.1% to about 20%, or from about 0.1% to about 10% in the solution or dispersion.

Processes for Films of Polymeric Precursors on Substrates

The polymeric precursors of this invention can be used to make photovoltaic materials by depositing a layer onto a substrate, where the layer contains one or more polymeric precursors. The deposited layer may be a film or a thin film. Substrates are described above.

As used herein, the terms "deposit," "depositing," and "deposition" refer to any method for placing a compound or composition onto a surface or substrate, including spraying, coating, and printing.

As used herein, the term "thin film" refers to a layer of atoms or molecules, or a composition layer on a substrate having a thickness of less than about 300 micrometers.

A deposited layer of this disclosure advantageously allows precise control of the stoichiometric ratios of certain atoms in the layer because the layer can be composed of a mixture of polymeric precursors.

The polymeric precursors of this invention, and compositions containing polymeric precursors, can be deposited onto a substrate using methods known in the art, as well as methods disclosed herein.

Examples of methods for depositing a polymeric precursor onto a surface or substrate include all forms of spraying, coating, and printing.

Solar cell layers can be made by depositing one or more polymeric precursors of this disclosure on a flexible substrate in a high throughput roll process. The depositing of polymeric precursors in a high throughput roll process can be done by spraying or coating a composition containing one or more polymeric precursors, or by printing an ink containing one or more polymeric precursors of this disclosure.

Examples of methods for depositing a polymeric precursor onto a surface or substrate include spraying, spray coating, spray deposition, spray pyrolysis, and combinations thereof.

Examples of methods for printing using an ink of this disclosure include printing, screen printing, inkjet printing, aerosol jet printing, ink printing, jet printing, stamp/pad printing, transfer printing, pad printing, flexographic printing, gravure printing, contact printing, reverse printing, thermal printing, lithography, electrophotographic printing, and combinations thereof.

Examples of methods for depositing a polymeric precursor onto a surface or substrate include electrodepositing, electroplating, electroless plating, bath deposition, coating, dip coating, wet coating, spin coating, knife coating, roller coating, rod coating, slot die coating, meyerbar coating, lip direct coating, capillary coating, liquid deposition, solution deposition, layer-by-layer deposition, spin casting, and solution casting.

Examples of methods for depositing a polymeric precursor onto a surface or substrate include chemical vapor deposition, aerosol chemical vapor deposition, metal-organic chemical vapor deposition, organometallic chemical vapor deposition, plasma enhanced chemical vapor deposition, and combinations thereof.

Examples of methods for depositing a polymeric precursor onto a surface or substrate include atomic layer deposition, plasma-enhanced atomic layer deposition, vacuum chamber deposition, sputtering, RF sputtering, DC sputtering, magnetron sputtering, evaporation, electron beam evaporation, laser ablation, gas-source polymeric beam epitaxy, vapor phase epitaxy, liquid phase epitaxy, and combinations thereof.

In certain embodiments, a first polymeric precursor may be deposited onto a substrate, and subsequently a second polymeric precursor may be deposited onto the substrate. In certain embodiments, several different polymeric precursors may be deposited onto the substrate to create a layer.

In certain variations, different polymeric precursors may be deposited onto a substrate simultaneously, or sequentially, whether by spraying, coating, printing, or by other methods. The different polymeric precursors may be contacted or mixed before the depositing step, during the depositing step, or after the depositing step. The polymeric precursors can be contacted before, during, or after the step of transporting the polymeric precursors to the substrate surface.

The depositing of polymeric precursors, including by spraying, coating, and printing, can be done in a controlled or inert atmosphere, such as in dry nitrogen and other inert gas atmospheres, as well as in a partial vacuum atmosphere.

Processes for depositing, spraying, coating, or printing polymeric precursors can be done at various temperatures including from about −20° C. to about 650° C., or from about −20° C. to about 600° C., or from about −20° C. to about 400° C., or from about 20° C. to about 360° C., or from about 20° C. to about 300° C., or from about 20° C. to about 250° C.

Processes for making a solar cell involving a step of transforming a polymeric precursor compound into a material or semiconductor can be performed at various temperatures including from about 100° C. to about 650° C., or from about 150° C. to about 650° C., or from about 250° C. to about 650° C., or from about 300° C. to about 650° C., or from about 400° C. to about 650° C., or from about 300° C. to about 600° C., or from about 300° C. to about 550° C., or from about 300° C. to about 500° C., or from about 300° C. to about 450° C.

In certain aspects, depositing of polymeric precursors on a substrate can be done while the substrate is heated. In these variations, a thin-film material may be deposited or formed on the substrate.

In some embodiments, a step of converting a precursor to a material and a step of annealing can be done simultaneously. In general, a step of heating a precursor can be done before, during or after any step of depositing the precursor.

In some variations, a substrate can be cooled after a step of heating. In certain embodiments, a substrate can be cooled before, during, or after a step of depositing a precursor. A substrate may be cooled to return the substrate to a lower temperature, or to room temperature, or to an operating temperature of a deposition unit. Various coolants or cooling methods can be applied to cool a substrate.

The depositing of polymeric precursors on a substrate may be done with various apparatuses and devices known in art, as well as devices described herein.

In some variations, the depositing of polymeric precursors can be performed using a spray nozzle with adjustable nozzle dimensions to provide a uniform spray composition and distribution.

Embodiments of this disclosure further contemplate articles made by depositing a layer onto a substrate, where the layer contains one or more polymeric precursors. The article may be a substrate having a layer of a film, or a thin film, which is deposited, sprayed, coated, or printed onto the substrate. In certain variations, an article may have a substrate printed with a polymeric precursor ink, where the ink is printed in a pattern on the substrate.

Photovoltaic Devices

The polymeric precursors of this invention can be used to make photovoltaic materials and solar cells of high efficiency.

Figure 6:
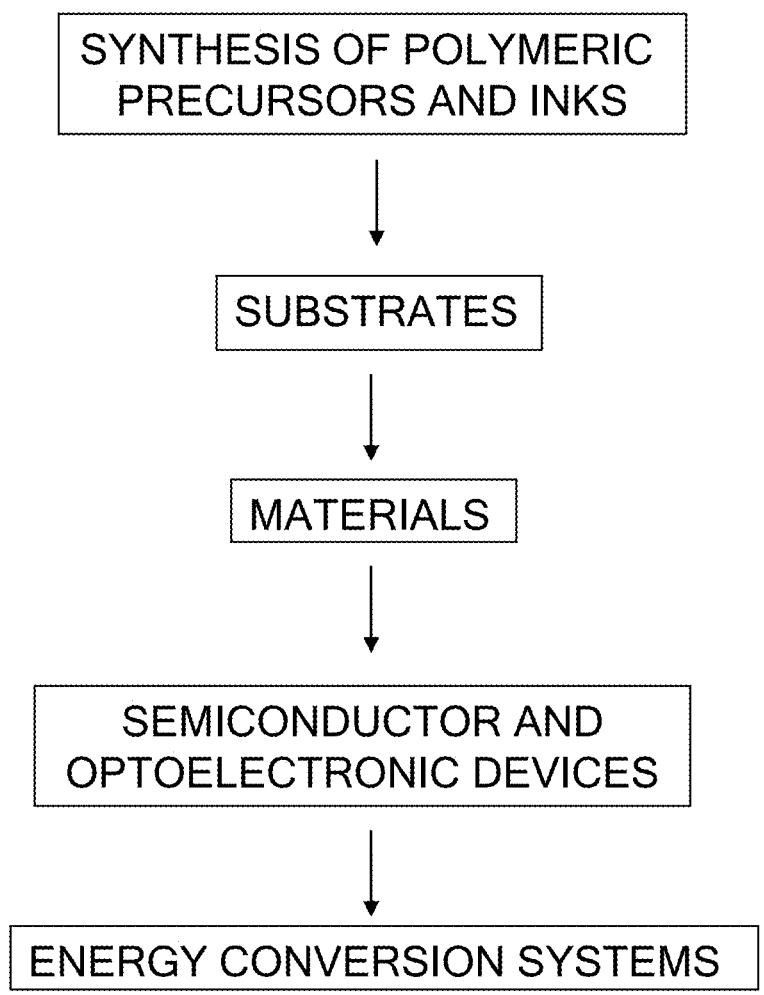
FIG. 6 Schematic representation of embodiments of this invention in which polymeric precursors and ink compositions are deposited onto particular substrates by methods including spraying, coating, and printing, and are used to make semiconductor and optoelectronic materials and devices, as well as energy conversion systems.

As shown in FIG. 6, embodiments of this invention may further provide optoelectronic devices and energy conversion systems. Following the synthesis of polymeric precursor compounds, the compounds can be sprayed, deposited, or printed onto substrates and formed into absorber materials and semiconductor layers. Absorber materials can be the basis for optoelectronic devices and energy conversion systems.

In some embodiments, the solar cell is a thin layer solar cell having a CAIGS, AIGS, CAIS, CAGS, AIS, or AGS absorber layer deposited or printed on a substrate.

Embodiments of this invention may provide improved efficiency for solar cells used for light to electricity conversion.

In some embodiments, a solar cell of this disclosure is a heterojunction device made with a CAIGS, AIGS, CAIS, CAGS, AIS, or AGS cell. The CAIGS, AIGS, CAIS, CAGS, AIS, or AGS layer may be used as a junction partner with a layer of, for example, cadmium sulfide, cadmium selenide, cadmium telluride, zinc sulfide, zinc selenide, or zinc telluride. The absorber layer may be adjacent to a layer of MgS, MgSe, MgTe, HgS, HgSe, HgTe, AlN, AlP, AlAs, AlSb, GaN, GaP, GaAs, GaSb, InN, InP, InAs, InSb, or combinations thereof.

In certain variations, a solar cell of this disclosure is a multijunction device made with one or more stacked solar cells.

Figure 7:
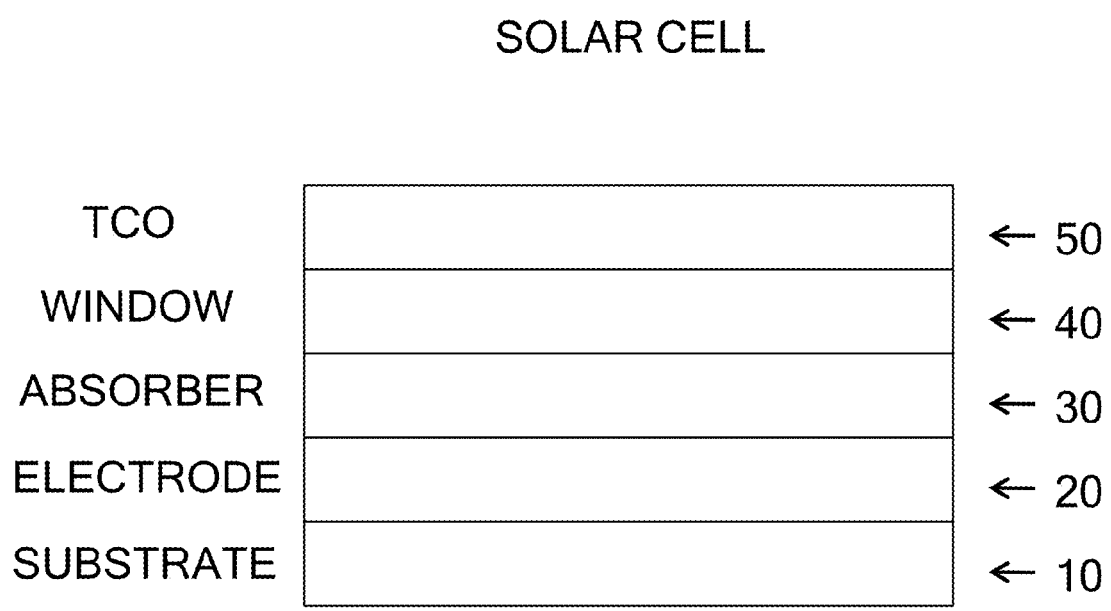
FIG. 7 Schematic representation of a solar cell embodiment of this invention.

As shown in FIG. 7, a solar cell device of this disclosure may have a substrate 10, an electrode layer 20, an absorber layer 30, a window layer 40, and a transparent conductive layer (TCO) 50. The substrate 10 may be metal, plastic, glass, or ceramic. The electrode layer 20 can be a molybdenum-containing layer. The absorber layer 30 may be a CAIGS, AIGS, CAIS, CAGS, AIS, or AGS layer. The window layer 40 may be a cadmium sulfide layer. The transparent conductive layer 50 can be an indium tin oxide layer or a doped zinc oxide layer.

A solar cell device of this disclosure may have a substrate, an electrode layer, an absorber layer, a window layer, an adhesion promoting layer, a junction partner layer, a transparent layer, a transparent electrode layer, a transparent conductive oxide layer, a transparent conductive polymer layer, a doped conductive polymer layer, an encapsulating layer, an anti-reflective layer, a protective layer, or a protective polymer layer. In certain variations, an absorber layer includes a plurality of absorber layers.

In certain variations, solar cells may be made by processes using polymeric precursor compounds and compositions of this invention that advantageously avoid additional sulfurization or selenization steps.

In certain variations, a solar cell device may have a molybdenum-containing layer, or an interfacial molybdenum-containing layer.

Examples of a protective polymer include silicon rubbers, butyryl plastics, ethylene vinyl acetates, and combinations thereof.

Substrates can be made of a flexible material which can be handled in a roll. The electrode layer may be a thin foil.

Absorber layers of this disclosure can be made by depositing or printing a composition containing nanoparticles onto a substrate, where the nanoparticles can be made with polymeric precursor compounds of this invention. In some processes, nanoparticles can be made with, or formed from polymeric precursor compounds and deposited on a substrate. Deposited nanoparticles can subsequently be transformed by the application of heat or energy.

In some embodiments, the absorber layer may be formed from nanoparticles or semiconductor nanoparticles which have been deposited on a substrate and subsequently transformed by heat or energy.

In some embodiments, a thin film photovoltaic device may have a transparent conductor layer, a buffer layer, a p-type absorber layer, an electrode layer, and a substrate. The transparent conductor layer may be a transparent conductive oxide (TCO) layer such as a zinc oxide layer, or zinc oxide layer doped with aluminum, or a carbon nanotube layer, or a tin oxide layer, or a tin oxide layer doped with fluorine, or an indium tin oxide layer, or an indium tin oxide layer doped with fluorine, while the buffer layer can be cadmium sulfide, or cadmium sulfide and high resistivity zinc oxide. The p-type absorber layer can be a CAIGS, AIGS, CAIS, CAGS, AIS, or AGS layer, and the electrode layer can be molybdenum. The transparent conductor layer can be up to about 0.5 micrometers in thickness. The buffer layer can also be a cadmium sulfide n-type junction partner layer. In some embodiments, the buffer layer may be a silicon dioxide, an aluminum oxide, a titanium dioxide, or a boron oxide.

Some examples of transparent conductive oxides are given in K. Ellmer et al., Transparent Conductive Zinc Oxide, Vol. 104, Springer Series in Materials Science (2008).

In some aspects, a solar cell can include a molybdenum selenide interface layer, which may be formed using various molybdenum-containing and selenium-containing compounds that can be added to an ink for printing, or deposited onto a substrate.

A thin film material photovoltaic absorber layer can be made with one or more polymeric precursors of this invention. For example, a polymeric precursor ink can be sprayed onto a stainless steel substrate using a spray pyrolysis unit in a glovebox in an inert atmosphere. The spray pyrolysis unit may have an ultrasonic nebulizer, precision flow meters for inert gas carrier, and a tubular quartz reactor in a furnace. The spray-coated substrate can be heated at a temperature of from about 25° C. to about 650° C. in an inert atmosphere, thereby producing a thin film material photovoltaic absorber layer.

In some examples, a thin film material photovoltaic absorber layer can be made by providing a polymeric precursor ink which is filtered with a 0.45 micron filter, or a 0.3 micron filter. The ink can be deposited onto an aluminum substrate using a spin casting unit in a glovebox in inert argon atmosphere. The substrate can be spin coated with the polymeric precursor ink to a film thickness of about 0.1 to 5 microns. The substrate can be removed and heated at a temperature of from about 100° C. to about 600° C., or from about 100° C. to about 650° C. in an inert atmosphere, thereby producing a thin film material photovoltaic absorber layer.

In further examples, a thin film material photovoltaic absorber layer can be made by providing a polymeric precursor ink which is filtered with a 0.45 micron filter, or a 0.3 micron filter. The ink may be printed onto a polyethylene terephthalate substrate using a inkjet printer in a glovebox in an inert atmosphere. A film of about 0.1 to 5 microns thickness can be deposited on the substrate. The substrate can be removed and heated at a temperature of from about 100° C. to about 600° C., or from about 100° C. to about 650° C. in an inert atmosphere, thereby producing a thin film material photovoltaic absorber layer.

In some examples, a solar cell can be made by providing an electrode layer on a polyethylene terephthalate substrate. A thin film material photovoltaic absorber layer can be coated onto the electrode layer as described above. A window layer can be deposited onto the absorber layer. A transparent conductive oxide layer can be deposited onto the window layer, thereby forming an embodiment of a solar cell.

Methods for making a photovoltaic absorber layer on a substrate include providing one or more polymeric precursor compounds, providing a substrate, spraying the compounds onto the substrate, and heating the substrate at a temperature of from about 100° C. to about 600° C., or of from about 100° C. to about 650° C. in an inert atmosphere, thereby producing a photovoltaic absorber layer having a thickness of from 0.001 to 100 micrometers. The spraying can be done in spray coating, spray deposition, jet deposition, or spray pyrolysis. The substrate may be glass, metal, polymer, plastic, or silicon.

In certain variations, methods for making a photovoltaic absorber layer may include heating the compounds to a temperature of from about 20° C. to about 400° C. while depositing, spraying, coating, or printing the compounds onto the substrate.

Methods for making a photovoltaic absorber layer on a substrate include providing one or more polymeric precursor compounds, providing a substrate, depositing the compounds onto the substrate, and heating the substrate at a temperature of from about 100° C. to about 650° C., or from about 100° C. to about 600° C., or from about 100° C. to about 400° C., or from about 100° C. to about 300° C. in an inert atmosphere, thereby producing a photovoltaic absorber layer having a thickness of from 0.001 to 100 micrometers. The depositing can be done in electrodepositing, electroplating, electroless plating, bath deposition, liquid deposition, solution deposition, layer-by-layer deposition, spin casting, or solution casting. The substrate may be glass, metal, polymer, plastic, or silicon.

Methods for making a photovoltaic absorber layer on a substrate include providing one or more polymeric precursor inks, providing a substrate, printing the inks onto the substrate, and heating the substrate at a temperature of from about 100° C. to about 600° C., or from about 100° C. to about 650° C. in an inert atmosphere, thereby producing a photovoltaic absorber layer having a thickness of from 0.001 to 100 micrometers. The printing can be done in screen printing, inkjet printing, transfer printing, flexographic printing, or gravure printing. The substrate may be glass, metal, polymer, plastic, or silicon. The method may further include adding to the ink an additional indium-containing compound, such as $In(SeR)_3$, wherein R is alkyl or aryl.

Electrical Power Generation and Transmission

This disclosure contemplates methods for producing and delivering electrical power. A photovoltaic device of this invention can be used, for example, to convert solar light to electricity which can be provided to a commercial power grid.

As used herein, the term "solar cell" refers to individual solar cell as well as a solar cell array, which can combine a number of solar cells.

Solar cell devices can be manufactured in modular panels.

The power systems of this disclosure can be made in large or small scale, including power for a personal use, as well as on a megawatt scale for a public use.

An important feature of the solar cell devices and power systems of this disclosure is that they can be manufactured and used with low environmental impact.

A power system of this disclosure may utilize a solar cell on a movable mounting, which may be motorized to face the solar cell toward the light. Alternatively, a solar cell may be mounted on a fixed object in an optimal orientation.

Solar cells can be attached in panels in which various groups of cells are electrically connected in series and in parallel to provide suitable voltage and current characteristics.

Solar cells can be installed on rooftops, as well as outdoor, sunlighted surfaces of all kinds Solar cells can be combined with various kinds of roofing materials such as roofing tiles or shingles.

A power system can include a solar cell array and a battery storage system. A power system may have a diode-containing circuit and a voltage-regulating circuit to prevent the battery storage system from draining through the solar cells or from being overcharged.

A power system can be used to provide power for lighting, electric vehicles, electric buses, electric airplanes, pumping water, desalinization of water, refrigeration, milling, manufacturing, and other uses.

Sources of Elements

Sources of silver include silver metal, Ag(I), silver nitrates, silver halides, silver chlorides, silver acetates, silver alkoxides, and mixtures thereof.

Sources of copper include copper metal, Cu(I), Cu(II), copper halides, copper chlorides, copper acetates, copper alkoxides, copper alkyls, copper diketonates, copper 2,2,6,6,-tetramethyl-3,5,-heptanedionate, copper 2,4-pentanedionate, copper hexafluoroacetylacetonate, copper acetylacetonate, copper dimethylaminoethoxide, copper ketoesters, and mixtures thereof.

Sources of indium include indium metal, trialkylindium, trisdialkylamineindium, indium halides, indium chlorides, dimethylindium chlorides, trimethylindium, indium acetylacetonates, indium hexafluoropentanedionates, indium methoxyethoxides, indium methyltrimethylacetylacetates, indium trifluoropentanedionates, and mixtures thereof.

Sources of gallium include gallium metal, trialkylgallium, trisdialkylamine gallium, gallium halides, gallium fluorides, gallium chlorides, gallium iodides, diethylgallium chlorides, gallium acetate, gallium 2,4-pentanedionate, gallium ethoxide, gallium 2,2,6,6,-tetramethylheptanedionate, trisdimethylaminogallium, and mixtures thereof.

Some sources of gallium and indium are described in International Patent Publication No. WO2008057119.

Additional Sulfurization or Selenization

In various processes of this disclosure, a composition or material may optionally be subjected to a step of sulfurization or selenization.

Sulfurization with $H_2S$ or selenization with $H_2Se$ may be carried out by using pure $H_2S$ or $H_2Se$, respectively, or may be done by dilution in hydrogen or in nitrogen. Selenization can also be carried out with Se vapor, or other source of elemental selenium.

A sulfurization or selenization step can be done at any temperature from about 200° C. to about 650° C., or at temperatures below 200° C. One or more steps of sulfurization and selenization may be performed concurrently, or sequentially.

Examples of sulfurizing agents include hydrogen sulfide, hydrogen sulfide diluted with hydrogen, elemental sulfur, sulfur powder, carbon disulfide, alkyl polysulfides, dimethyl sulfide, dimethyl disulfide, and mixtures thereof.

Examples of selenizing agents include hydrogen selenide, hydrogen selenide diluted with hydrogen, elemental selenium, selenium powder, carbon diselenide, alkyl polyselenides, dimethyl selenide, dimethyl diselenide, and mixtures thereof.

A sulfurization or selenization step can also be done with co-deposition of another metal such as copper, indium, or gallium.

Chemical Definitions

As used herein, the term (X,Y) when referring to compounds or atoms indicates that either X or Y, or a combination thereof may be found in the formula. For example, (S,Se) indicates that atoms of either sulfur or selenium, or any combination thereof may be found. Further, using this notation the amount of each atom can be specified. For example, when appearing in the chemical formula of a molecule, the notation (0.75 In,0.25 Ga) indicates that the atom specified by the symbols in the parentheses is indium in 75% of the compounds and gallium in the remaining 25% of the compounds, regardless of the identity any other atoms in the compound. In the absence of a specified amount, the term (X,Y) refers to approximately equal amounts of X and Y.

The atoms S, Se, and Te of Group 16 are referred to as chalcogens.

As used herein, the letter "S" in CIGS, AIGS, CAIGS, refers to sulfur or selenium or both. The letter "C" in CIGS and CAIGS refers to copper. The letter "A" in AIGS and CAIGS which appears before the letters I and G refers to silver. The letter "I" in CIGS, AIGS, and CAIGS refers to indium. The letter "G" in CIGS, AIGS, and CAIGS refers to gallium.

As used herein, the terms CIGS, AIGS, and CAIGS include the variations C(I,G)S, A(I,G)S, and CA(I,G)S, respectively, and CIS, AIS, and CAIS, respectively, as well as CGS, AGS, and CAGS, respectively, unless described otherwise.

As used herein, the term CIGS includes the terms CIGSSe and CIGSe, and these terms refer to compounds or materials containing copper/indium/gallium/sulfur/selenium, which may contain sulfur or selenium or both. The term AIGS includes the terms AIGSSe and AIGSe, and these terms refer to compounds or materials containing silver/indium/gallium/sulfur/selenium, which may contain sulfur or selenium or both. The term CAIGS includes the terms CAIGSSe and CAIGSe, and these terms refer to compounds or materials containing copper/silver/indium/gallium/sulfur/selenium, which may contain sulfur or selenium or both.

As used herein, the term "chalcogenide" refers to a compound containing one or more chalcogen atoms bonded to one or more metal atoms.

The term "alkyl" as used herein refers to a hydrocarbyl radical of a saturated aliphatic group, which can be a branched or unbranched, substituted or unsubstituted aliphatic group containing from 1 to 22 carbon atoms. This definition applies to the alkyl portion of other groups such as, for example, cycloalkyl, alkoxy, alkanoyl, aralkyl, and other groups defined below. The term "cycloalkyl" as used herein refers to a saturated, substituted or unsubstituted cyclic alkyl ring containing from 3 to 12 carbon atoms. As used herein, the term "C(1-5)alkyl" includes C(1)alkyl, C(2)alkyl, C(3)alkyl, C(4)alkyl, and C(5)alkyl. Likewise, the term "C(3-22)alkyl" includes C(1)alkyl, C(2)alkyl, C(3)alkyl, C(4)alkyl, C(5)alkyl, C(6)alkyl, C(7)alkyl, C(8)alkyl, C(9)alkyl, C(10)alkyl, C(11)alkyl, C(12)alkyl, C(13)alkyl, C(14)alkyl, C(15)alkyl, C(16)alkyl, C(17)alkyl, C(18)alkyl, C(19)alkyl, C(20)alkyl, C(21)alkyl, and C(22)alkyl.

The term "alkenyl" as used herein refers to an unsaturated, branched or unbranched, substituted or unsubstituted alkyl or cycloalkyl having 2 to 22 carbon atoms and at least one carbon-carbon double bond. The term "alkynyl" as used herein refers to an unsaturated, branched or unbranched, substituted or unsubstituted alkyl or cycloalkyl having 2 to 22 carbon atoms and at least one carbon-carbon triple bond.

The term "alkoxy" as used herein refers to an alkyl, cycloalkyl, alkenyl, or alkynyl group covalently bonded to an oxygen atom. The term "alkanoyl" as used herein refers to —C(=O)-alkyl, which may alternatively be referred to as "acyl." The term "alkanoyloxy" as used herein refers to —O—C(=O)-alkyl groups. The term "alkylamino" as used herein refers to the group —NRR', where R and R' are each either hydrogen or alkyl, and at least one of R and R' is alkyl. Alkylamino includes groups such as piperidino wherein R and R' form a ring. The term "alkylaminoalkyl" refers to -alkyl-NRR'.

The term "aryl" as used herein refers to any stable monocyclic, bicyclic, or polycyclic carbon ring system of from 4 to 12 atoms in each ring, wherein at least one ring is aromatic. Some examples of an aryl include phenyl, naphthyl, tetrahydro-naphthyl, indanyl, and biphenyl. Where an aryl substituent is bicyclic and one ring is non-aromatic, it is understood that attachment is to the aromatic ring. An aryl may be substituted or unsubstituted.

The term "heteroaryl" as used herein refers to any stable monocyclic, bicyclic, or polycyclic carbon ring system of from 4 to 12 atoms in each ring, wherein at least one ring is aromatic and contains from 1 to 4 heteroatoms selected from oxygen, nitrogen and sulfur. Phosphorous and selenium may be a heteroatom. Some examples of a heteroaryl include acridinyl, quinoxalinyl, pyrazolyl, indolyl, benzotriazolyl, furanyl, thienyl, benzothienyl, benzofuranyl, quinolinyl, isoquinolinyl, oxazolyl, isoxazolyl, pyrazinyl, pyridazinyl, pyridinyl, pyrimidinyl, pyrrolyl, and tetrahydroquinolinyl. A heteroaryl includes the N-oxide derivative of a nitrogen-containing heteroaryl.

The term "heterocycle" or "heterocyclyl" as used herein refers to an aromatic or nonaromatic ring system of from five to twenty-two atoms, wherein from 1 to 4 of the ring atoms are heteroatoms selected from oxygen, nitrogen, and sulfur. Phosphorous and selenium may be a heteroatom. Thus, a heterocycle may be a heteroaryl or a dihydro or tetrathydro version thereof.

The term "aroyl" as used herein refers to an aryl radical derived from an aromatic carboxylic acid, such as a substituted benzoic acid. The term "aralkyl" as used herein refers to an aryl group bonded to an alkyl group, for example, a benzyl group.

The term "carboxyl" as used herein represents a group of the formula —C(=O)OH or —C(=O)O$^-$. The terms "carbonyl" and "acyl" as used herein refer to a group in which an oxygen atom is double-bonded to a carbon atom >C=O. The term "hydroxyl" as used herein refers to —OH or —O$^-$. The term "nitrile" or "cyano" as used herein refers to —CN. The term "halogen" or "halo" refers to fluoro (—F), chloro (—Cl), bromo (—Br), and iodo (—I).

The term "substituted" as used herein refers to an atom having one or more substitutions or substituents which can be the same or different and may include a hydrogen substituent. Thus, the terms alkyl, cycloalkyl, alkenyl, alkynyl, alkoxy, alkanoyl, alkanoyloxy, alkylamino, alkylaminoalkyl, aryl, heteroaryl, heterocycle, aroyl, and aralkyl as used herein refer to groups which include substituted variations. Substituted variations include linear, branched, and cyclic variations, and groups having a substituent or substituents replacing one or more hydrogens attached to any carbon atom of the group. Substituents that may be attached to a carbon atom of the group include alkyl, cycloalkyl, alkenyl, alkynyl, alkoxy, alkanoyl, alkanoyloxy, alkylamino, alkylaminoalkyl, aryl, heteroaryl, heterocycle, aroyl, aralkyl, acyl, hydroxyl, cyano, halo, haloalkyl, amino, aminoacyl, alkylaminoacyl, acyloxy, aryloxy, aryloxyalkyl, mercapto, nitro, carbamyl, carbamoyl, and heterocycle. For example, the term ethyl includes without limitation —CH$_2$CH$_3$, —CHFCH$_3$, —CF$_2$CH$_3$, —CHFCH$_2$F, —CHFCHF$_2$, —CHFCF$_3$, —CF$_2$CH$_2$F, —CF$_2$CHF$_2$, —CF$_2$CF$_3$, and other variations as described above. In general, a substituent may itself be further substituted with any atom or group of atoms.

Some examples of a substituent for a substituted alkyl include halogen, hydroxyl, carbonyl, carboxyl, ester, aldehyde, carboxylate, formyl, ketone, thiocarbonyl, thioester, thioacetate, thioformate, selenocarbonyl, selenoester, selenoacetate, selenoformate, alkoxyl, phosphoryl, phosphonate, phosphinate, amino, amido, amidine, imino, cyano, nitro, azido, carbamato, sulfhydryl, alkylthio, sulfate, sulfonate, sulfamoyl, sulfonamido, sulfonyl, silyl, heterocyclyl, aryl, aralkyl, aromatic, and heteroaryl.

It will be understood that "substitution" or "substituted with" refers to such substitution that is in accordance with permitted valence of the substituted atom and the substituent. As used herein, the term "substituted" includes all permissible substituents.

In general, a compound may contain one or more chiral centers. Compounds containing one or more chiral centers may include those described as an "isomer," a "stereoisomer," a "diastereomer," an "enantiomer," an "optical isomer," or as a "racemic mixture." Conventions for stereochemical nomenclature, for example the stereoisomer naming rules of Cahn, Ingold and Prelog, as well as methods for the determination of stereochemistry and the separation of stereoisomers are known in the art. See, for example, Michael B. Smith and Jerry March, *March's Advanced Organic Chemistry,* 5th edition, 2001. The compounds and structures of this disclosure are meant to encompass all possible isomers, stereoisomers, diastereomers, enantiomers, and/or optical isomers that would be understood to exist for the specified compound or structure, including any mixture, racemic or otherwise, thereof.

This invention encompasses any and all tautomeric, solvated or unsolvated, hydrated or unhydrated forms, as well as any atom isotope forms of the compounds and compositions disclosed herein.

This invention encompasses any and all crystalline polymorphs or different crystalline forms of the compounds and compositions disclosed herein.

Additional Embodiments

All publications, references, patents, patent publications and patent applications cited herein are each hereby specifically incorporated by reference in their entirety for all purposes.

While this invention has been described in relation to certain embodiments, aspects, or variations, and many details have been set forth for purposes of illustration, it will be apparent to those skilled in the art that this invention includes additional embodiments, aspects, or variations, and that some of the details described herein may be varied considerably without departing from this invention. This invention includes such additional embodiments, aspects, and variations, and any modifications and equivalents thereof. In particular, this invention includes any combination of the features, terms, or elements of the various illustrative components and examples.

The use herein of the terms "a," "an," "the" and similar terms in describing the invention, and in the claims, are to be construed to include both the singular and the plural.

The terms "comprising," "having," "include," "including" and "containing" are to be construed as open-ended terms which mean, for example, "including, but not limited to." Thus, terms such as "comprising," "having," "include," "including" and "containing" are to be construed as being inclusive, not exclusive.

Recitation of a range of values herein refers individually to each and any separate value falling within the range as if it were individually recited herein, whether or not some of the values within the range are expressly recited. For example, the range "4 to 12" includes without limitation any whole, integer, fractional, or rational value greater than or equal to 4 and less than or equal to 12, as would be understood by those skilled in the art. Specific values employed herein will be understood as exemplary and not to limit the scope of the invention.

Recitation of a range of a number of atoms herein refers individually to each and any separate value falling within the range as if it were individually recited herein, whether or not some of the values within the range are expressly recited. For example, the term "C1-8" includes without limitation the species C1, C2, C3, C4, C5, C6, C7, and C8.

Definitions of technical terms provided herein should be construed to include without recitation those meanings associated with these terms known to those skilled in the art, and are not intended to limit the scope of the invention. Definitions of technical terms provided herein shall be construed to dominate over alternative definitions in the art or definitions which become incorporated herein by reference to the extent that the alternative definitions conflict with the definition provided herein.

The examples given herein, and the exemplary language used herein are solely for the purpose of illustration, and are not intended to limit the scope of the invention. All examples and lists of examples are understood to be non-limiting.

When a list of examples is given, such as a list of compounds, molecules or compositions suitable for this invention, it will be apparent to those skilled in the art that mixtures of the listed compounds, molecules or compositions may also be suitable.

EXAMPLES

Thermogravimetric analysis (TGA) was performed using a Q50 Thermogravimetric Analyzer (TA Instruments, New Castle, Del.). NMR data were recorded using a Varian 400 MHz spectrometer.

Example 1

Preparation of Polymeric Precursor Compounds and Compositions

A polymeric precursor represented by the formula $\{Cu_{0.5}Ag_{0.5}(Se^sBu)_4In\}$ was synthesized using the following procedure.

In an inert atmosphere glovebox, a Schlenk tube was charged with 0.64 g (1.22 mmol) of $In(Se^sBu)_3$, 0.15 g (0.61 mmol) of $AgSe^sBu$ and 0.12 g (0.60 mmol) of $CuSe^sBu$. Benzene (15 mL) was added, and the reaction mixture was stirred at 25° C. for 30 min. An orange solution was obtained. This solution was filtered through a filter cannula and the mother liquor was collected. The solvent was then removed under dynamic vacuum. 0.88 g (97%) of orange solid was recovered.

Elemental analysis: C, 25.3; H, 4.61. NMR: (1H) 1.03 (br), 1.72 (br), 1.80 (br), 2.05 (br), 3.72 (br), 3.95 (br) in $C_6D_6$.

The TGA for this MPP-CAIGS polymeric precursor showed a transition beginning at about 146° C., having a midpoint at about 211° C., and ending at 220° C. The yield for the transition was 49.6% (w/w), as compared to a theoretical yield for the formula $Cu_{0.5}Ag_{0.5}InSe_2$ of 48.1% (w/w). Thus, the TGA showed that this polymeric precursor can be used to prepare $Cu_{0.5}Ag_{0.5}InSe_2$ layers and materials, and can be used as a component to prepare other semiconductor layers, crystals, and materials.

Example 2

A polymeric precursor represented by the formula $\{Cu_{0.7}Ag_{0.1}(Se^sBu)_{3.8}Ga_{0.3}In_{0.7}\}$ was synthesized using the following procedure.

In an inert atmosphere glovebox, a Schlenk tube was charged with 0.74 g (1.4 mmol) of $In(Se^sBu)_3$, 0.28 g (0.59 mmol) of $Ga(Se^sBu)_3$, 0.28 g (1.4 mmol) of $CuSe^sBu$ and 48 mg (0.2 mmol) of $AgSe^sBu$. Benzene (15 mL) was added, and the reaction mixture was stirred at 25° C. for 30 min. An orange solution was obtained. This solution was filtered through a filter cannula and the mother liquor was collected. The solvent was then removed under dynamic vacuum. 1.27 g (94%) of orange oil was recovered.

Elemental analysis: C, 26.8; H, 4.04. NMR: (1H) 1.02 (br), 1.65 (br), 1.84 (br), 2.02 (br), 3.71 (br) in $C_6D_6$.

The TGA for this MPP-CAIGS polymeric precursor showed a transition beginning at about 146° C., having a midpoint at about 212° C., and ending at 235° C. The yield for the transition was 51.0% (w/w), as compared to a theoretical yield for the formula $Cu_{0.7}Ag_{0.1}Ga_{0.3}In_{0.7}Se_2$ of 47.2% (w/w). Thus, the TGA showed that this polymeric precursor can be used to prepare $Cu_{0.7}Ag_{0.1}Ga_{0.3}In_{0.7}Se_2$ layers and materials, and can be used as a component to prepare other semiconductor layers, crystals, and materials.

Example 3

A polymeric precursor represented by the formula $\{Cu_{0.8}Ag_{0.2}(Se^sBu)_4In\}$ was synthesized using the following procedure.

In an inert atmosphere glovebox, a Schlenk tube was charged with 0.52 g (1.0 mmol) of $In(Se^sBu)_3$, 0.16 g (0.8 mmol) of $CuSe^sBu$ and 49 mg (0.2 mmol) of $AgSe^sBu$. Benzene (15 mL) was added, and the reaction mixture was stirred at 25° C. for 30 min. An orange solution was obtained. This solution was filtered through a filter cannula and the mother liquor was collected. The solvent was then removed under dynamic vacuum. 0.72 g (99%) of orange oil was recovered.

Elemental analysis: C, 26.32; H, 4.87; In, 14.34; Ag, 1.54; Cu, 7.94. NMR: (1H) 0.99 (br), 1.11 (br), 1.71 (br), 1.81 (br), 2.03 (br), 3.68 (br) in $C_6D_6$.

Figure 8:
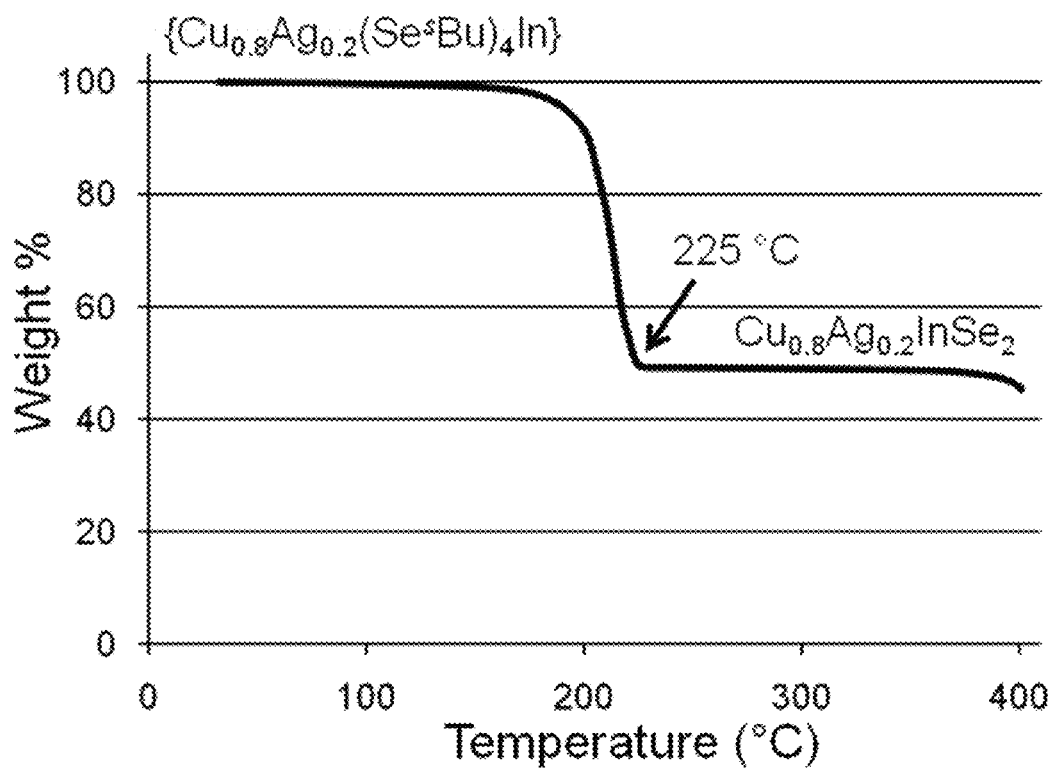
FIG. 8 shows the transition of a polymeric precursor embodiment (MPP) of this invention represented by the repeat unit formula $\{Cu_{0.8}Ag_{0.2}(Se^sBu)_4In\}$ into a $Cu_{0.8}Ag_{0.2}InSe_2$ material as determined by thermogravimetric analysis.

In FIG. 8 is shown the TGA for this MPP-CAIGS polymeric precursor. The TGA showed a transition beginning at about 139° C., having a midpoint at about 212° C., and ending at 225° C. The yield for the transition was 46.2% (w/w), as compared to a theoretical yield for the formula $Cu_{0.8}Ag_{0.2}InSe_2$ of 47.2% (w/w). Thus, the TGA showed that this polymeric precursor can be used to prepare $Cu_{0.8}Ag_{0.2}InSe_2$ layers and materials, and can be used as a component to prepare other semiconductor layers, crystals, and materials.

Example 4

A polymeric precursor represented by the formula $\{Cu_{0.2}Ag_{0.8}(Se^sBu)_4In\}$ was synthesized using the following procedure.

In an inert atmosphere glovebox, a Schlenk tube was charged with 0.52 g (1.0 mmol) of $In(Se^sBu)_3$, 40 mg (0.2 mmol) of $CuSe^sBu$ and 0.2 g (0.8 mmol) of $AgSe^sBu$. Benzene (15 mL) was added, and the reaction mixture was stirred at 25° C. for 30 min. An orange solution was obtained. This solution was filtered through a filter cannula and the mother liquor was collected. The solvent was then removed under dynamic vacuum. 0.72 g (95%) of orange oil was recovered.

Elemental analysis: C, 24.87; H, 4.64; Ag, 9.38; Cu, 1.71; In, 14.83. NMR: (1H) 1.06 (br), 1.80 (br), 2.08 (br), 3.72 (br) 3.95 (br) in $C_6D_6$.

Figure 9:
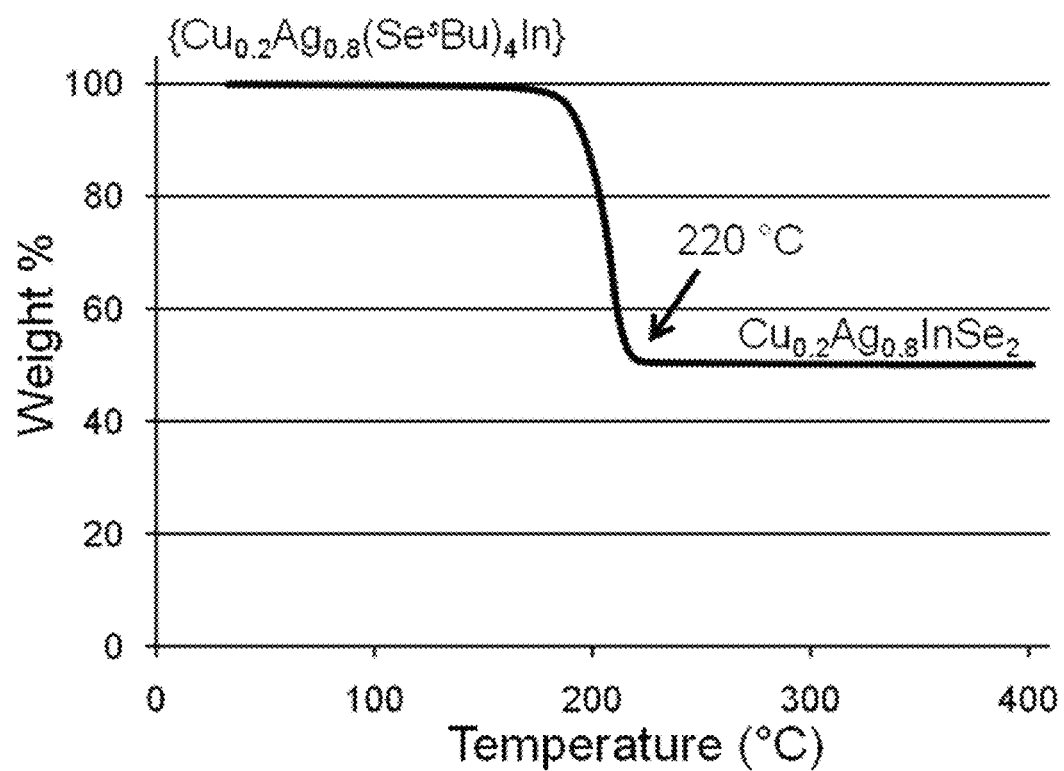
FIG. 9 shows the transition of a polymeric precursor embodiment (MPP) of this invention represented by the repeat unit formula $\{Cu_{0.2}Ag_{0.8}(Se^sBu)_4In\}$ into a $Cu_{0.2}Ag_{0.8}InSe_2$ material as determined by thermogravimetric analysis.

In FIG. 9 is shown the TGA for this MPP-CAIGS polymeric precursor. The TGA showed a transition beginning at about 142° C., having a midpoint at about 207° C., and ending at 220° C. The yield for the transition was 50.2% (w/w), as compared to a theoretical yield for the formula $Cu_{0.2}Ag_{0.8}InSe_2$ of 49.0% (w/w). Thus, the TGA showed that this polymeric precursor can be used to prepare $Cu_{0.2}Ag_{0.8}InSe_2$ layers and materials, and can be used as a component to prepare other semiconductor layers, crystals, and materials.

Example 5

A polymeric precursor represented by the formula $\{Cu_{0.5}Ag_{0.5}(Se^sBu)_4Ga_{0.5}In_{0.5}\}$ was synthesized using the following procedure.

In an inert atmosphere glovebox, a Schlenk tube was charged with 0.26 g (0.5 mmol) of $In(Se^sBu)_3$, 0.24 g (0.5 mmol) of $Ga(Se^sBu)_3$, 0.10 g (0.5 mmol) of $CuSe^sBu$ and 0.12 g (0.5 mmol) of $AgSe^sBu$. Benzene (15 mL) was added, and the reaction mixture was stirred at 25° C. for 30 min. An orange solution was obtained. This solution was filtered through a filter cannula and the mother liquor was collected. The solvent was then removed under dynamic vacuum. 0.72 g (95%) of orange oil was recovered.

Elemental analysis: C, 26.09; H, 4.73; In, 13.79; Ga, 5.24; Ag, 7.53; Cu, 4.65. NMR: (1H) 1.04 (br), 1.72 (br), 1.82 (br), 2.06 (br), 3.75 (br), 3.93 (br) in $C_6D_6$.

The TGA for this MPP-CAIGS polymeric precursor showed a transition beginning at about 152° C., having a midpoint at about 216° C., and ending at 225° C. The yield for the transition was 47.8% (w/w), as compared to a theoretical yield for the formula $Cu_{0.5}Ag_{0.5}Ga_{0.5}In_{0.5}Se_2$ of 46.5% (w/w). Thus, the TGA showed that this polymeric precursor can be used to prepare $Cu_{0.5}Ag_{0.5}Ga_{0.5}In_{0.5}Se_2$ layers and materials, and can be used as a component to prepare other semiconductor layers, crystals, and materials.

Example 6

A polymeric precursor represented by the formula $\{Cu_{0.85}Ag_{0.1}(Se^sBu)_{3.95}Ga_{0.3}In_{0.7}\}$ was synthesized using the following procedure.

In an inert atmosphere glovebox, a Schlenk tube was charged with 0.74 g (1.4 mmol) of $In(Se^sBu)_3$, 0.28 g (0.6 mmol) of $Ga(Se^sBu)_3$, 0.34 g (1.7 mmol) of $CuSe^sBu$ and 48 mg (0.2 mmol) of $AgSe^sBu$. Benzene (15 mL) was added, and the reaction mixture was stirred at 25° C. for 30 min. An orange solution was obtained. This solution was filtered through a filter cannula and the mother liquor was collected. The solvent was then removed under dynamic vacuum. 1.39 g (99%) of orange oil was recovered.

Elemental analysis: C, 26.64; H, 4.68; Ag, 1.49; Cu, 7.88; In, 13.65; Ga, 3.02. NMR: (1H) 1.00 (br), 1.72 (br), 1.82 (br), 2.03 (br), 3.70 (br) in $C_6D_6$.

Figure 10:
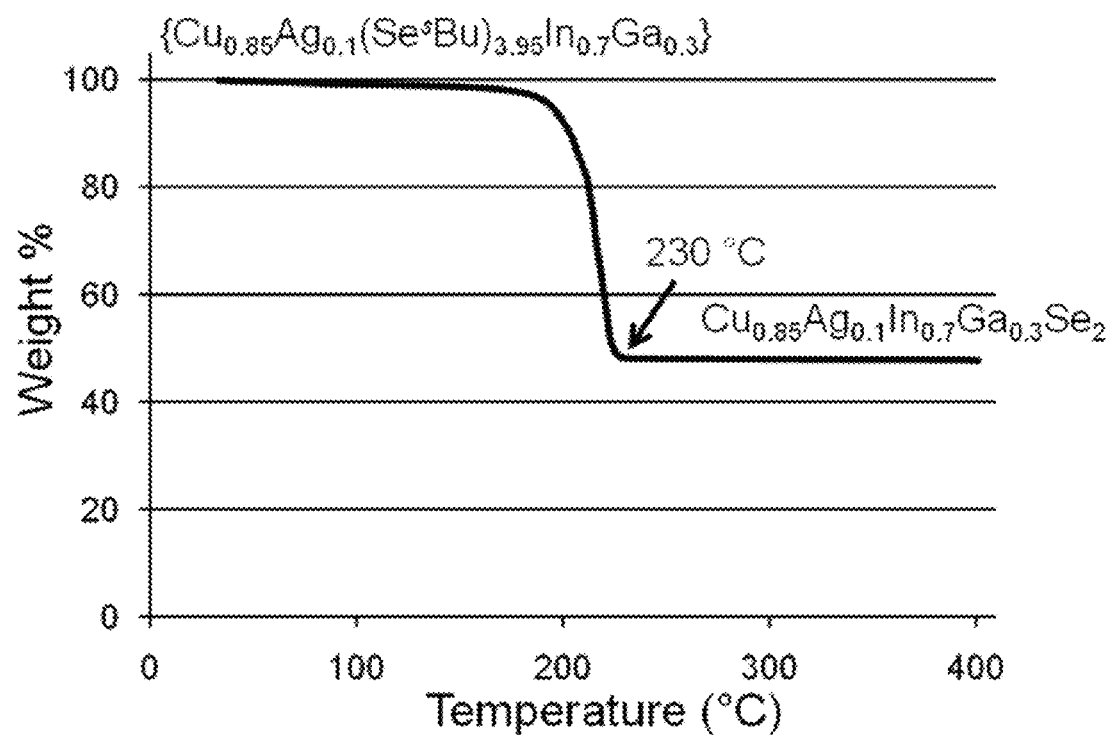
FIG. 10 shows the transition of a polymeric precursor embodiment (MPP) of this invention represented by the repeat unit formula $\{Cu_{0.85}Ag_{0.1}(Se^sBu)_{3.95}In_{0.7}Ga_{0.3}\}$ into a $Cu_{0.85}Ag_{0.1}In_{0.7}Ga_{0.3}Se_2$ material as determined by thermogravimetric analysis.

In FIG. 10 is shown the TGA for this MPP-CAIGS polymeric precursor. The TGA showed a transition beginning at about 151° C., having a midpoint at about 216° C., and ending at 230° C. The yield for the transition was 46.8% (w/w), as compared to a theoretical yield for the formula $Cu_{0.85}Ag_{0.1}Ga_{0.3}In_{0.7}Se_2$ of 46.1% (w/w). Thus, the TGA showed that this polymeric precursor can be used to prepare $Cu_{0.85}Ag_{0.1}Ga_{0.3}In_{0.7}Se_2$ layers and materials, and can be used as a component to prepare other semiconductor layers, crystals, and materials.

Example 7

A polymeric precursor represented by the formula $\{Cu_{0.5}Ag_{0.5}(Se^sBu)_4Ga_{0.3}In_{0.7}\}$ was synthesized using the following procedure.

In an inert atmosphere glovebox, a Schlenk tube was charged with 0.74 g (1.4 mmol) of $In(Se^sBu)_3$, 0.28 g (0.6 mmol) of $Ga(Se^sBu)_3$, 0.20 g (1.0 mmol) of $CuSe^sBu$ and 0.24 g (1.0 mmol) of $AgSe^sBu$. Benzene (15 mL) was added, and the reaction mixture was stirred at 25° C. for 30 min. An orange solution was obtained. This solution was filtered through a filter cannula and the mother liquor was collected. The solvent was then removed under dynamic vacuum. 1.38 g (95%) of orange oil was recovered.

Elemental analysis: C, 25.93; H, 4.82; Ag, 8.56; Cu, 3.79; In, 13.87; Ga, 2.89. NMR: (1H) 1.04 (br), 1.74 (br), 1.85 (br), 2.06 (br), 3.74 (br), 3.94 (br) in $C_6D_6$.

Figure 11:
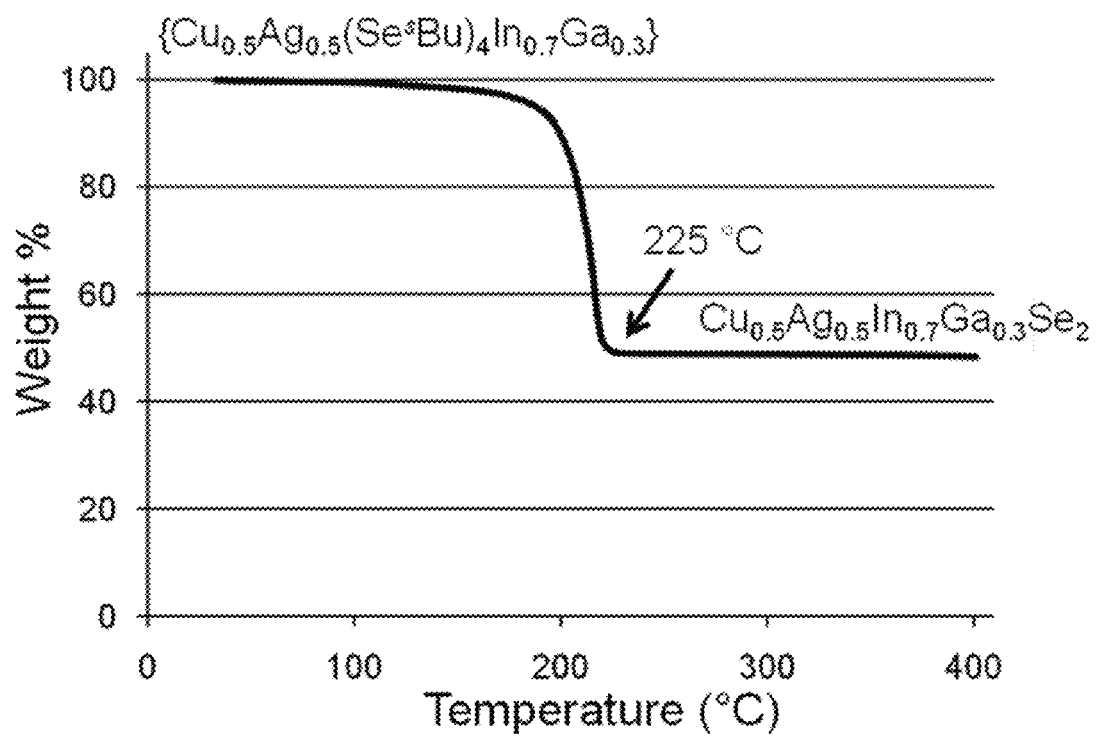
FIG. 11 shows the transition of a polymeric precursor embodiment (MPP) of this invention represented by the repeat unit formula $\{Cu_{0.5}Ag_{0.5}(Se^sBu)_4In_{0.7}Ga_{0.3}\}$ into a $Cu_{0.5}Ag_{0.5}In_{0.1}Ga_{0.3}Se_2$ material as determined by thermogravimetric analysis.

In FIG. 11 is shown the TGA for this MPP-CAIGS polymeric precursor. The
TGA showed a transition beginning at about 148° C., having a midpoint at about 213° C., and ending at 225° C. The yield for the transition was 48.5% (w/w), as compared to a theoretical yield for the formula $Cu_{0.5}Ag_{0.5}Ga_{0.3}In_{0.7}Se_2$ of 47.2% (w/w). Thus, the TGA showed that this polymeric precursor can be used to prepare $Cu_{0.5}Ag_{0.5}Ga_{0.3}In_{0.7}Se_2$ layers and materials, and can be used as a component to prepare other semiconductor layers, crystals, and materials.

Example 8

A polymeric precursor represented by the formula $\{Cu_{0.8}Ag_{0.05}(Se^sBu)_{3.85}Ga_{0.3}In_{0.7}\}$ was synthesized using the following procedure.

In an inert atmosphere glovebox, a Schlenk tube was charged with 0.73 g (1.4 mmol) of $In(Se^sBu)_3$, 0.29 g (0.6 mmol) of $Ga(Se^sBu)_3$, 0.32 g (1.6 mmol) of $CuSe^sBu$ and 24 mg (0.1 mmol) of $AgSe^sBu$. Benzene (15 mL) was added, and the reaction mixture was stirred at 25° C. for 30 min. An orange solution was obtained. This solution was filtered through a filter cannula and the mother liquor was collected. The solvent was then removed under dynamic vacuum. 1.29 g (95%) of orange oil was recovered.

NMR: (1H) 1.0 (br), 1.71 (br), 1.82 (br), 2.03 (br), 3.69 (br) in $C_6D_6$.

The TGA for this MPP-CAIGS polymeric precursor showed a transition beginning at about 140° C., having a midpoint at about 215° C., and ending at 230° C. The yield for the transition was 46.0% (w/w), as compared to a theoretical yield for the formula $Cu_{0.8}Ag_{0.05}Ga_{0.3}In_{0.7}Se_2$ of 46.3% (w/w). Thus, the TGA showed that this polymeric precursor can be used to prepare $Cu_{0.8}Ag_{0.05}Ga_{0.3}In_{0.7}Se_2$ layers and materials, and can be used as a component to prepare other semiconductor layers, crystals, and materials.

Example 9

Preparation of Polymeric Precursor Compounds and Compositions

A polymeric precursor represented by the formula $\{Ag(Se^{sec}Bu)_4In\}$ was synthesized using the following procedure.

In an inert atmosphere glovebox, a Schlenk tube was charged with 0.52 g (1 mmol) of $In(Se^sBu)_3$ and 0.24 g (1 mmol) of $AgSe^sBu$. Benzene (15 mL) was added, and the reaction mixture was stirred at 25° C. for 30 min. A light yellow solution was obtained. This solution was filtered through a filter cannula and the mother liquor was collected. The solvent was then removed under dynamic vacuum. 0.52 g (68%) of light yellow solid was recovered.

Elemental analysis: C, 24.59; H, 4.45; In, 15.21; Ag, 15.71. NMR: (1H) 1.07 (t, 12 H, $^3J_{HH}$=7.2 Hz), 1.81 (d, 12 H, $^3J_{HH}$=6.8 Hz), 1.86-2.16 (m, 8 H), 3.72-3.80 (m, 4H) in $C_6D_6$.

The TGA for this MPP-AIGS polymeric precursor showed a transition beginning at about 147° C., having a midpoint at about 207° C., and ending at about 220° C. The yield for the transition was 49.8% (w/w), as compared to a theoretical yield for the formula $AgInSe_2$ of 49.6% (w/w). Thus, the TGA showed that this polymeric precursor can be used to prepare $AgInSe_2$ layers and materials, and can be used as a component to prepare other semiconductor layers, crystals, and materials.

Example 10

A polymeric precursor represented by the formula $\{Ag_{0.6}(Se^{sec}Bu)_{3.6}In\}$ was synthesized using the following procedure.

In an inert atmosphere glovebox, a Schlenk tube was charged with 0.52 g (1 mmol) of $In(Se^sBu)_3$ and 0.15 g (0.60 mmol) of $AgSe^sBu$. Benzene (15 mL) was added, and the reaction mixture was stirred at 25° C. for 30 min. A light yellow solution was obtained. This solution was filtered through a filter cannula and the mother liquor was collected. The solvent was then removed under dynamic vacuum. 0.31 g (46%) of light yellow oil was recovered.

Elemental analysis: C, 26.2; H, 4.73. NMR: (1H) 1.03 (t, $^3J_{HH}$=7.2 Hz), 1.10 (br), 1.71 (br), 1.83 (br), 1.95 (br), 2.07 (br), 2.09 (br), 3.75 (br), 3.95 (br) in $C_6D_6$.

The TGA for this MPP-AIGS polymeric precursor showed a transition beginning at about 143° C., having a midpoint at about 203° C., and ending at about 230° C. The yield for the transition was 50.3% (w/w), as compared to a theoretical yield for the formula $Ag_{0.6}InSe_2$ of 50.4% (w/w). Thus, the TGA showed that this polymeric precursor can be used to prepare $Ag_{0.6}InSe_2$ layers and materials, and can be used as a component to prepare other semiconductor layers, crystals, and materials.

Example 11

A polymeric precursor represented by the formula $\{Ag_{0.9}(Se^sBu)_{3.9}In\}$ was synthesized using the following procedure.

In an inert atmosphere glovebox, a Schlenk tube was charged with 0.36 g (0.69 mmol) of $In(Se^sBu)_3$ and 0.15 g (0.61 mmol) of $AgSe^sBu$. Benzene (15 mL) was added, and the reaction mixture was stirred at 25° C. for 30 min. A light yellow solution was obtained. This solution was filtered through a filter cannula and the mother liquor was collected. The solvent was then removed under dynamic vacuum. 0.49 g (96%) of light yellow solid was recovered.

Elemental analysis: C, 24.3; H, 4.45. NMR: (1H) 1.06 (t, 12 H, $^3J_{HH}$=6.8 Hz), 1.67 (br), 1.74 (br), 1.80 (br), 1.85 (d, $^3J_{HH}$=6.8 Hz), 2.09 (br), 3.75 (q, $^3J_{HH}$=6.4 Hz), 3.95 (br) in $C_6D_6$.

Figure 12:
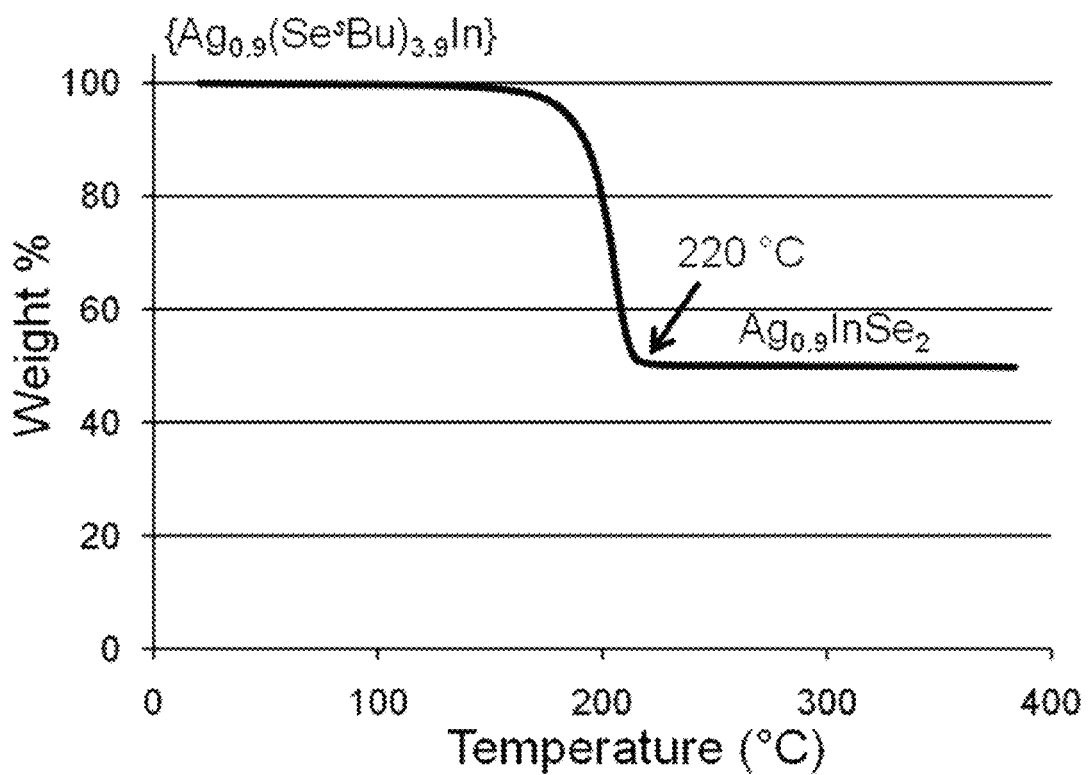
FIG. 12 shows the transition of a polymeric precursor embodiment (MPP) of this invention represented by the repeat unit formula $\{Ag_{0.9}(Se^{sec}Bu)_{3.9}In\}$ into a $Ag_{0.9}InSe_2$ material as determined by thermogravimetric analysis.

In FIG. 12 is shown the TGA for this MPP-AIGS polymeric precursor. The TGA showed a transition beginning at about 151° C., having a midpoint at 203° C., and ending at 220° C. The yield for the transition was 50.3% (w/w), as compared to a theoretical yield for the formula $Ag_{0.9}InSe_2$ of 49.8% (w/w). Thus, the TGA showed that this polymeric precursor can be used to prepare $Ag_{0.9}InSe_2$ layers and materials, and can be used as a component to prepare other semiconductor layers, crystals, and materials.

Example 12

A polymeric precursor represented by the formula $\{Ag_{1.5}(Se^sBu)_{4.5}In\}$ was synthesized using the following procedure.

In an inert atmosphere glovebox, a Schlenk tube was charged with 0.31 g (0.59 mmol) of $In(Se^sBu)_3$ and 0.22 g (0.90 mmol) of $AgSe^sBu$. Benzene (15 mL) was added, and the reaction mixture was stirred at 25° C. for 30 min. A dark brown solution was obtained. This solution was filtered through a filter cannula and the mother liquor was collected. The solvent was then removed under dynamic vacuum. 0.49 g (92%) of dark brown oil was recovered.

Elemental analysis: C, 24.1; H, 4.35; Ag, 17.1; In, 12.6. NMR: (1H) 1.06 (t, 12H, $^3J_{HH}$=6.8 Hz), 1.80 (d, 12 H, $^3J_{HH}$=6.4 Hz), 1.85-2.11 (m, 8 H), 3.72-3.77 (m, 4 H) in $C_6D_6$.

Figure 13:
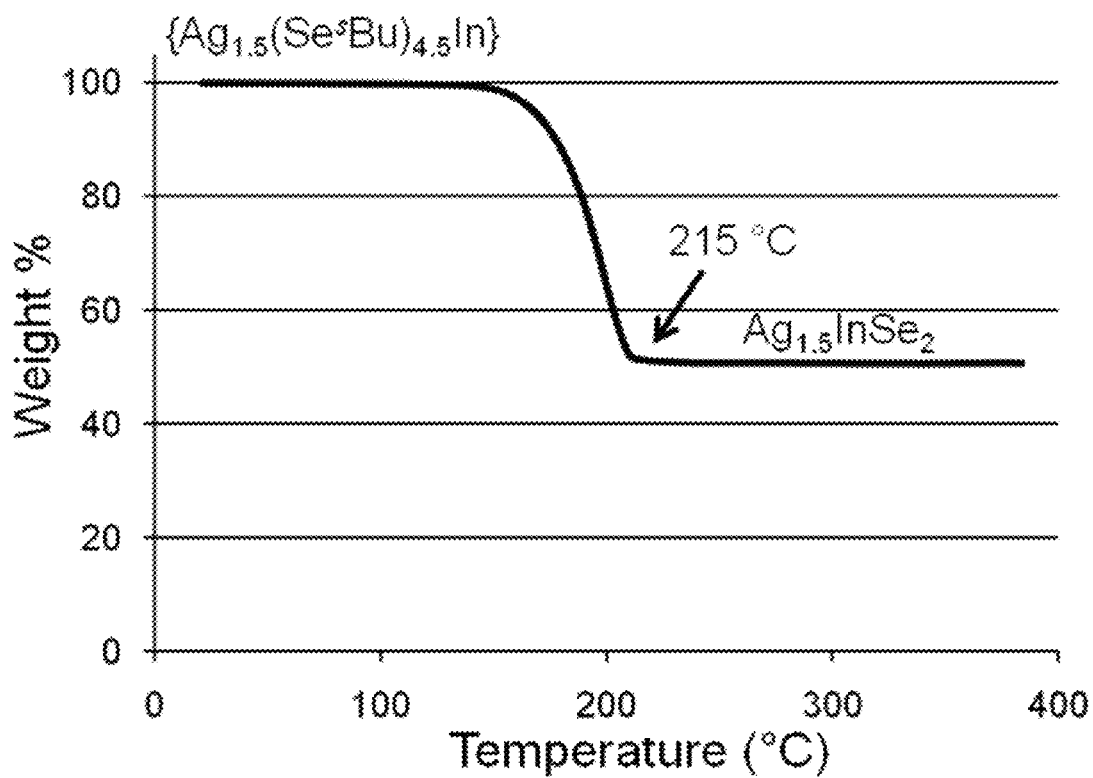
FIG. 13 shows the transition of a polymeric precursor embodiment (MPP) of this invention represented by the repeat unit formula $\{Ag_{1.5}(Se^{sec}Bu)_{4.5}In\}$ into a $Ag_{1.5}InSe_2$ material as determined by thermogravimetric analysis.

In FIG. 13 is shown the TGA for this MPP-AIGS polymeric precursor. The TGA showed a transition beginning at about 135° C., having a midpoint at about 194° C., and ending at 215° C. The yield for the transition was 51.0% (w/w), as compared to a theoretical yield for the formula $Ag_{1.5}InSe_2$ of 48.9% (w/w). Thus, the TGA showed that this polymeric precursor can be used to prepare $Ag_{1.5}InSe_2$ layers and materials, and can be used as a component to prepare other semiconductor layers, crystals, and materials.

Example 13

A polymeric precursor represented by the formula {Ag(Se$^s$Bu)$_3$(Se$^t$Bu)In} was synthesized using the following procedure.

In an inert atmosphere glovebox, a Schlenk tube was charged with 0.26 g (0.50 mmol) of In(Se$^s$Bu)$_3$ and 0.12 g (0.50 mmol) of AgSe$^s$Bu. Benzene (15 mL) was added, and the reaction mixture was stirred at 25° C. for 30 min. A dark brown solution was obtained. This solution was filtered through a filter cannula and the mother liquor was collected. The solvent was then removed under dynamic vacuum. 0.31 g (97%) of brown solid was recovered.

NMR: (1H) 1.07 (br), 1.83 (br), 1.88 (br), 2.12 (br), 3.79 (br) in $C_6D_6$.

The TGA for this MPP-AIGS polymeric precursor showed transition onsets at about 117 and 174° C., and ending at about 230° C. The yield for the transitions was 50.8% (w/w), as compared to a theoretical yield for the formula $AgInSe_2$ of 49.6% (w/w). Thus, the TGA showed that this polymeric precursor can be used to prepare $AgInSe_2$ layers and materials, and can be used as a component to prepare other semiconductor layers, crystals, and materials.

Example 14

A polymeric precursor represented by the formula {Ag(Se$^s$Bu)$_4$Ga} was synthesized using the following procedure.

In an inert atmosphere glovebox, a Schlenk tube was charged with 0.96 g (2 mmol) of Ga(Se$^s$Bu)$_3$ and 0.49 g (2 mmol) of AgSe$^s$Bu. Benzene (15 mL) was added, and the reaction mixture was stirred at 25° C. for 30 min. A light yellow solution was obtained. This solution was filtered through a filter cannula and the mother liquor was collected. The solvent was then removed under dynamic vacuum. 0.73 g (51%) of light yellow solid was recovered.

Elemental analysis: C, 25.8; H, 4.7; Ag, 15.4; Ga, 9.74. NMR: (1H) 1.07 (t, 12 H, $^3J_{HH}$=7.6 Hz), 1.79 (d, 12 H, $^3J_{HH}$=6.8 Hz), 1.84-2.16 (m, 8 H), 3.75-3.80 (m, 4H) in $C_6D_6$.

Figure 14:
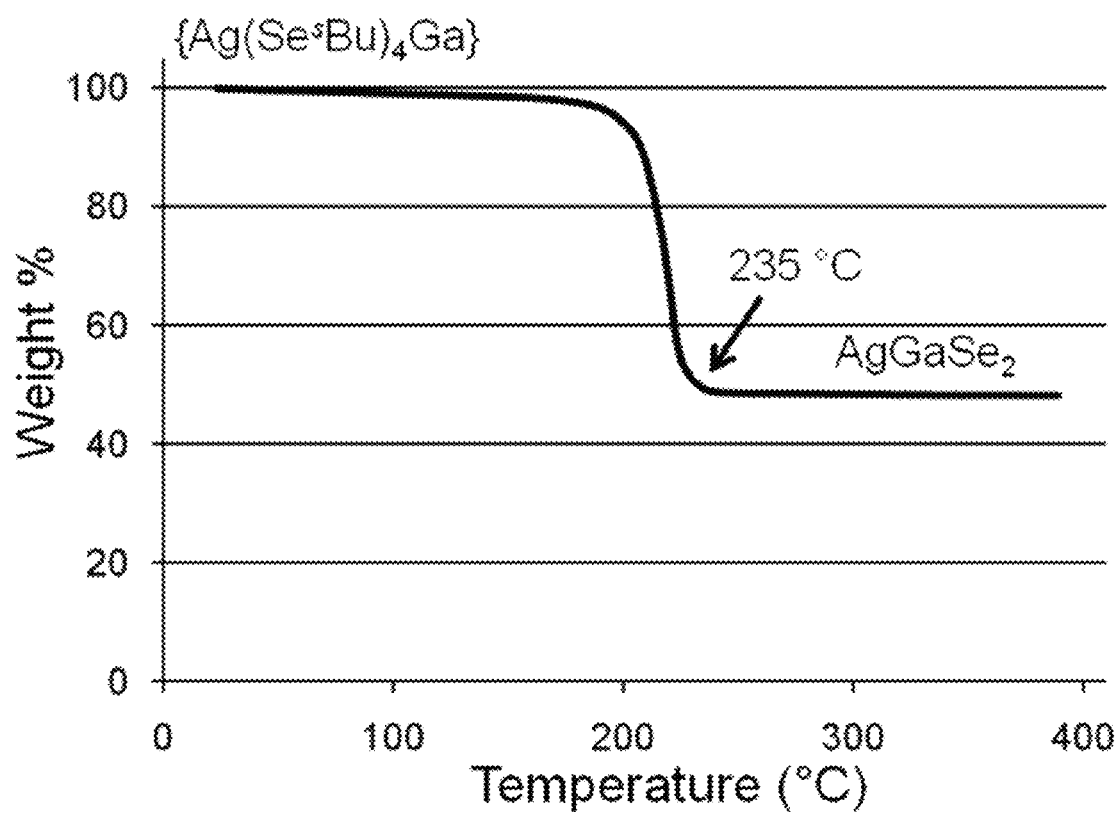
FIG. 14 shows the transition of a polymeric precursor embodiment (MPP) of this invention represented by the repeat unit formula $\{Ag(Se^{sec}Bu)_4Ga\}$ into a $AgGaSe_2$ material as determined by thermogravimetric analysis.

In FIG. 14 is shown the TGA for this MPP-AIGS polymeric precursor. The TGA showed a transition beginning at about 139° C., having a midpoint at about 219° C., and ending at 235° C. The yield for the transition was 49.9% (w/w), as compared to a theoretical yield for the formula $AgGaSe_2$ of 46.5% (w/w). Thus, the TGA showed that this polymeric precursor can be used to prepare $AgGaSe_2$ layers and materials, and can be used as a component to prepare other semiconductor layers, crystals, and materials.

Example 15

A polymeric precursor represented by the formula {$Ag_{0.8}$(Se$^s$Bu)$_{3.8}$In$_{0.2}$Ga$_{0.8}$} was synthesized using the following procedure.

In an inert atmosphere glovebox, a Schlenk tube was charged with 0.10 g (0.2 mmol) of In(Se$^s$Bu)$_3$, 0.38 g (0.8 mmol) of Ga(Se$^s$Bu)$_3$ and 0.20 g (0.8 mmol) of AgSe$^s$Bu. Benzene (15 mL) was added, and the reaction mixture was stirred at 25° C. for 30 min. A light yellow solution was obtained. This solution was filtered through a filter cannula and the mother liquor was collected. The solvent was then removed under dynamic vacuum. 0.61 g (90%) of light yellow solid was recovered.

Elemental analysis: C, 25.9; H, 4.7. NMR: (1H) 1.04 (br), 1.10 (br), 1.74 (br), 1.86 (br), 2.06 (br), 3.76 (br), 3.93 (br) in $C_6D_6$.

Figure 15:
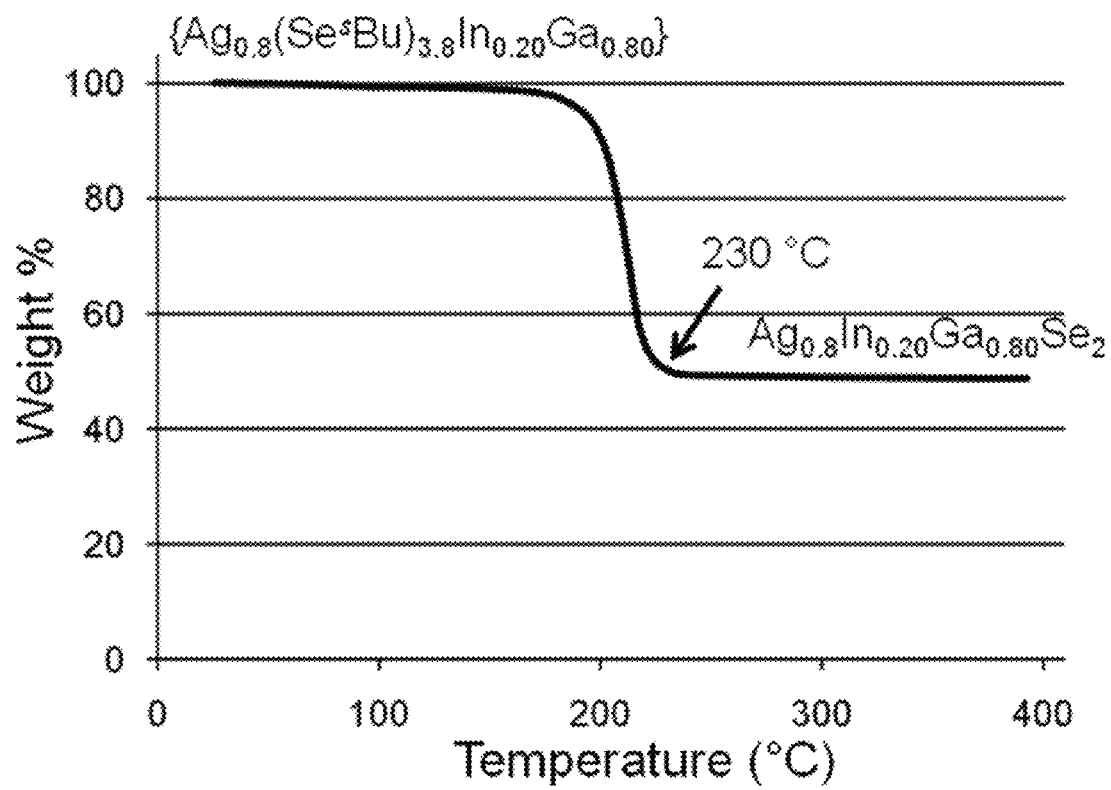
FIG. 15 shows the transition of a polymeric precursor embodiment (MPP) of this invention represented by the repeat unit formula $\{Ag_{0.8}(Se^sBu)_{3.8}In_{0.20}Ga_{0.80}\}$ into a $Ag_{0.8}In_{0.20}Ga_{0.80}Se_2$ material as determined by thermogravimetric analysis.

In FIG. 15 is shown the TGA for this MPP-AIGS polymeric precursor. The TGA showed a transition beginning at about 159° C., having a midpoint at about 211° C., and ending at 230° C. The yield for the transition was 49.7% (w/w), as compared to a theoretical yield for the formula $Ag_{0.8}In_{0.2}Ga_{0.8}Se_2$ of 47.3% (w/w). Thus, the TGA showed that this polymeric precursor can be used to prepare $Ag_{0.8}In_{0.2}Ga_{0.8}Se_2$ layers and materials, and can be used as a component to prepare other semiconductor layers, crystals, and materials.

Example 16

A polymeric precursor represented by the formula {Ag(Se$^s$Bu)$_4$In$_{0.3}$Ga$_{0.7}$} was synthesized using the following procedure.

In an inert atmosphere glovebox, a Schlenk tube was charged with 0.16 g (0.3 mmol) of In(Se$^s$Bu)$_3$, 0.33 g (0.7 mmol) of Ga(Se$^s$Bu)$_3$ and 0.24 g (1 mmol) of AgSe$^s$Bu. Benzene (15 mL) was added, and the reaction mixture was stirred at 25° C. for 30 min. A light yellow solution was obtained. This solution was filtered through a filter cannula and the mother liquor was collected. The solvent was then removed under dynamic vacuum. 0.69 g (95%) of light yellow solid was recovered.

Elemental analysis: C, 25.4; H, 4.56. NMR: (1H) 1.05 (br), 1.69 (br), 1.77 (br), 1.85 (br), 2.08 (br), 3.76 (br), 3.93 (br) in $C_6D_6$.

Figure 16:
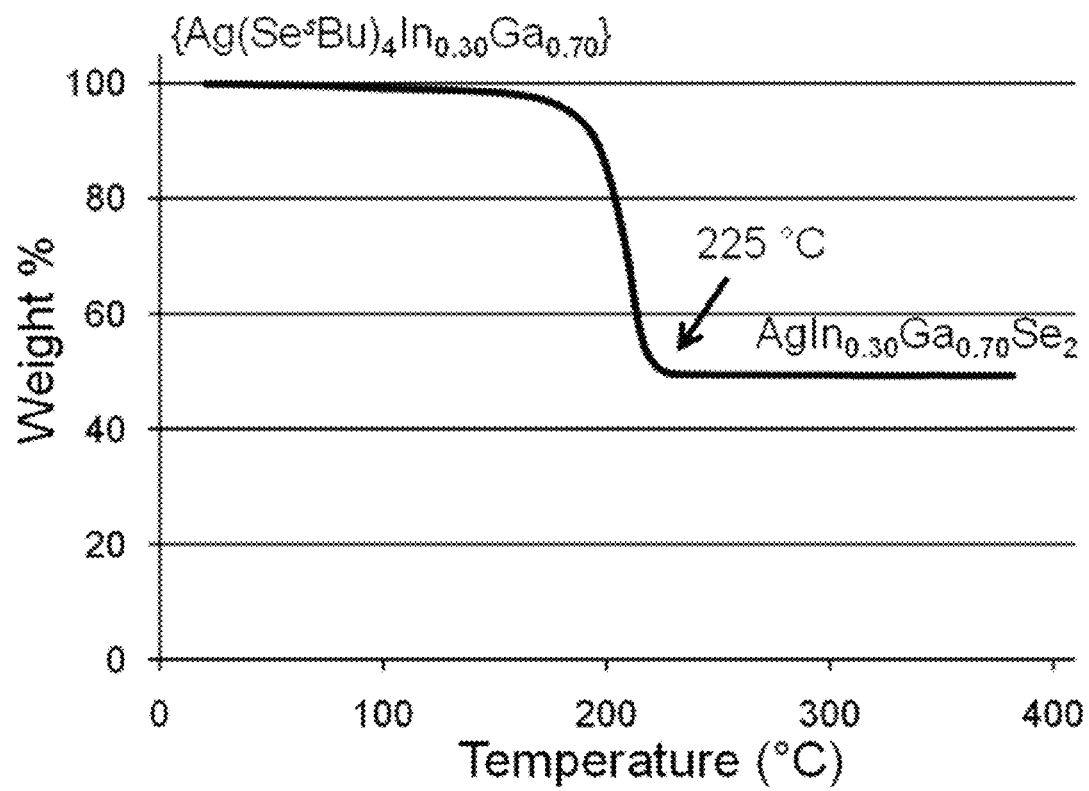
FIG. 16 shows the transition of a polymeric precursor embodiment (MPP) of this invention represented by the repeat unit formula $\{Ag(Se^sBu)_4In_{0.30}Ga_{0.70}\}$ into a $AgIn_{0.30}Ga_{0.70}Se_2$ material as determined by thermogravimetric analysis.

In FIG. 16 is shown the TGA for this MPP-AIGS polymeric precursor. The TGA showed a transition beginning at about 149° C., having a midpoint at about 209° C., and ending at 225° C. The yield for the transition was 50.6% (w/w), as compared to a theoretical yield for the formula $AgIn_{0.3}Ga_{0.7}Se_2$ of 47.5% (w/w). Thus, the TGA showed that this polymeric precursor can be used to prepare $AgIn_{0.3}Ga_{0.7}Se_2$ layers and materials, and can be used as a component to prepare other semiconductor layers, crystals, and materials.

Example 17

A polymeric precursor represented by the formula {Ag(Se$^s$Bu)$_4$In$_{0.7}$Ga$_{0.3}$} was synthesized using the following procedure.

In an inert atmosphere glovebox, a Schlenk tube was charged with 0.37 g (0.7 mmol) of In(Se$^s$Bu)$_3$, 0.14 g (0.3 mmol) of Ga(Se$^s$Bu)$_3$ and 0.24 g (1 mmol) of AgSe$^s$Bu. Benzene (15 mL) was added, and the reaction mixture was stirred at 25° C. for 30 min. A light yellow solution was obtained. This solution was filtered through a filter cannula and the mother liquor was collected. The solvent was then removed under dynamic vacuum. 0.72 g (96%) of light yellow solid was recovered.

Elemental analysis: C, 24.9; H, 4.53; Ag, 15.6; In, 10.88; Ga, 2.72. NMR: (1H) 1.06 (br), 1.68 (br), 1.79 (br), 1.86 (br), 2.09 (br), 3.76 (br), 3.93 (br) in $C_6D_6$.

The TGA for this MPP-AIGS polymeric precursor showed a transition beginning at about 140° C., having a midpoint at about 203° C., and ending at 220° C. The yield for the transition was 50.5% (w/w), as compared to a theoretical yield for the formula $AgIn_{0.7}Ga_{0.3}Se_2$ of 48.7% (w/w). Thus, the TGA showed that this polymeric precursor can be used to prepare $AgIn_{0.7}Ga_{0.3}Se_2$ layers and materials, and can be used as a component to prepare other semiconductor layers, crystals, and materials.

Example 18

A polymeric precursor represented by the formula {Ag$(Se^sBu)_4In_{0.5}Ga_{0.5}$} was synthesized using the following procedure.

In an inert atmosphere glovebox, a Schlenk tube was charged with 0.26 g (0.5 mmol) of $In(Se^sBu)_3$, 0.24 g (0.5 mmol) of $Ga(Se^sBu)_3$ and 0.24 g (1 mmol) of $AgSe^sBu$. Benzene (15 mL) was added, and the reaction mixture was stirred at 25° C. for 30 min. A light yellow solution was obtained. This solution was filtered through a filter cannula and the mother liquor was collected. The solvent was then removed under dynamic vacuum. 0.58 g (78%) of light yellow solid was recovered.

Elemental analysis: C, 25.1; H, 4.57; Ag, 14.94; In, 7.77; Ga, 5.06. NMR: (1H) 1.04 (br), 1.77 (br), 1.85 (br), 2.08 (br), 3.76 (br), 3.93 (br) in $C_6D_6$.

The TGA for this MPP-AIGS polymeric precursor showed a transition beginning at about 149° C., having a midpoint at about 207° C., and ending at 225° C. The yield for the transition was 50.5% (w/w), as compared to a theoretical yield for the formula $AgIn_{0.5}Ga_{0.5}Se_2$ of 48.1% (w/w). Thus, the TGA showed that this polymeric precursor can be used to prepare $AgIn_{0.5}Ga_{0.5}Se_2$ layers and materials, and can be used as a component to prepare other semiconductor layers, crystals, and materials.

Example 19

A polymeric precursor represented by the formula {Ag$(Se^sBu)_3(Se^tBu)Ga_{0.3}In_{0.7}$} was synthesized using the following procedure.

In an inert atmosphere glovebox, a Schlenk tube was charged with 0.37 g (0.7 mmol) of $In(Se^sBu)_3$, 0.14 g (0.3 mmol) of $Ga(Se^sBu)_3$ and 0.24 g (1.0 mmol) of $AgSe^tBu$. Benzene (15 mL) was added, and the reaction mixture was stirred at 25° C. for 30 min. A light yellow solution was obtained. This solution was filtered through a filter cannula and the mother liquor was collected. The solvent was then removed under dynamic vacuum. 0.71 g (95%) of light yellow powder was recovered.

NMR: (1H) 1.06 (br), 1.83 (br), 2.12 (br), 3.79 (br) in $C_6D_6$.

The TGA for this MPP-Ag polymeric precursor showed transition onsets at about 94 and 177° C., ending at about 220° C. The yield for the transitions was 50.5% (w/w), as compared to a theoretical yield for the formula $AgGa_{0.3}In_{0.7}Se_2$ of 47.5% (w/w). Thus, the TGA showed that this polymeric precursor can be used to prepare $AgGa_{0.3}In_{0.7}Se_2$ layers and materials, and can be used as a component to prepare other semiconductor layers, crystals, and materials.

Example 20

A polymeric precursor represented by the formula {Ag$(Se^nHex)_4In$} was synthesized using the following procedure.

In an inert atmosphere glovebox, a Schlenk tube was charged with 1.93 g (3.2 mmol) of $In(Se^nHex)_3$ and 0.86 g (3.2 mmol) of $AgSe^nHex$. Benzene (50 mL) was added, and the reaction mixture was stirred at 25° C. for 30 min. A yellow solution was obtained. The solvent was removed, and the oil product was extracted with pentane. Upon removal of pentane, 2.62 g (94%) of bright yellow oil was obtained.

NMR: (1H) 0.92 (br), 1.35 (br), 1.52 (br), 2.04 (br), 3.22 (br) in $C_6D_6$.

The TGA for this MPP-AIGS polymeric precursor showed a transition onset at about 127° C., ending at about 236° C. The yield for the transition was 44.5% (w/w), as compared to a theoretical yield for the formula $AgInSe_2$ of 43.3% (w/w). Thus, the TGA showed that this polymeric precursor can be used to prepare $AgInSe_2$ layers and materials, and can be used as a component to prepare other semiconductor layers, crystals, and materials.

Example 21

Preparation of Monomer Compounds

A monomer compound represented by the formula $Ga(Se^nBu)_3$ was synthesized using the following procedure.

To a 500-mL round bottom Schlenk flask in an inert atmosphere glove box was added $NaSe^nBu$ (28 g, 176 mmol) and THF (200 mL). The flask was then transferred to a Schlenk line and a solution of $GaCl_3$ (10.3 g, 59 mmol) in 20 mL of benzene was then added. The reaction mixture was stirred for 12 h and the volatiles were removed under reduced pressure. The residue was extracted with toluene and filtered. The volatiles from the filtrate were then removed under reduced pressure leaving a colorless oil (23 g, 48 mmol, 83% yield).

NMR: (1H; C6D6): 0.85 (t, $J_{HH}$=7.2 Hz, 9 H, $CH_3$); 1.40 (m, 6 H, —$CH_2$—); 1.77 (m, 6 H, —$CH_2$—); 3.03 (br s, 6 H, $SeCH_2$—).

Example 22

A monomer compound represented by the formula $In(Se^nBu)_3$ was synthesized using the following procedure.

To a 500-mL round bottom Schlenk flask in an inert atmosphere glove box was added $InCl_3$ (6.95 g, 31 mmol), $NaSe^nBu$ (15 g, 94 mmol), and THF (200 mL). The reaction mixture was transferred to a Schlenk line and stirred for 12 h. The volatiles were subsequently removed under reduced pressure. The remaining solid residue was dissolved in hot toluene and filtered. The volatiles from the filtrate were removed under reduced pressure and the resulting solid was washed with pentane. The final colorless solid was dried under reduced pressure and isolated (15 g, 29 mmol, 92% yield).

NMR: (1H; C6D6): 0.913 (t, $J_{HH}$=7.2 Hz, 9 H, $CH_3$); 1.43 (m, 6 H, —$CH_2$—); 1.72 (m, 6H, —$CH_2$—); 2.90 (t, $J_{HH}$=7.2 Hz, 6 H, $SeCH_2$—).

Example 23

A monomer compound represented by the formula $Ag(Se^tBu)$ was synthesized using the following procedure.

$^tBuSeH$ (5.8 mmol) and $Et_3N$ (1.1 mL) were slowly added to a solution of $AgNO_3$ (1.0 g, 5.8 mmol) in $CH_3CN$ (20 mL) at 0° C. A colorless solution with light yellow precipitate formed rapidly. The reaction mixture was allowed to warm to 25° C. and stirred for 12 h. The excess $^tBuSeH$ was removed under dynamic vacuum and a grey solid was recovered. The solid was washed with $CH_3CN$ (2×100 mL) to afford a grey solid (1.23 g, 87%).

NMR: (1H; $CDCl_3$): 1.73 (in presence of pyridine).

Example 24

Preparation of Bulk CAIS Materials

Figure 17:
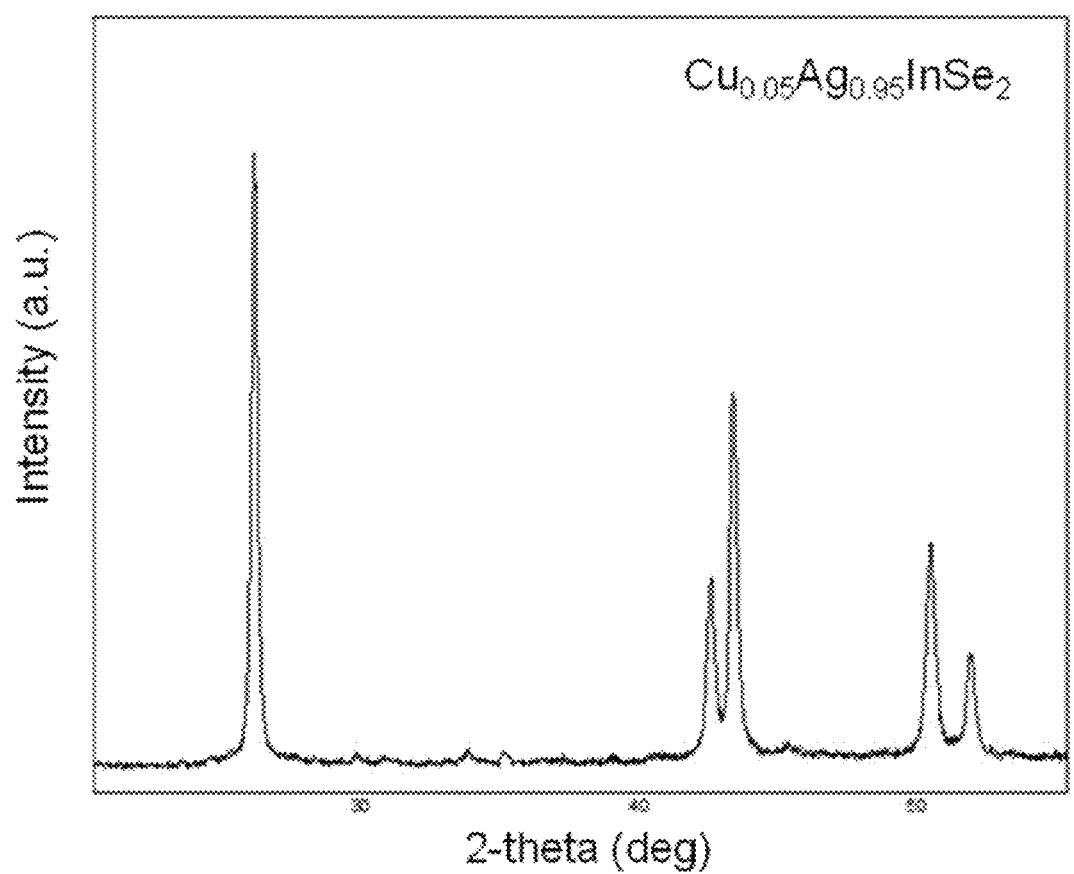
FIG. 17 shows the X-ray diffraction pattern of a CAIS material made with the polymeric precursor $\{Cu_{0.05}Ag_{0.95}(Se^sBu)_4In\}$.

A bulk CAIS material having the formula $Cu_{0.05}Ag_{0.95}InSe_2$ was prepared by heating the polymeric precursor $\{Cu_{0.05}Ag_{0.95}(Se^sBu)_4In\}$ at 10° C. per minute to a final temperature of 500° C. and holding the temperature at 500° C. for 30 minutes. The X-ray diffraction pattern of this material is shown in FIG. 17 and indicated the presence of a crystalline CAIS phase.

Example 25

Figure 18:
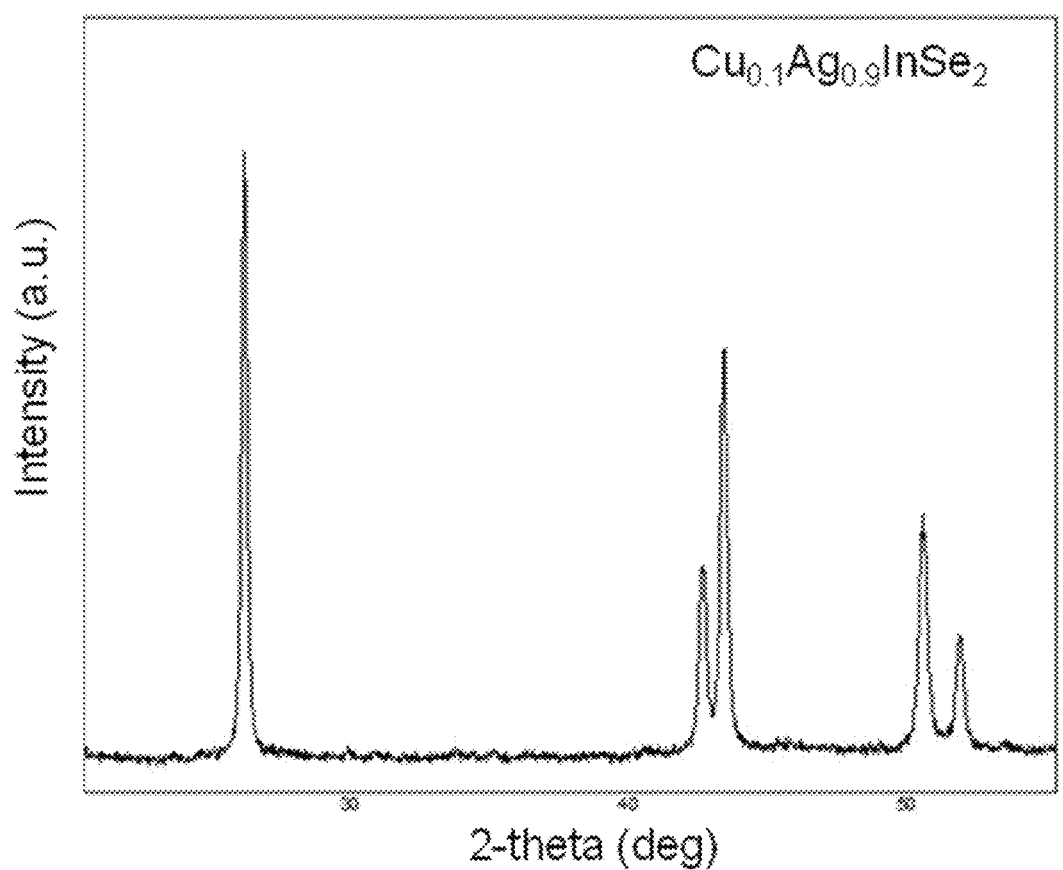
FIG. 18 shows the X-ray diffraction pattern of a CAIS material made with the polymeric precursor $\{Cu_{0.1}Ag_{0.9}(Se^sBu)_4In\}$.

A bulk CAIS material having the formula $Cu_{0.1}Ag_{0.9}InSe_2$ was prepared by heating the polymeric precursor $\{Cu_{0.1}Ag_{0.9}(Se^sBu)_4In\}$ at 10° C. per minute to a final temperature of 500° C. and holding the temperature at 500° C. for 30 minutes. The X-ray diffraction pattern of this material is shown in FIG. 18 and indicated the presence of a crystalline CAIS phase.

Example 26

Preparation of Bulk AIS Materials

Figure 19:
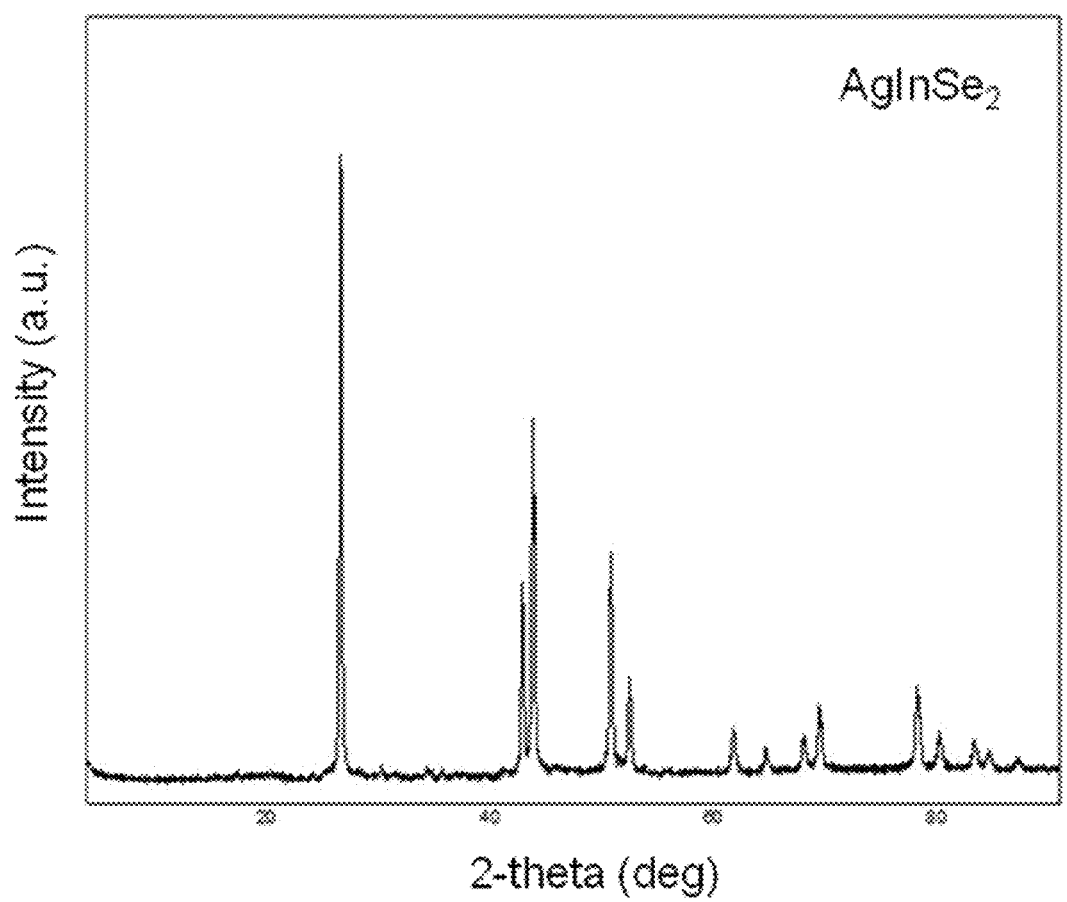
FIG. 19 shows the X-ray diffraction pattern of a AIS material made with the polymeric precursor $\{Ag(Se^sBu)_4In\}$.

A bulk AIS material having the formula $AgInSe_2$ was prepared by heating the polymeric precursor $\{Ag(Se^sBu)_4In\}$ at 10° C. per minute to a final temperature of 500° C. and holding the temperature at 500° C. for 30 minutes. The X-ray diffraction pattern of this material is shown in FIG. 19 and indicated the presence of a crystalline AIS phase.

Example 27

Figure 20:
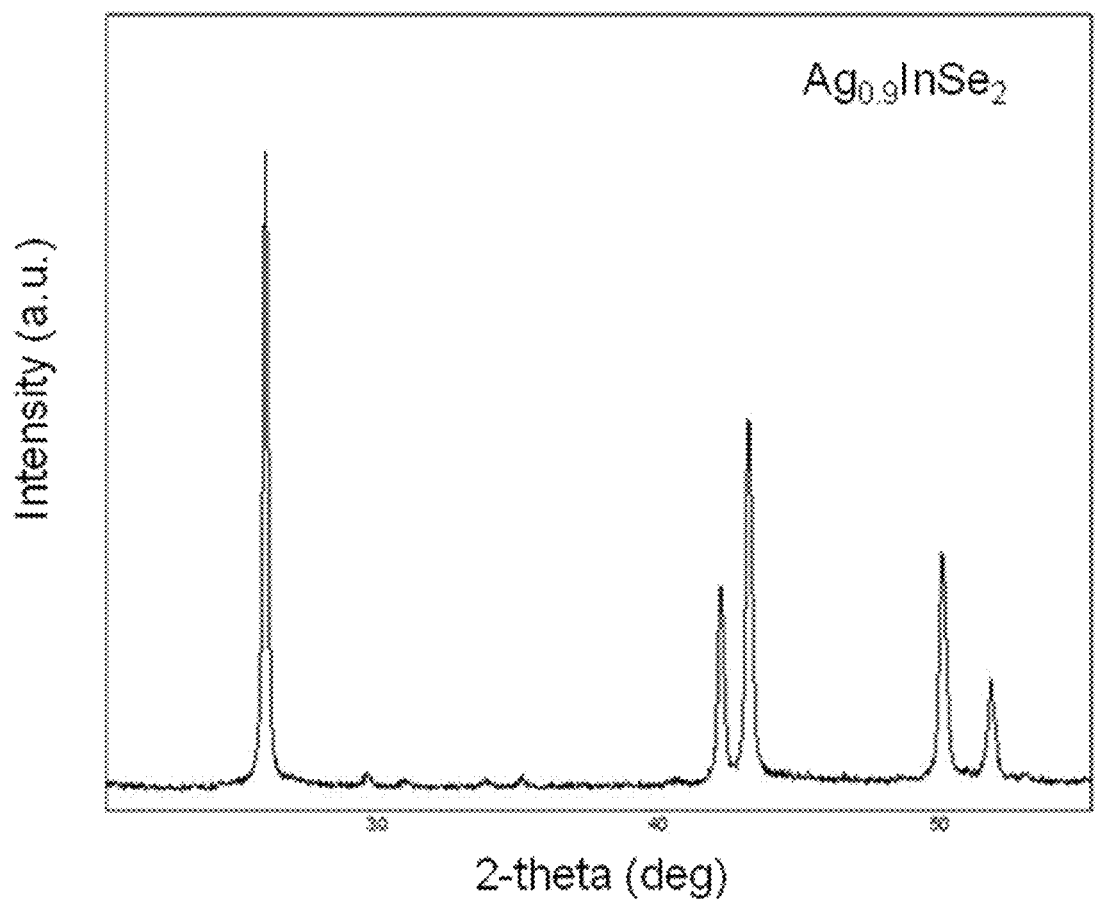
FIG. 20 shows the X-ray diffraction pattern of a AIS material made with the polymeric precursor $\{Ag_{0.9}(Se^sBu)_{3.9}In\}$.

A bulk AIS material having the formula $Ag_{0.9}InSe_2$ was prepared by heating the polymeric precursor $\{Ag_{0.9}(Se^sBu)_{3.9}In\}$ at 10° C. per minute to a final temperature of 500° C. and holding the temperature at 500° C. for 30 minutes. The X-ray diffraction pattern of this material is shown in FIG. 20 and indicated the presence of a crystalline AIS phase.

Example 28

Polymeric Precursor Ink Compositions

A polymeric precursor ink was prepared by mixing $Cu_{0.85}Ag_{0.05}(Se^sBu)_{3.9}In_{0.7}Ga_{0.3}$ with xylene (15% polymer content, by weight) in an inert atmosphere glove box. An aliquot (0.3 mL) of the ink solution was filtered through a 0.2 µm PTFE syringe filter.

Example 29

A polymeric precursor ink was made by mixing $Cu_{0.8}Ag_{0.05}(Se^sBu)_{3.85}In_{0.7}Ga_{0.3}$ with xylene (15% polymer content, by weight) in an inert atmosphere glove box. An aliquot (0.3 mL) of the ink solution was filtered through a 0.2 µm PTFE syringe filter.

Example 30

A polymeric precursor ink composition is prepared in a glovebox in an inert atmosphere by dissolving the polymeric precursor of Example 5 in THF to a concentration of 12% (w/w), and adding 0.1% (w/w) sodium relative to copper as $NaIn(Se^sBu)_4$.

Example 31

A polymeric precursor ink composition is prepared in a glovebox in an inert atmosphere by dissolving the polymeric precursor of Example 3 in a toluene solution at 20% (w/w). To this solution is added 0.05% (w/w) sodium relative to copper as $NaIn(Se^sBu)_4$.

Example 32

A polymeric precursor ink composition is prepared in a glovebox in an inert atmosphere by dissolving the polymeric precursor of Example 4 in decane to a total concentration of 20% (w/w).

Example 33

A polymeric precursor ink composition is prepared in a glovebox in an inert atmosphere by dissolving the polymeric precursor of Example 6 in decane to a total concentration of 50% (w/w).

Example 34

Polymeric Precursor Ink Compositions

A polymeric precursor ink composition is prepared in a glovebox in an inert atmosphere by dissolving the polymeric precursor of Example 10 in THF to a concentration of 12% (w/w), and adding 0.1% (w/w) sodium relative to copper as $NaIn(Se^sBu)_4$.

Example 35

A polymeric precursor ink composition is prepared in a glovebox in an inert atmosphere by dissolving the polymeric precursor of Example 10 in a toluene solution at % (w/w). To this solution is added 0.05% (w/w) sodium relative to copper as $NaIn(Se^sBu)_4$.

Example 36

A polymeric precursor ink composition is prepared in a glovebox in an inert atmosphere by dissolving the polymeric precursor of Example 12 in decane to a total concentration of 20% (w/w).

Example 37

A polymeric precursor ink composition is prepared in a glovebox in an inert atmosphere by dissolving the polymeric precursor of Example 12 in decane to a total concentration of 50% (w/w).

Example 38

Spin Casting Deposition of Polymeric Precursor Ink Compositions

A polymeric precursor ink was prepared by mixing $Cu_{0.85}Ag_{0.05}(Se^sBu)_{3.9}In_{0.7}Ga_{0.3}$ with xylene (15% polymer content, by weight) in an inert atmosphere glove box. An aliquot (0.3 mL) of the ink solution was filtered through a 0.2

μm PTFE syringe filter and deposited onto a piece of 1 inch by 1 inch Mo-coated glass substrate in a raster fashion. The substrate was spun at 1200 rpm for 1 minute using a G3P-8 Spin Coater (Specialty Coating Systems) in an inert atmosphere glove box, allowed to sit for about 2 minutes, and placed in a pre-heated (300° C.) furnace for 30 minutes for conversion of the polymer to a CAIGS material. This deposition process (filter/deposit/convert) was repeated 7 and 14 times, with the final deposition and conversion followed by annealing in a furnace at 550° C. for 1 hour. The CAIGS film resulting from 7 depositions had a thickness of about 400 nm. The CAIGS film resulting from 14 depositions had a thickness of about 850 nm.

Example 39

A polymeric precursor ink was made by mixing $Cu_{0.8}Ag_{0.05}(Se^sBu)_{3.85}In_{0.7}Ga_{0.3}$ with xylene (15% polymer content, by weight) in an inert atmosphere glove box. An aliquot (0.3 mL) of the ink solution was filtered through a 0.2 μm PTFE syringe filter and deposited onto a piece of 1 inch by 1 inch Mo-coated glass substrate in a raster fashion. The substrate was spun at 1200 rpm for 1 minute using a G3P-8 Spin Coater (Specialty Coating Systems) in an inert atmosphere glove box, allowed to sit for about 2 minutes, and placed in a pre-heated (300° C.) furnace for 30 minutes for conversion of the polymer to a CAIGS material. This deposition process (filter/deposit/convert) was repeated 7 times, with the final deposition and conversion followed by annealing in a furnace at 550° C. for 1 hour. The CAIGS film resulting from this deposition had a thickness of about 400 nm.

Example 40

Spin Casting Deposition of Polymeric Precursor Ink Compositions

An ink was prepared in an inert atmosphere glove box by mixing $AgIn(Se^nHex)_4$ with xylene (20% polymer content, by weight). An aliquot (0.3 mL) of the ink solution was filtered through a 0.2 μm PTFE syringe filter and deposited onto a piece of 1 inch by 1 inch Mo-coated glass substrate in a raster fashion. The substrate was spun at 1200 rpm for 1 minute using a G3P-8 Spin Coater (Specialty Coating Systems) in an inert atmosphere glove box, allowed to sit for about 2 minutes, and placed in a pre-heated (300° C.) furnace for 30 minutes for conversion of the polymer precursor to an AIS material. This deposition process (filter/deposit/convert) was repeated 8 times, with the final deposition/conversion followed by annealing in a furnace at 550° C. for 1 hour. The AIS film had a thickness of about 500 nm.

Example 41

Rod Coating Deposition of Polymeric Precursor Ink Compositions

A polymeric precursor ink composition is prepared in a glovebox in an inert atmosphere by dissolving the polymeric precursor of Example 5 in THF to a concentration of 12% (w/w), and adding 0.1% (w/w) sodium relative to copper as $NaIn(Se^sBu)_4$. The ink is rod coated onto a molybdenum-coated glass substrate using a K CONTROL COATER MODEL 201 (R K Print-Coat Instr., Litlington, UK) in a glovebox in an inert atmosphere.

The substrate is removed and is heated at a temperature of 350° C. in an inert atmosphere. A thin film material is produced which is a photovoltaic absorber layer. The final film thickness is 1 micron.

Example 42

A polymeric precursor ink composition is prepared in a glovebox in an inert atmosphere by dissolving the polymeric precursor of Example 3 in a toluene solution at 20% (w/w). To this solution is added 0.05% (w/w) sodium relative to copper as $NaIn(Se^sBu)_4$. The ink is rod coated onto a molybdenum-coated glass substrate using a K CONTROL COATER MODEL 201 (R K Print-Coat Instr., Litlington, UK) in a glovebox in an inert atmosphere.

The substrate is removed and is heated at a temperature of 380° C. in an inert atmosphere A thin film material is produced which is a photovoltaic absorber layer. The final film thickness is 1.5 micron.

Example 43

Dip Coating Deposition of Polymeric Precursor Ink Compositions

A polymeric precursor ink composition is prepared in a glovebox in an inert atmosphere by dissolving the polymeric precursor of Example 4 in decane to a total concentration of 20% (w/w). The ink is dip coated onto an aluminum substrate in an inert atmosphere.

The substrate is removed and is heated at a temperature of 340° C. in an inert atmosphere A thin film material is produced which is a photovoltaic absorber layer. The final film thickness is 2.5 micron.

Example 44

Slot Die Coating Deposition of Polymeric Precursor Ink Compositions

A polymeric precursor ink composition is prepared in a glovebox in an inert atmosphere by dissolving the polymeric precursor of Example 5 in THF to a concentration of 12% (w/w), and adding 0.1% (w/w) sodium relative to copper as $NaIn(Se^sBu)_4$. The ink is slot die coated onto a Mo-coated glass substrate in an inert atmosphere.

The substrate is removed and is heated at a temperature of 300° C. in an inert atmosphere A thin film material is produced which is a photovoltaic absorber layer. The final film thickness is 1.5 micron.

Example 45

A polymeric precursor ink composition is prepared in a glovebox in an inert atmosphere by dissolving the polymeric precursor of Example 3 in a toluene solution at 20% (w/w). To this solution is added 0.05% (w/w) sodium relative to copper as $NaIn(Se^sBu)_4$. The ink is slot die coated onto a molybdenum-coated stainless steel substrate in an inert atmosphere.

The substrate is removed and is heated at a temperature of 380° C. in an inert atmosphere A thin film material is produced which is a photovoltaic absorber layer. The final film thickness is 2.0 micron.

Example 46

Screen Printing Deposition of Polymeric Precursor Ink Compositions

A polymeric precursor ink composition is prepared in a glovebox in an inert atmosphere by dissolving the polymeric precursor of Example 6 in decane to a total concentration of 50% (w/w). The polymeric precursor ink is screen printed onto a molybdenum-coated stainless steel substrate in an inert atmosphere.

The substrate is removed and is heated at a temperature of 400° C. in an inert atmosphere. A thin film material is produced which is a photovoltaic absorber layer. The final film thickness is 2.8 micron.

Example 47

Printing Polymeric Precursor Ink Compositions

A polymeric precursor ink is prepared by mixing $Cu_{0.85}Ag_{0.05}(Se^sBu)_{3.9}In_{0.7}Ga_{0.3}$ with xylene (1% polymer content, by weight) in an inert atmosphere glove box. The ink is printed onto a molybdenum-coated stainless steel substrate using an M3D Aerosol Jet Deposition System (Optomec, Albuquerque) in a glovebox in an inert atmosphere.

The substrate is removed and is heated at a temperature of 375° C. in an inert atmosphere. A thin film material is produced which is a photovoltaic absorber layer. The final film thickness is 500 nm.

Example 48

A polymeric precursor ink is prepared by mixing $Cu_{0.85}Ag_{0.05}(Se^sBu)_{3.9}In_{0.7}Ga_{0.3}$ with xylene (1% polymer content, by weight) in an inert atmosphere glove box. The ink is printed onto a molybdenum-coated glass substrate using a DIMATIX DMP-2831 materials printer (Fujifilm Dimatix, Lebanon, N.H.) in a glovebox in an inert atmosphere.

The substrate is removed and is heated at a temperature of 400° C. in an inert atmosphere A thin film material is produced which is a photovoltaic absorber layer. The final film thickness is 750 nm.

Example 49

Spray Pyrolysis Deposition of Polymeric Precursor Ink Compositions

A polymeric precursor ink composition is prepared in a glovebox in an inert atmosphere by dissolving the polymeric precursor of Example 5 in cyclohexanone to a concentration of 5% (w/w), and adding 0.1% (w/w) sodium relative to copper as $NaIn(Se^sBu)_4$. The ink is sprayed onto an aluminum substrate using a spray pyrolysis unit in a glovebox in an inert atmosphere, the spray pyrolysis unit having an ultrasonic nebulizer, precision flow meters for inert gas carrier, and a tubular quartz reactor in a furnace.

The spray-coated substrate is heated at a temperature of 350° C. in an inert atmosphere. A thin film material is produced which is a photovoltaic absorber layer. The final film thickness is 2 micron.

Example 50

Preparation of a Solar Cell

A solar cell is made by depositing an electrode layer on a polyethylene terephthalate substrate.

A thin film material photovoltaic absorber layer is coated onto the electrode layer according to the following procedure. A polymeric precursor ink composition is prepared in a glovebox in an inert atmosphere by dissolving the polymeric precursor of Example 5 in THF to a concentration of 12% (w/w), and adding 0.1% (w/w) sodium relative to copper as $NaIn(Se^sBu)_4$. The ink is slot die coated onto a Mo-coated glass substrate in an inert atmosphere. The substrate is removed and is heated at a temperature of 300° C. in an inert atmosphere A thin film material is produced which is a photovoltaic absorber layer. The final film thickness is 1.5 micron.

A CdS window layer is deposited on the absorber layer. An aluminum-doped ZnO TCO layer is deposited onto the window layer.

What is claimed is:

1. A method for making a material comprising,
   (a) providing one or more AIGS, AIS or AGS polymeric precursor compounds or inks thereof;
   (b) providing a substrate;
   (c) depositing the compounds or inks onto the substrate; and
   (d) heating the substrate at a temperature of from about 20° C. to about 650° C. in an inert atmosphere, thereby producing a material;
   wherein the polymeric precursor compound has the empirical formula $Ag_u(M^{B1}_{1-y}M^{B2}_y)_v((S_{1-z}Se_z)R)_w$, wherein $M^{B1}$ and $M^{B2}$ are different atoms of Group 13, y is from 0.001 to 0.999, z is from 0 to 1, u is from 0.5 to 1.5, v is from 0.5 to 1.5, w is from 2 to 6, and R represents R groups, of which there are w in number, which are each independently selected from the group consisting of alkyl, aryl, heteroaryl, alkenyl, amido, and silyl.

2. The method of claim 1, wherein the material is an AIGS, AIS or AGS material.

3. The method of claim 1, wherein the material is enriched or deficient in a Group 11 atom.

4. The method of claim 1, wherein the substrate is heated at a temperature of from about 100° C. to about 550° C.

5. The method of claim 1, wherein the substrate is heated at a temperature of from about 200° C. to about 400° C.

6. The method of claim 1, wherein the depositing is done by a method selected from the group consisting of spraying, spray coating, spray deposition, spray pyrolysis, printing, screen printing, inkjet printing, aerosol jet printing, ink printing, jet printing, stamp/pad printing, transfer printing, pad printing, flexographic printing, gravure printing, contact printing, reverse printing, thermal printing, lithography, electrophotographic printing, electrodepositing, electroplating, electroless plating, bath deposition, coating, wet coating, spin coating, knife coating, roller coating, rod coating, slot die coating, meyerbar coating, lip direct coating, capillary coating, liquid deposition, solution deposition, layer-by-layer deposition, spin casting, solution casting, and combinations of any of the forgoing.

7. The method of claim 1, wherein the substrate is selected from the group consisting of a semiconductor, a doped semiconductor, silicon, gallium arsenide, insulators, glass, molybdenum glass, silicon dioxide, titanium dioxide, zinc oxide, silicon nitride, a metal, a metal foil, molybdenum, aluminum, beryllium, cadmium, cerium, chromium, cobalt, copper, gallium, gold, lead, manganese, molybdenum, nickel, palladium, platinum, rhenium, rhodium, silver, stainless steel, steel, iron, strontium, tin, titanium, tungsten, zinc, zirconium, a metal alloy, a metal silicide, a metal carbide, a polymer, a plastic, a conductive polymer, a copolymer, a polymer blend, a polyethylene terephthalate, a polycarbonate, a polyester, a polyester film, a mylar, a polyvinyl fluoride, polyvinylidene fluoride, a polyethylene, a polyetherimide, a polyethersulfone, a polyetherketone, a polyimide, a polyvinylchloride, an acrylonitrile butadiene styrene polymer, a silicone, an epoxy, paper, coated paper, and combinations of any of the forgoing.

8. The method of claim 1, wherein the substrate is a shaped substrate, a tube, a cylinder, a roller, a rod, a pin, a shaft, a plane, a plate, a blade, a vane, a curved surface or a spheroid.

9. The method of claim 1, wherein the substrate is a layer of a solar cell.

10. The method of claim 1, further comprising an optional step of selenization or sulfurization, either before, during or after steps (c) or (d).

11. The method of claim 1, wherein the material is a semiconductor.

12. The method of claim 1, wherein the material is a photovoltaic.

13. The method of claim 1, wherein the material is a thin film.

14. The method of claim 1, wherein the material is a thin film with a thickness of from 0.001 to 100 micrometers.

15. The method of claim 1, wherein the material is a thin film with a thickness of from 0.1 to 10 micrometers.

16. A material made by the method of claim 1.

17. A photovoltaic device comprising a material made by the method of claim 1.

18. A system for providing electrical power comprising the photovoltaic device of claim 17.

19. A method for providing electrical power comprising using the system of claim 18 to convert light into electrical energy.

* * * * *